(12) United States Patent
Schwartz et al.

(10) Patent No.: US 7,811,820 B2
(45) Date of Patent: Oct. 12, 2010

(54) SMOOTH MUSCLE CELL DIFFERENTIATION WITH CRP, SRF AND GATA FACTORS

(75) Inventors: Robert J. Schwartz, Houston, TX (US); Narasimhaswamy Belaguli, Houston, TX (US); Joe Marx, Houston, TX (US); David Chang, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 984 days.

(21) Appl. No.: 10/754,861

(22) Filed: Jan. 9, 2004

(65) Prior Publication Data

US 2005/0037961 A1    Feb. 17, 2005

Related U.S. Application Data

(60) Provisional application No. 60/439,345, filed on Jan. 10, 2003.

(51) Int. Cl.
*C12N 5/07* (2010.01)

(52) U.S. Cl. .................................................. 435/377

(58) Field of Classification Search ........................ None
See application file for complete search history.

(56) References Cited

U.S. PATENT DOCUMENTS

2002/0061587 A1    5/2002    Anversa

FOREIGN PATENT DOCUMENTS

WO         WO-00/17326         3/2000

OTHER PUBLICATIONS

Nishida et al (J. Biol. Chem. 277(9): 7308-7317, 2002).*
Yoshida et al (Arterioscler. Thromb. Vasc. Biol 24: 1596-1601, 2004).*
Hirschi et al (Circ. Res. 84: 298-305, 1999).*
Manabe et al (Circ. Res. 88: 1127-1134, 2001).*
Manabe et al (J. Clin. Invest. 107(7): 823-834, 2001).*
Parmacek (Arterioscler. Thromb. Vasc. Biol 24: 1535-1537, 2004).*
Majesky et al (Circ Res. 92: 824-826, 2003).*
Weiss et al (Exp. Hematol. 23(2): 99-107, 1995).*
Molkentin (J. Biol. Chem. 273(50): 38949-38952, 2000).*
Chang et al (Dev. Cell 4:107-118, 2003).*
Verma et al (Nature 389: 239-242, 1997).*
Anderson (Nature 392:25-30, 1998).*
Romano et al (Stem Cells 18: 19-39, 2000).*
Somia and Verma (Nature Reviews Genetics 1: 91-99, 2000).*
Rosenberg et al, Science 287:1751, 2000.*
Juengst (BMJ 326: 1410, 2003).*
Miller et al. (FASEB J. 9: 190-199, 1995).*
Deonarain (Exp. Opin. Ther. Patents 8(1):53-69, 1998).*
Crystal (Science 270: 404-410, 1995).*
Pouton et al (Adv. Drug Del. Rev. 46: 187-203, 2001).*
Read et al (Adv. Gen. 53:19-46, 2005).*
Drab et al (FASEB J. 11: 905-915, 1997).*
Sachinidis et al (Card. Res. 58: 278-291, 2003).*
Goldberg-Cohen et al (Meth. Enzymol. 418: 252-266, 2006).*
Davis, Francesca, J., et al., "Increased expression of alternatively spliced dominant-negative isoform of SRF in human failing hearts", Am. J. Physiol Heart Circ. Physiol, vol. 282, (2002) pp. H1521-H1533.
Ferber, Dan, "Lab-Grown Organs Begin to Take Shape", Science, vol. 284, (Apr. 1999), p. 422-425.
Michelsen, James W., et al., "The LIM motif defines a specific zinc-binding protein domain", Proc. Natl. Acad. Sci. USA, vol. 90, (May 1993) pp. 4404-4409.
Moore, Meredith L., et al., "GATA-4 and Serum Response Factor Regulate Transcription of the Muscle-specific carnitine palmitoyltransferase I β in Rat Heart", Jol. of Bio. Chem., vol. 276, No. 2, (Jan. 2001), pp. 1026-1033.
Morin, Steves, et al., "Serum Response Factor-GATA Ternary Complex Required for Nuclear Signaling by a G-Protein-Coupled Receptor", Molecular & Cellular Bio., vol. 21, No. 4, (Feb. 2001), p. 1036-1044.
Muller, Joachim, G., et al., "Differential Regulation of the Cardiac Sodium Calcium Exchanger Promoter in Adult and Neonatal Cardiomyocytes by Nkx2.5 and Serum Response Factor," J. Mol. Cell Cardiol., vol. 34, (2002) pp. 807-821.
Belaguli, Narasimhaswamy, et al., "Cardiac Tissue Enriched Factors Serum Response Factor and GATA-4 Are Mutual Coregulators", Molecular & Cellular Bio., vol. 20, No. 20 (Oct. 2000) pp. 7550-7558.
Belaguli, Narasimhaswamy, et al., "Dominant Negative Murine Serum Response Factor: Alternative Splicing within the Activation Domain Inhibits Transactivation of Serum Response Factor Binding Targets," Molecular & Cellular Bio., vol. 19, No. 7 (Jul. 1999), pp. 4582-4591.
Niklason, L.E., et al, "Functional Arteries Grown in Vitro", Science, vol. 284, (Apr. 1999), pp. 489-493.
Noveroske, Janice, et. al, "Quaking is Essential for Blood Vessel Development," Genesis, vol. 32 (2002) pp. 218-230.
Sepulveda, Jorge, et al., "GATA-4 and Nkx-2.5 Coactivate Nkx-2 DNA Binding Targets: Role for Regulating Early Cardiac Gene Expression", Molecular & Cellular Bio. vol. 18, No. 6. (Jun. 1998) pp. 3405-3415.
Weiskirchen, Ralf, et al, "The Cysteine-rich Protein Family of Highly Related LIM Domain Proteins", Jol. of Bio. Chem., vol. 270, No. 48 (Dec. 1995) pp. 28946-28954.
Zhang, Xiaomin, et al., "Early Postnatal Cardiac Changes and Premature Death in Transgenic Mice Overexpressing a Mutant Form of Serum Response Factor," Jol. of Bio. Chem., vol. 276, No. 43 (Oct. 2001), pp. 40033-40040.

* cited by examiner

*Primary Examiner*—Richard Schnizer
(74) *Attorney, Agent, or Firm*—Jackson Walker L.L.P.

(57) ABSTRACT

The present invention is directed to generating a smooth muscle cell from another cell, such as a fibroblast, by delivering to the cell serum response factor, a CRP, and a GATA. In specific embodiments, the methods are utilized to generate vascular tissue and/or to repair vascular tissue.

15 Claims, 26 Drawing Sheets

A

TAT-CRP (25 kD)

| His$_6$ | PTD | HA | CRP2 |

TAT-β-GAL (120 kD)

| His$_6$ | PTD | HA | β-GAL |

B

SMOOTH MUSCLE CELL DIFFERENTIATION WITH CRP, SRF AND GATA FACTORS

The present application claims priority to U.S. Provisional Patent Application Ser. No. 60/439,345, filed Jan. 10, 2003, which is incorporated by reference herein in its entirety.

The present invention utilized grant funds. Therefore, the United States Government may have certain rights in the invention.

FIELD OF THE INVENTION

The present invention relates to the fields of cell biology, molecular biology, and medicine. Specifically, the invention is directed to smooth muscle cell differentiation. More specifically, the invention is directed to cardiac disease therapy.

BACKGROUND OF THE INVENTION

The cardiovascular system is among the earliest organs to form in mammals. De novo gene expression of smooth muscle contractile protein genes appears in the heart-forming regions providing molecular markers for promyocardial cells well before overt cardiac morphogenesis (Colas et al., 2000). Robust expression of the smooth muscle α-actin (SMA) gene marked the onset of differentiation of cardiac cells and represented the first demonstration of coexpression of both smooth muscle and striated α-actin genes within myogenic cells (Ruzicka and Schwartz, 1988). Cardiovascular smooth muscle differentiation depends upon the integration of complex signaling inputs with activation of serum response factor (SRF)-dependent transcription. SRF contains a highly conserved DNA-binding/dimerization domain termed the MADS box that integrates intracellular signals and assists as a docking surface for the binding of cofactors, which may confer the regulation of specific gene programs (reviewed in Reecy et al., 1999; Gineitis and Treisman, 2001). The knockout of the murine SRF gene locus supports the observation that SRF is absolutely required for the appearance of muscle mesoderm during mouse embryogenesis (Arsenian et al., 1998). While numerous studies have established the importance of an evolutionarily-conserved, SRF-binding cis element termed an SRE or CArG box [CC(AT)$_6$GG; SEQ ID NO:1] in control of smooth muscle cell (SMC)-specific gene expression (Li et al., 1997; Kim et al, 1997; Belaguli et al., 1999; Mack and Owens, 1999; Miano et al., 2000), it is clear that SRF-SRE interactions, by themselves, are not sufficient to direct SMC differentiation from committed progenitor cells.

Proteins that act to organize higher-order multi-protein complexes that contain SRF and stimulate SMC-restricted gene transcription in an SRE-dependent and developmental signal-responsive manner have been sought. Recently, Sepulveda et al. (2002) demonstrated that the expression of SRF, Nkx2-5 and GATA4 was central for activation of embryonic cardiac α-actin gene activity. Nishida et al. (2002) showed the combinatorial interaction of SRF, Nkx-3.2 and GATA-6 activated promoters of smooth muscle genes. Wang et al. (2001) showed that myocardin, a SAP factor, enriched during cardiogenesis, also served as a powerful SRF co-accessory factor (Wang et al., 2001). However, the precise combination of regulatory factors that fosters distinct cardiac and smooth muscle cell lineages has not been previously elucidated.

Of interest in this regard are the LIM domain-containing members of the cysteine-rich protein (CRP) family. LIM domains are double zinc finger-like structures that mediate protein-protein interactions and may target proteins to distinct subcellular locations and mediate assembly of multimeric protein complexes (Dawid et al., 1995; Louis et al., 1997). Each member of the CRP family contains two LIM domains with associated glycine-rich repeats. Three members of the CRP family (CRP1, CRP2/SmLIM and CRP3/MLP) have been characterized in vertebrates (Liebhaber et al., 1990; Weiskirchen et al., 1993; Arber et al., 1994) and all three appear to have comparable functions in different cell types. CRP1 is expressed in multiple adult organs, including those enriched in smooth muscle such as arteries, stomach, gizzard and intestine (Henderson, et al, 1999). CRP2 is expressed mainly in vascular SMCs and is down-regulated upon their dedifferentiation and proliferation in response to stress or injury, such as occurs in arteriosclerosis (Jain et al., 1996). Expression of CRP3 is limited to striated muscle cells of heart and skeletal muscle, and CRP3-deficient mice develop heart failure soon after birth (Arber et al., 1997).

One distinguishing feature of the three CRPs is their association with adhesion plaques and with filamentous actin. These proteins do not bind actin directly, but all three interact with both the actin cross-linking protein α-actinin and the adhesion plaque protein zyxin and may regulate the stability and structure of adhesion complexes. (Schmeichel and Beckerle, 1994; Arber and Caroni, 1996; Pomies et al., 1997) However, in a specific embodiment, this cytoplasmic role for the CRP proteins is not their only, or possibly even their most critical, function during cell differentiation. The present invention is directed to methods and compositions related to the CRP proteins for cell differentiation and, in some embodiments, for cardiac disease therapy.

Serum response factor expression is required for induction of a smooth muscle phenotype in mesenchymal cells and is sufficient for transforming growth factor-beta-mediated smooth muscle induction (Hirschi et al., 2002).

BRIEF SUMMARY OF THE INVENTION

The present invention is directed to a system, method, and compositions related to smooth muscle cell differentiation from a non-smooth muscle cell, also referred to herein as a progenitor cell, using SRF, CRP, and GATA factors. In a specific embodiment, the non-smooth muscle cell from which the smooth muscle cell is differentiated is a noncardiogenic cell, such as a fibroblast or a stem cell. In a specific embodiment, the cell is a non-myogenic cell. In a specific embodiment, the cell is an embryonic stem cell. In another specific embodiment, the cell is a cell that naturally would not have developed into one of cardiovascular lineage, but following manipulations comprising delivery of SRF, CRP, and GATA factors, the cell develops into one of cardiovascular lineage.

In specific embodiments, CRP2 and GATA6 are preferred factors. In further specific embodiments, all three factors are co-transfected into the non-smooth muscle cell from which the smooth muscle cell is differentiated, therein upregulating expression of at least one smooth muscle cell-specific polynucleotide.

Examples provided herein illustrate the restricted expression of CRP1 and CRP2 in early vertebrate embryos that was coincident with the earliest appearance of smooth muscle gene targets and nascent myocardial cells. CRP2 was identified in the nucleus during the early differentiation of smooth muscle cells. Furthermore, evidence is provided herein to indicate that CRP1 and CRP2 function as transcription cofactors that form complexes with SRF and a GATA, such as GATA6, to promote de novo upregulation of smooth muscle specified genes, central for cardiovascular SMC differentiation.

It is presented herein that cysteine-rich LIM-only proteins, CRP1 and CRP2, expressed during cardiovascular development, act as bridging molecules that associate with serum response factor and GATA proteins. SRF-CRP-GATA complexes strongly activated smooth muscle gene targets. CRP2 was found in the nucleus during early stages of coronary smooth muscle differentiation from proepicardial cells. A dominant negative CRP2 mutant blocked proepicardial cells from differentiating into smooth muscle cells. Together with SRF and GATA proteins, CRP1 and CRP2 converted pluripotent 10T1/2 fibroblasts into smooth muscle cells, while muscle LIM protein, CRP3, inhibited the conversion. Thus, LIM-only proteins of the CRP family play important roles in organizing multiprotein complexes both in the cytoplasm, where they participate in cytoskeletal remodeling, and in the nucleus, where they strongly facilitate smooth muscle differentiation.

In one embodiment of the present invention, there is conversion of a non-myogenic cell to a cardiovascular cell having properties similar to a smooth muscle cell. In a specific embodiment, the properties comprise expression of smooth muscle alpha actin, SM22alpha, calponin, caldesmon, and smooth muscle myosin heavy chain.

In an embodiment of the present invention, there is conversion of a cell of pleimorphic fibroblast morphology into a bipolar-appearing cell.

In an embodiment of the present invention, there is a method of upregulating expression of a smooth muscle polynucleotide in a cell, comprising the step of delivering serum response factor (SRF), a cysteine-rich LIM-only protein (CRP), and a GATA to the cell, wherein the CRP comprises at least one operable LIM domain. In a specific embodiment, the CRP is CRP1, CRP2, or CRP3. In another specific embodiment, the CRP comprises a nuclear localization signal. In a further specific embodiment, the GATA is GATA-2, GATA-4 or GATA-6. In an additional specific embodiment, the CRP2, SRF, and a GATA are delivered substantially concomitantly. In a further specific embodiment, at least one of CRP2, SRF, and GATA are delivered as a polypeptide to the cell. In an additional specific embodiment, at least one of CRP2, SRF, and GATA is delivered as a polynucleotide to the cell. In a further specific embodiment, the polynucleotide is in a vector, such as a viral vector or a non-viral vector. In a specific embodiment, the viral vector is an adenoviral vector, an adeno-associated vector, or a retroviral vector. In a further specific embodiment, the smooth muscle polynucleotide is an early smooth muscle specific polynucleotide, such as smooth muscle α-actin, or SM22α. In a specific embodiment, the cell is in a tissue and in another specific embodiment, the tissue is in a human.

In an additional embodiment of the present invention, there is a method of generating a smooth muscle cell from a fibroblast cell, comprising the step of delivering SRF, a CRP, and a GATA to the fibroblast cell. In specific embodiments, the fibroblast is derived from autologous tissue, allogeneic tissue, and/or xenogeneic tissue. In a specific embodiment, the smooth muscle cell is defined as a cell comprising at least one of the following expression of smooth muscle α-actin; expression of calponin; expression of smooth muscle myosin heavy chain; expression of dHAND; and expression of CRP3.

In another embodiment of the present invention, there is a method of generating a smooth muscle cell from a stem cell, comprising the step of delivering SRF, a CRP, and a GATA to the stem cell.

In an additional embodiment of the present invention, there is a method of repairing a damaged blood vessel, comprising the steps of generating a smooth muscle cell by delivering to a non-smooth muscle cell a SRF, a CRP, and a GATA; culturing said smooth muscle cell; generating a tissue from said smooth muscle cell; and repairing said damaged blood vessel with said tissue.

In another embodiment of the present invention, there is a method of repairing damaged cardiovascular tissue, comprising the steps of generating a smooth muscle cell by delivering to a non-smooth muscle cell a SRF, a CRP, and a GATA; growing said smooth muscle cell to generate a smooth muscle cell culture; generating smooth muscle cell-comprising cardiovascular tissue from at least one cell from said smooth muscle cell; and repairing said damaged cardiovascular tissue with said smooth muscle cell-comprising cardiovascular tissue. In a specific embodiment, the cardiovascular tissue is a damaged blood vessel. In a further specific embodiment, the blood vessel is an artery.

In another embodiment of the present invention, there is a method of treating cardiac disease in an individual, said individual comprising a cell, comprising the step of delivering SRF, a CRP, and a GATA to the cell. In specific embodiments, the method is further defined as obtaining a cell from the individual; delivering SRF, a CRP, and a GATA to said cell; growing said cell to form a cell culture; and delivering at least one cell from said cell culture to said individual. In further specific embodiments, the delivering at least one cell from said cell culture to said individual is further defined as generating a tissue from said at least one cell from said cell culture; and administering said tissue to said individual.

In an additional embodiment of the present invention, there is a pharmaceutical composition comprising a therapeutically effective amount of a plurality of smooth muscle cells in a pharmaceutically acceptable excipient, wherein at least one smooth muscle cell in said plurality is differentiated from a non-smooth muscle cell by delivery of SRF, a CRP, and a GATA to said non-smooth muscle cell.

In another embodiment of the present invention, there is a pharmaceutical composition comprising SRF, a CRP, and a GATA, wherein at least one of SRF, a CRP, and a GATA is in a pharmaceutically acceptable excipient. In a specific embodiment, the composition further comprises at least one non-smooth muscle cell.

In an additional embodiment of the present invention, there is a kit comprising a pharmaceutical composition comprising SRF, a CRP, and a GATA, wherein at least one of SRF, a CRP, and a GATA is in a pharmaceutically acceptable excipient, said composition housed in a suitable container. In a specific embodiment, the kit further comprises at least one non-smooth muscle cell.

In one embodiment of the present invention, there is a method of generating cardiac tissue, comprising the steps of generating a smooth muscle cell from a non-smooth muscle cell by delivering SRF, CRP2, and GATA6 on at least one polynucleotide to the non-smooth muscle cell; and generating said cardiac tissue from said smooth muscle cell.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 1A shows whole mount in situ hybridization of CRP1. FIG. 1B shows whole mount in situ hybridization of CRP2. FIG. 1C shows endogenous CRP2 expression in proepicardial cells during differentiation to CoSMCs.

FIG. 2A shows that transcriptional activity of SMA was measured in CV1 cells using a luciferase-reporter assay, with the indicated combination of expression plasmids. The results of three repeated transient co-transfection experiments performed in duplicate are presented in FIGS. 2A-2D. show values are expressed as fold-activation increases in luciferase activity ±SEM compared to the level of activity with empty expression vector alone. FIG. 2B shows a transactivation assay of CArG box-containing SMC-restricted genes in CV1 cells. The promoter-reporter constructs used are shown schematically. FIG. 2C demonstrates minimal SRE reporter, c-fos SRE1-Luc, results in weak co-activation in CV1 cells. FIG. 2D demonstrates mutation in either SRE on the SMA promoter reduces the synergistic transactivation in CV1 cells, while double-SRE mutation results in null activity. Relative transactivation was determined by comparison to the wild type promoter-reporter.

FIG. 3A shows mammalian two-hybrid assays determined that the minimal DNA-binding domain of SRF (MADS box) facilitated the recruitment of CRP2 to the Gal4 minimal promoter. A schematic model of assayed interactions is shown in panel A. FIG. 3B shows co-immunoprecipitation (co-IP) experiments that demonstrate CRP2, SRF and GATA6 proteins co-associate. Whole cell lysates (WCL) of CV1 cells co-transfected with pcDNA3.1-V5-CRP2, pCGN-SRF (HA-tag), pcDNA3.1-myc-GATA6, and pcDNA3.1-FLAG-E12 were subjected to IP using either anti-V5 (lane1), anti-HA (lane 2), anti-myc (lane 3), or anti-FLAG (lane 4). IP products were analyzed by Western immunoblot (WB) using anti-V5 for CRP2 (top panel), anti-HA for SRF (second panel), anti-myc for GATA6 (third panel), and anti-FLAG for E12 (bottom panel). Ten percent of whole cell lysate (WCL) was loaded in lane 5. (FIG. 3C) EMSAs of the SMA promoter show that CRP2 and GATA4 recruited by SRF vastly increased cooperative SRF DNA binding affinity. The faster complex represents the occupation of either SRE1 and or SRE2 (C1). The second slower complex represents occupation of both SRE1 and SRE2 (C2). Ternary complexes were also resolved above C1 and C2. The addition of SRF antibody resulted in 2 super shifted complexes with reduced levels of C1 and C2 complexes while the addition of anti-GST-CRP2 antibody only reduced the level of C1 complex. Anti-GATA4 antibody did not produce a super shift, indicating possible interference of the protein-protein bind site with the epitope.

FIG. 4A illustrates that the N-terminal LIM domain mediates SRF-CRP2 binding while the C-terminal LIM is required for CRP2-GATA4 co-association. Pull-down analyses were performed on [$^{35}$S]methionine-labeled, in vitro translated proteins using GST-SRF (lane 3) or MBP-GATA4 fusion protein (lane 6). GST (lane 2) or MBP (lane 5) protein was used as negative control. The associated proteins were visualized by autoradiography. One-fifth the amount of labeled translated proteins was loaded as positive control (lane 1, 4). FIG. 4B shows that luciferase assay in CV1 cells correlates with the binding specificity of CRP2 mutants and the synergistic transactivation on SMA reporter. FIG. 4C shows GST pull-down analysis performed on [$^{35}$S]methionine-labeled, in vitro translated proteins using GST control (lane 2) or GST-CRP (lane 3) fusion protein. The associated proteins were visualized by autoradiography. One-fifth the amount of labeled translated proteins was loaded as positive control (lane 1). FIG. 4D demonstrates luciferase assay in CV1 cells correlates the binding specificity of GATA4 mutants and the synergistic transactivation on SMA reporter.

FIG. 5A shows RT-PCR analysis indicated activation of endogenous SMC genes in 10T1/2 cells cotransfected with the indicated expression plasmids. CRP1 and CRP2, but not CRP3, in combination with SRF and GATA4 have similar effect in SMC transdifferentiation. FIG. 5B shows immunofluorescent staining showed expression of the full complement of SMC markers in 10T1/2 cells receiving the triple combination of factors, compared to the control group. FIG. 5C shows western blot analysis confirmed the induction of SMC target genes in 10T1/2 cells is SMC-specific. Cardiac α-actin (A) and striated muscle-specific sarcomeric α-actin (C) were not detected in this transdifferentiation study, indicating that the differentiation pattern was SMC specific. Mouse uterus, heart, and soleus muscle tissues were extracted and used as control for smooth, cardiac and skeletal muscle, respectively.

FIG. 6A shows luciferase-reporter assay was performed to measure the transcriptional activity of SMA in CV1 cells, with the indicated combination of expression plasmids. Mutant CRP2 plasmids CRP2ΔN or CRP2ΔC were cotransfected with wild type CRP2 in a 1:1 (lanes 5 and 8), 1:2 (lanes 6 and 9) or 1:5 ratio (lanes 7 and 10). FIG. 6B shows freshly isolated PEO explants were transfected with CRP2ΔN mutant or wild type CRP2 plasmids. Double immunofluorescent staining of V5-tag CRP2ΔN or CRP2 was implemented 2 to 3 days later to evaluate the effect on SMC marker protein expression. Indirect immunofluorescence analysis shows PEO cells that expressed the dominant negative mutant did not co-express SMA, calponin, or SMγA. In contrast, wild type CRP2 expression did not interfere with SMC marker protein SMγA expression.

In FIG. 8A, there is a summary showing schematic view of wild type CRP2 and four fusion protein expression constructs, their cellular localization and transfection efficiency. Indirect immunofluorescent staining of CV1 cells overexpressing V5-tagged proteins (green). WT, wild type; NLS, SV40 nuclear localization signal; NES, PKI nuclear export signal; SR, Mxi1 strong repression domain; SRpm, Mxi1 strong repressor domain point mutant. In FIG. 8B, there are effects of regulated cellular redistribution of CRP2 on SMA gene activation. CV1 cells were cotransfected with SMA-luciferase reporter and expression vectors encoding SRF, GATA6, and various CRP2 constructs, as indicated. Values are expressed as fold-activation increases in luciferase activity ±SEM compared to the level of activity with empty expression vector alone (lane 1).

In FIG. 9A, there is indirect immunofluorescent analysis of V5 epitope-tagged CRP2 (green) in CV1 cells. Untreated control CV1 cells show global localization of CRP2. CRP2 accumulate in the nucleus after one hour of treatment with nuclear export inhibitor leptomycin B (LMB), Rho-kinase inhibitor Y-27632 or actin depolymerization drug cytochalasin D. Filamentous actins were stained with rhodamine phalloidin (red). In FIG. 9B, Y-27632 induces CRP2 nuclear localization and further upregulates SMA-Luc reporter activity. Fold-activation was determined by comparison to the transfection with empty expression vector in lane 1.

In FIG. 10A, there is the DNA construct used to generate mice expressing FLAG-tagged rat CRP2 protein in the adult cardiomyocytes. Genotyping was performed by Southern blot of mouse tail genomic DNA using probe (~1 kb) specific to the transgene confirmed by RT-PCR analysis using primers amplifying a 472 bp fragment starting from the FLAG epitope tag. In FIG. 10B, there is an increase in heart-weight to body-weight ratio of CRP2 transgenic mice. Comparison of heart-weight to body-weight ratio (HtW/BW), measured in mg/g, in age-match non-transgenic (NTg) and transgenic (Tg) mice. The ratio is significantly higher (*, p<0.05) in Tg mice after 6 months of age. Bar graph represents the compiled data of all 12 pairs of animals measured. In FIG. 10C, there is gross morphology of representative hearts from a pair of NTg and Tg littermates at 6 mo of age. In FIG. 10D, western blot analysis revealed exogenous synthesis of SMC contractile proteins in adult hearts of aMHC-CRP2 mice. Cardiac proteins from 3 pairs NTg and Tg littermates were harvested from ventricular portion of the hearts. Equal loadings of whole cell lysate (~100 mg) were subjected to SDS-PAGE and transferred to PVDF membrane. Immunoblots were carried out using protein specific antibodies. Small intestine and soleus muscle were used as positive controls for smooth (SM) and striated (SK) muscle, respectively.

In FIG. 11A, there is a schematic representation of recombinant TAT fusion protein constructs. His6, polyhistidine tag; PTD, protein transduction domain of HIV TAT protein; HA, epitope tag of influenza hemaglutinin protein. In FIG. 11B, freshly isolated neonatal rat cardiomyocytes were plated overnight then treated with recombinant TAT-CRP2 fusion protein. Whole cell lysate were harvested at various time points and Western blot analysis was performed to verify transduction of HA-epitope tagged TAT-CRP2. In FIG. 11C, immunofluorescent staining was carried out to detect coexpression of smooth muscle cell (SMC) marker genes (SMA, calponin and SM-MHC) and cardiac specific troponin T (TnT) in neonatal cardiomyocytes three days after TAT-CRP2 or TAT-βgal treatment. SMC contractile proteins were present in cardiomyocytes treated with TAT-CRP2 but not in the TAT-βgal control group. In FIG. 11D, the effect of recombinant TAT-CRP2 (left) or TAT-βgal (right) treatment on SM-MHC induction in cardiomyocyte assessed over time by semi-quantitative RT-PCR (top three panels) and Western immunoblot analysis (bottom two panels). Arrow, time at which TAT-fusion proteins were added to the media. In FIG. 11E, the effect of cycloheximide (CHX) on TAT-CRP2 induced SM-MHC mRNA levels assessed by semi-quantitative RT-PCR analysis.

In FIGS. 12A and 12B, nuclear and cytoplasmic extracts were harvested from adult hearts of αMHC-CRP2 transgenic mice overexpressing FLAG-tagged CRP2 in the cardiomyocytes. Left panels, co-immunoprecipitation was performed using ~1 mg of nuclear extracts (N.E.) and antibodies against FLAG-epitope, SRF or GATA6 (lanes 1, 2 and 3, respectively). Right panels, co-immunoprecipitation were performed using ~0.2 mg of cytoplasmic extracts (C.E.) and antibodies against FLAG-epitope, actinin or tubulin (lanes 7, 8 and 9, respectively). In lanes 4 and 10, no antibody was added in the immunoprecipitation step, serving as negative controls. In lanes 5, 6, 11 and 12, 10% of input proteins were loaded as positive controls. In FIG. 12C, pull-down analysis of protein interactions between recombinant CRP2, SRF, GATA4 or NKx2.5 and nuclear extracts from αMHC-CRP2 cardiomyocytes is presented. Bound proteins (lane 2-7) and 10% of input nuclear extracts (lane 1) were resolved on 4-20% SDS-PAGE gels and immunoblotted with antibodies against Brg1 (top panel) or Brm (bottom panel) of SWI/SNF remodeling complexes. In FIG. 12D, the second zinc finger of the CRP2 LIM domain is necessary for in vivo co-association with Brg1. Nuclear lysates of C2C12 cells co-transfected with V5-tagged wild type or deletion mutants of CRP2 were subjected to co-immunoprecipitation assays using either anti-V5 or anti-Brg1 antibody. Immune complexes were separated by 4-20% SDS-PAGE gels and immunoblotted with antibodies against V5 or Brg1. Summary of Brg1 interactions and the schematic representation of CRP2 constructs were shown on the right.

DETAILED DESCRIPTION OF THE INVENTION

I. Definitions

Figure 1:
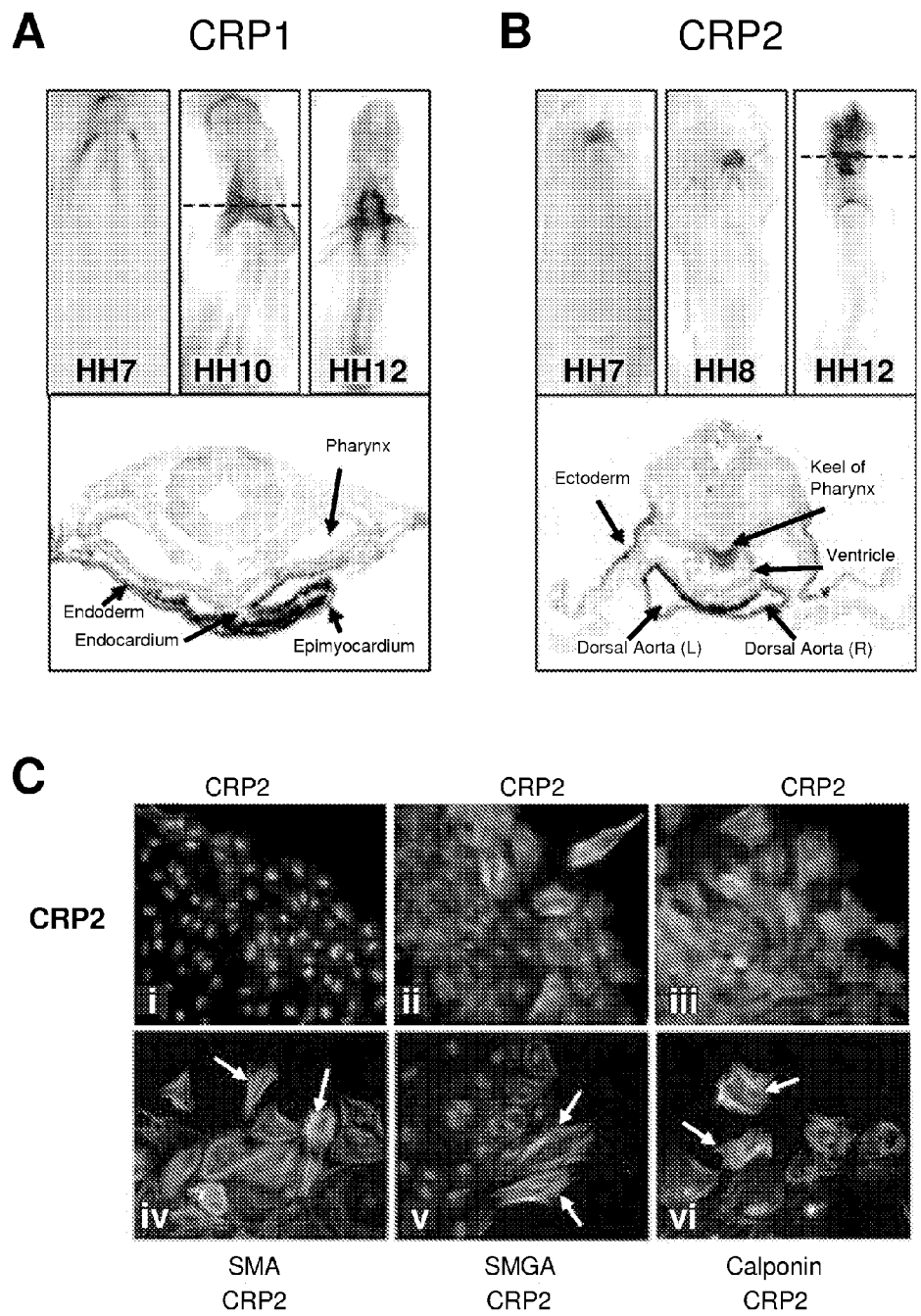
FIGS. 1A through 1C illustrate LIM-only CRP1 and CRP2 genes expressed during early chick embryonic cardiovascular development.

The term "a" or "an" as used herein in the specification may mean one or more. As used herein in the claim(s), when used in conjunction with the word "comprising", the words "a" or "an" may mean one or more than one. As used herein "another" may mean at least a second or more.

As used herein, the term "allogeneic" refers to tissue or cells derived from another subject of the same species.

As used herein, the term "autologous" refers to tissue or cells that are derived from the same subject's body.

The term "blood vessel" as used herein is defined as a vessel or canal through which blood circulates. Examples include artery, vein, and capillary.

The term "cardiovascular disease" as used herein is defined as a medical condition related to the cardiovascular (heart) or circulatory system (blood vessels). Cardiovascular disease includes, but is not limited to, diseases and/or disorders of the pericardium (i.e., pericardium), heart valves (i.e., incompetent valves, stenosed valves, rheumatic heart disease, mitral valve prolapse, aortic regurgitation), myocardium (coronary artery disease, myocardial infarction, heart failure, ischemic heart disease, angina) blood vessels (i.e., arteriosclerosis, aneurysm) or veins (i.e., varicose veins, hemorrhoids). Yet further, one skill in the art recognizes that cardiovascular diseases can result from congenital defects, genetic defects, environmental influences (i.e., dietary influences, lifestyle, stress, etc.), and other defects or influences, and combinations thereof.

The term "cardiovascular tissue" as used herein is defined as heart tissue and/or blood vessel tissue.

As used herein, the term "coronary artery disease" (CAD) refers to a type of cardiovascular disease. CAD is caused by gradual blockage of the coronary arteries. One of skill in the art realizes that in coronary artery disease, atherosclerosis (commonly referred to as "hardening of the arteries") causes thick patches of fatty tissue to form on the inside of the walls of the coronary arteries. These patches are called plaque. As the plaque thickens, the artery narrows and blood flow decreases, which results in a decrease in oxygen to the myocardium. This decrease in blood flow precipitates a series of consequences for the myocardium. For example, interruption in blood flow to the myocardium results in an "infarct" (myocardial infarction), which is commonly known as a heart attack.

As used herein, the term "damaged myocardium" refers to myocardial cells that have been exposed to ischemic conditions. These ischemic conditions may be caused by a myocardial infarction, or other cardiovascular disease or related complaint. The lack of oxygen causes the death of the cells in the surrounding area, leaving an infarct, which eventually scars.

The term "fibroblast" as used herein is defined as a connective tissue cell, which is usually a flat elongated cell with cyoplasmic processes at each end, having a flat, oval, vesicular nucleus. A skilled artisan recognizes that fibroblasts, which differentiate endogenously into chondroblasts, collagenoblasts, and osteoblasts, form the fibrous tissues in the body, tendons, aponeuroses, supporting and binding tissues of all sorts. In a specific embodiment, a fibroblast is also referred to as a fibrocyte or a desmocyte.

As used herein, the term "infarct" or "myocardial infarction (MI)" refers to an interruption in blood flow to the myocardium. Thus, one of skill in the art refers to MI as death of cardiac muscle cells resulting from inadequate blood supply.

As used herein, the term "ischemic heart disease" refers to a lack of oxygen due to inadequate perfusion or blood supply. Ischemic heart disease is a condition having diverse etiologies. One specific etiology of ischemic heart disease is the consequence of atherosclerosis of the coronary arteries.

The term "LIM domain" as used herein refers to double zinc finger-like structures that mediate protein-protein interactions and, in specific embodiments, target proteins to distinct subcellular locations and/or mediate assembly of multimeric protein complexes. In a preferred embodiment, a CRP1 and/or CRP2 polynucleotide utilized in the present invention encodes a respective CRP1 and/or CRP2 polypeptide having at least one LIM domain. In a specific embodiment, the CRP1 and/or CRP2 polypeptide comprises more than one LIM domain. In some embodiments, both LIM domains are comprised on the same molecule, and in other embodiments both LIM domains are comprised on at least two molecules. In a specific embodiment, the LIM domain comprises $CX_2CX_{17}HX_2CX_2CX_2CX_{17}$-$CX_2C$ (SEQ ID NO:16) (Michelsen et al., 1993). In other specific embodiments, it comprises $CX_2CX_{16-23}H_2CX_2CX_2\ CX_{16-21}\ CX_{2-3}(C/H/D)$ (SEQ ID NO:17) (Sadler et al., 1992).

As used herein, the term "myocardium" refers to the muscle of the heart.

As used herein, the term "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

As used herein, the term "progenitor cell" refers to a cell that is a parent cell capable of differentiating into a smooth muscle cell upon delivery to the cell of SRF, CRP, and GATA. One of skill in the art realizes that a progenitor cell is an ancestor cell to progeny descendant cells.

The term "smooth muscle cell" as used herein is defined as a cell comprising detectable levels of expression of SM α-actin, calponin, h-caldesmon, and/or SM22α.

The term "smooth muscle polynucleotide" as used herein refers to a polynucleotide that is primarily expressed in smooth muscle cells. Although expression of the polynucleotide may be in other cells in some embodiments, the majority of expression of the polynucleotide is in smooth muscle cells.

As used herein, the term "stem cells" refers to "undifferentiated" cells capable of proliferation, self-maintenance, production of differentiated cells and/or regeneration of stem cells. In preferred embodiments of the present invention, a stem cell is capable of differentiating into a differentiated cell, such as a smooth muscle cell.

The term "substantially concomitantly" as used herein refers to transformation of a cell with at least one polynucleotide comprising SRF, a CRP, and/or a GATA, wherein the vector or vectors comprising the polynucleotide(s) enter the recipient cell during the same cell cycle.

The term "therapeutically effective amount" as used herein refers to an amount that results in an improvement or remediation of the disease, disorder, or symptoms of the disease or condition.

The term "treating" and "treatment" as used herein refers to administering to a subject a therapeutically effective amount of a the composition so that the subject has an improvement in the disease. The improvement is any improvement or remediation of the symptoms. The improvement is an observable or measurable improvement. Thus, one of skill in the art realizes that a treatment may improve the disease condition, but may not be a complete cure for the disease.

As used herein, the term "xenogeneic" refers to cells that are derived from different species.

II. The Present Invention

The present invention regards directed cell differentiation of a particular cell type, such as a fibroblast, into a cell of vascular smooth muscle and, in a preferred embodiment, the smooth muscle cell and/or a tissue comprising the same is used for cardiac disease therapy.

Human heart failure is the leading cause of combined morbidity and mortality in the United States and other developed industrial nations. It remains an incurable disease process with an estimated five-year mortality of 30-50% for the patients with advanced disease. Although great advances have been made in the treatment for failing heart, the understanding of the molecular mechanism leading to heart failure is still limited.

CRP2, an arterial smooth muscle-restricted dual LIM-only protein, associates with cytoskeleton-associated proteins, such as α-actinin and zyxin. In a specific embodiment of the present invention, CRP2 functions as a molecular co-adaptor, wherein the zinc finger LIM domains serve as a protein-protein interaction interface that facilitates formation of transcription factor complexes. Even though CRP2 does not directly bind to DNA, in transient cotransfection assays in CV-1 fibroblasts the present inventors observed over a thousand fold transactivation of both smooth muscle α-actin (SMA) and SM22α promoters in combination with the smooth muscle enriched MADS-box factor SRF and the zinc-finger protein GATA6. A highly related zinc-finger protein GATA4 substitutes for GATA6, in some embodiments. Through mutation analysis, the N-terminal LIM domain of CRP2 was mapped and determined necessary for the enhanced co-activation of SMA and SM22α. In GST pull-down experiments, CRP2 interacts with SRF and with GATA factors. To determine Whether the proposed transcription complex can promote endogenous gene expression, pluripotent murine fibroblast 10T1/2 cells were co-transfected with SRF, GATA6, and CRP2 expression vectors. Western blotting analysis of cell lysate from cotransfected 10T1/2 cells revealed induction of early SMC target genes, SMA, h-caldesmon and SM22α. Transcripts of the late SMC marker calponin were induced, but smooth muscle myosin heavy chain was not at detectable levels. In contrast, sarcomeric α-actin, which is restricted to striated muscle lineages, was not activated. Previously, immunofluorescence analysis has demonstrated CRP2 co-localization with cytoplasmic F-actin. It was determined that leptomycin B, a specific inhibitor of nuclear export signal-dependent nuclear exclusion, induced CRP2 accumulation in the nucleus. In addition, treatment with p160-Rho kinase inhibitor Y-27632, which causes cytoskeletal rearrangement through a complex signaling pathway, facilitated CRP2 nuclear localization and further up-regulated SMA and SM22 α promoter activities. Thus, the present invention is a novel mechanism for activation of early smooth muscle specific genes through regulated cellular redistribution, and this combination of transcription components results in the conversion of a cell, such as a fibroblast and/or stem cell into a vascular smooth muscle lineage that in some embodiments is useful for the repair of damaged cardiovascular organs and blood vessels.

In specific embodiments of the present invention, a progenitor cell is differentiated into a smooth muscle cell following introduction of SRF, a CRP, and a GATA into the progenitor cell. In a specific embodiment, a CRP is CRP1 or CRP2. In another embodiment, a GATA is GATA-2, GATA-4, or GATA-6. In a further embodiment, the generated smooth muscle cell is cultured to provide a plurality of smooth muscle cells. In still further embodiments, at least one smooth muscle cell from the culture is utilized in generating a tissue. In more embodiments, the tissue forms a structure for therapy for cardiac disease, such as a blood vessel or heart component.

A skilled artisan recognizes a variety of methods and compositions are known in the art to generate tissues for cardiac disease therapy (see, for example, Niklason et al., 1999). For example, in some embodiments, the tissue development comprises the quaking polynucleotide to facilitate blood vessel development (Noveroske et al., 2002). In other embodiments, the generated smooth muscle cells are cultured for approximately eight weeks, and in preferred embodiments results in an engineered vessel wall with the smooth muscle cells organized into a highly lamellar structure with cells separated by alternating layers of collagen fibrils (Niklason et al., 2001). Also, it is known that bone marrow from adult humans comprises endothelial precursors with phenotypic and functional characteristics of embryonic hemangioblasts, and that these can be used to facilitate induction of new blood vessel formation (Kocher et al., 2001).

In other embodiments of the present invention, a smooth muscle cell is generated by methods described herein, and the cell is utilized for smooth muscle repair in a region of the body other than cardiac tissue, for example, the gut, and so forth III. Treatment of Cardiovascular Disease Embodiments of the present invention include the methods of delivering to a subject a smooth muscle cell, generated by introduction of SRF, a CRP, and a GATA to a non-smooth muscle cell, or a pharmaceutical composition comprising the same to treat cardiovascular disease.

Cardiovascular diseases and/or disorders include, but are not limited to, diseases and/or disorders of the pericardium (i.e., pericardium), heart valves (i.e., incompetent valves, stenosed valves, Rheumatic heart disease, mitral valve prolapse, aortic regurgitation), myocardium (coronary artery disease, myocardial infarction, heart failure, ischemic heart disease, angina) blood vessels (i.e., arteriosclerosis, aneurysm) or veins (i.e., varicose veins, hemorrhoids). In specific embodiments, the cardiovascular disease includes, but is not limited to, coronary artery diseases (i.e., arteriosclerosis, atherosclerosis, and other diseases of the arteries, arterioles and capillaries or related complaint), myocardial infarction and ischemic heart disease.

Accordingly, the invention involves the administration of smooth muscle cells generated by methods described herein or tissues derived therefrom or a pharmaceutical composition comprising same as a treatment or prevention of any one or more of these conditions or other conditions involving weakness and/or damage in the heart. It is envisioned that one of skill in the art will know the most advantageous routes of administration depending upon the disease. In specific embodiments, it is contemplated that the smooth muscle cells or pharmaceutical composition comprising same can be administered via injection, which includes, but is not limited to subcutaneous, intravenous, intraarterial, intramuscular, intraperitoneal, intramyocaridal, transendocardial, transepicardial, intranasal and intrathecal.

Yet further, it is envisioned that the smooth muscle cells or pharmaceutical composition of the present invention can be administered to the subject in an injectable formulation containing any compatible carrier, such as various vehicles, adjuvants, additives, and diluents. Yet further, the stem cells or pharmaceutical composition can be administered parenterally to the subject in the form of slow-release subcutaneous implants or targeted delivery systems such as monoclonal antibodies, iontophoretic, polymer matrices, liposomes, and microspheres.

Treatment regimens may vary as well, and often depend on the cardiovascular disease or disorder, disease progression, and health and age of the subject. Obviously, certain types of cardiovascular disease will require more aggressive treatment, while at the same time, certain patients cannot tolerate more taxing protocols. The clinician will be best suited to make such decisions based on the known efficacy and toxicity (if any) of the therapeutic formulations.

Suitable regimes for initial administration and further doses or for sequential administrations also are variable, and may include an initial administration followed by subsequent administrations; but nonetheless, may be ascertained by the clinician.

For example, the smooth muscle cells or tissues derived therefrom or the pharmaceutical composition thereof can be administered initially, and thereafter maintained by further administration. For instance, a composition of the invention can be administered in one type of composition and thereafter further administered in a different or the same type of composition. For example, a composition of the invention can be administered by intravenous injection to bring blood levels to a suitable level. The subject's levels are then maintained by a subcutaneous implant form, although other forms of administration, dependent upon the subject's condition, can be used.

As used herein the term "effective amount" is defined as an amount of the smooth muscle cells or pharmaceutical composition thereof that will repair damaged myocardium, regenerate cardiomyocytes, regenerate vascular cells, provide structural stability to an injured myocardium or provide at least partially restored functionality to an injured myocardium. Thus, an effective amount is an amount sufficient to detectably and repeatedly ameliorate, reduce, minimize or limit the extent of the disease or its symptoms.

The precise determination of what would be considered an effective dose may be based on factors individual to each subject, including their size, age, size of the infarct, and amount of time since damage. Therefore, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention. Of course, for any composition to be administered to an animal or human, and for any particular method of administration, it is preferred to determine the toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. Furthermore, the time for sequential administrations can be ascertained without undue experimentation.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time.

In further embodiments, the smooth muscle cells or tissues derived therefrom are administered to a subject suffering from myocardial infarction. It is contemplated that the differentiated smooth muscle cells can alleviate the symptoms associated with myocardial infarction. For example, the injected cells migrate to the infarcted myocardium. The migrated stem cells differentiate into myocytes. The myocytes them assemble into myocardium tissue resulting in repair or regeneration of the infarcted myocardium.

Further embodiments of the present invention involve a method of targeting injured myocardium by delivering to a subject the differentiated smooth muscle cells, as described herein, wherein the cells migrate or hone and attach to the injured myocardium. The smooth muscle cells are administered intravenously to the subject. Thus, the smooth muscle cells maneuver the systemic circulation and migrate or target or home to the damaged or injured myocardium. Once the smooth muscle cells have migrated to the damaged myocardium, the smooth muscle cells repair the damage myocardium.

In further embodiments, the present invention involves a method of repairing injured coronary vessels by administering to the subject an effective amount of smooth muscle cells generated by methods described herein, such that the amount results in regeneration of coronary vascular cells to repair the coronary vasculature.

Another embodiment is a method of generating smooth muscle cells from non-smooth muscle cells. The smooth muscle cells can be generated in vivo or in vitro. In a specific embodiment, the smooth muscle cells are generated in vitro. In generating smooth muscle cells, non-smooth muscle cells are obtained from a source. The source can be mammalian and can provide, for example, a fibroblast. Once the non-smooth muscle cells are obtained, they are administered SRF, a CRP, and a GATA, and then they are cultured in vitro so that a plurality of cells is generated. It is envisioned that the non-smooth muscle cells can differentiate into smooth muscle cells without the addition of any factors other than SRF, a CRP, and a GATA.

Yet further, it is also contemplated that additional transcription factor(s) that are useful for cardiac development may be useful in the present invention, for example, Nkx2.5, can be administered to the non-smooth muscle cells. The transcription factor can be administered directly to the cultured stem cells. Yet further, the transcription factor can be administered via an expression vector that expresses the transcription factor. Development of expression vectors are well known and used in the art, for example Manniatis et al. (1982). Once the expression vector is generated, it can be delivered to the cells via standard transfection protocols, which are well-known and used in the art. These standard transfection protocols include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Yet further, it is envisioned that the non-smooth muscle cells are obtained from an autologous source. The autologous source can be tissue that is obtained from a tissue biopsy. The cells are proliferated in vitro to generate an abundance of the autologous cells. After a suitable number of cells have been proliferated, the SRF, CRP, and GATA are introduced to the autologous cells to generate smooth muscle cells and, in further embodiments, are administered to the subject, such as via an intravenous injection. In other embodiments the autologous source smooth muscle cells are administered to an individual as a tissue, such as a cardiac tissue, including a vessel.

It is well known by those of skill in the art that the use of autologous non-smooth muscle cells will reduce and/or eliminate an immune reaction that may occur if allogeneic or xenogeneic non-smooth muscle cells are used. Allogeneic or xenogeneic cells are initially recognized by the subject's immune system through antigenic determinants expressed on the surface of the cells. The predominant antigens recognized as "non-self" are major histocompatibility complex class I and class II antigens (MHC class I and class II). However, if non-autologous cells are used, one of skill in the art is aware of the various procedures that may be used to reduce the immune reaction to the stem cells.

One such procedure that is routinely used to inhibit rejection of transplanted cells by the immune system of the subject is the administration of drugs that suppress the function of the immune system. While drugs, such as cyclophosphamide and cyclosporin, effectively inhibit the actions of the immune system, and thus allow acceptance of the cells, their use can cause generalized, non-specific immunosuppression in the which leaves the subject susceptible to other disorders such as infection. Additionally, administration of immunosuppressive drugs is often accompanied by other serious side effects such as renal failure hypertension.

Another procedure that is readily available to those of skill in the art is to genetically modify the cells. Such genetic modification includes, for example altering at least one of the surface antigens to decrease the recognition of non-self, for example see U.S. Pat. No. 5,679,340, which is incorporated herein by reference. Further modifications can also include packaging of the cells in a liposome, a micelle or other vehicle to mask the cells from the immune system. Thus, one of skill in the art is cognizant of various procedures and techniques that are available to alter a composition so that it is not recognized as "non-self", thus decreasing the immune response to allogeneic or xenogeneic cell transplantation.

IV. Combined Cardiac Disease Treatments

In order to increase the effectiveness of the smooth muscle cells generated by methods described herein, it may be desirable to combine these compositions and methods of the invention with a known agent effective in the treatment of cardiac disease or disorder. In some embodiments, it is contemplated that a conventional therapy or agent, including but not limited to, a pharmacological therapeutic agent, a surgical therapeutic agent (e.g., a surgical procedure) or a combination thereof, may be combined with the smooth muscle cells of the present invention or a tissue derived therefrom. In a non-limiting example, a therapeutic benefit comprises repair of myocardium or vascular tissue or reduced restenosis following vascular or cardiovascular intervention, such as occurs during a medical or surgical procedure.

This process may involve contacting the cell(s) with an agent(s) and the smooth muscle cells of the present invention, or a tissue derived therefrom, at the same time or within a period of time wherein separate administration of the smooth muscle cells and an agent to a cell, tissue or organism produces a desired therapeutic benefit. The terms "contacted" and "exposed," when applied to a cell, tissue or organism, are used herein to describe the process by which the smooth muscle cells and/or therapeutic agent(s) are delivered to a target cell, tissue or organism or are placed in direct juxtaposition with the target cell, tissue or organism. The cell, tissue or organism may be contacted (e.g., by administration) with a single composition or pharmacological formulation that comprises both smooth muscle cells and one or more agents, or by contacting the cell with two or more distinct compositions or formulations, wherein one composition includes the smooth muscle cells and the other includes one or more agents.

The treatment may precede, be co-current with and/or follow the other agent(s) by intervals ranging from minutes to weeks. In embodiments where the stem cells, and other agent(s) are applied separately to a cell, tissue or organism, one would generally ensure that a significant period of time did not expire between the time of each delivery, such that the stem cells and agent(s) would still be able to exert an advantageously combined effect on the cell, tissue or organism. For example, in such instances, it is contemplated that one may contact the cell, tissue or organism with two, three, four or more modalities substantially simultaneously (i.e. within less than about a minute) as the smooth muscle cells or tissue derived therefrom. In other aspects, one or more agents may be administered within of from substantially simultaneously, about minutes to hours to days to weeks and any range derivable therein, prior to and/or after administering the smooth cells or a tissue derived therefrom.

Administration of the smooth muscle cell composition to a cell, tissue or organism may follow general protocols for the administration of vascular or cardiovascular therapeutics, taking into account the toxicity, if any. It is expected that the treatment cycles would be repeated as necessary. In particular embodiments, it is contemplated that various additional agents may be applied in any combination with the present invention.

A. Pharmacological Therapeutic Agents

Pharmacological therapeutic agents and methods of administration, dosages, etc., are well-known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, or a combination thereof.

B. Surgical Therapeutic Agents

In certain aspects, a therapeutic agent may comprise a surgery of some type, which includes, for example, preventative, diagnostic or staging curative and/or palliative surgery. Surgery, and in particular, a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

Further treatment of the area of surgery may be accomplished by perfusion, direct injection, systemic injection or local application of the area with at least one additional therapeutic agent (e.g., the smooth muscle cells of the present invention and/or a tissue derived therefrom, a pharmacological therapeutic agent, and so forth), as would be known to one of skill in the art or described herein.

V. Kits

Any of the compositions described herein may be comprised in a kit. In a non-limiting example, the stem cells, lipid, and/or additional agent, may be comprised in a kit. The kits will thus comprise, in suitable container means, the stem cells and a lipid, and/or an additional agent of the present invention.

The kits may comprise a suitably aliquoted stem cells, lipid and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the stem cells or the pharmacological composition of the present invention, lipid, additional agent, and any other reagent containers in close confinement for commercial sale. Such containers may include injection or blow-molded plastic containers into which the desired vials are retained.

Therapeutic kits of the present invention are kits comprising the stem cells. Such kits will generally contain, in suitable container means, a pharmaceutically acceptable formulation of the stem cells. The kit may have a single container means, and/or it may have distinct container means for each compound.

When the components of the kit are provided in one and/or more liquid solutions, the liquid solution is an aqueous solution, with a sterile aqueous solution being particularly preferred. The stem cell compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the stem cells are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate the stem cell composition within the body of an animal. Such an instrument may be a syringe, pipette, forceps, and/or any such medically approved delivery vehicle.

VI. Definitions and Techniques Affecting Gene Products and Genes

A. SRF, CRP, and/or GATA Gene Products and Genes

In this patent, the terms "CRP gene product" and "CRP" refer to proteins and polypeptides having amino acid sequences that are substantially identical to the native CRP amino acid sequences (or RNA, if applicable) or that are biologically active, in that they are capable of performing functional activities similar to an endogenous CRP and/or cross-reacting with anti-CRP antibody raised against CRP. In analogous embodiments, "SRF gene product," "SRF," "GATA gene product," and "GATA" are referred to herein. In a specific embodiment, a function of CRP is to be involved in protein-protein interactions, and other embodiments include associating with adhesion plaques and filamentous actin, interact with α-actinin, interact with zyxin, regulate the stability and structure of adhesion complexes, and a combination thereof. In other specific embodiments, SRF functions to integrate intracellular signals, assist as a docking surface for cofactor binding, and influence gene expression. The function of GATA is to act as a transcription factor.

An example of a SRF polypeptide sequence, followed by its National Center for Biotechnology's GenBank database Accession No. includes a SRF polypeptide comprising SEQ ID NO:2 (NP_003122), or a functionally similar fragment thereof. Examples of CRP1 polypeptides include SEQ ID NO:3 (NP_004069) or SEQ ID NO:4 (P47875). Some examples of CRP2 polypeptides are SEQ ID NO:7 (NP_001312); and SEQ ID NO:9 (AAC51755). Some examples of GATA2 polypeptides include SEQ ID NO:12 (NP_002041) and SEQ ID NO:14 (AAA35868).

The term "SRF gene product, CRP gene product, or GATA gene product" also include analogs of the respective molecules that exhibit at least some biological activity in common with their native counterparts. Such analogs include, but are not limited to, truncated polypeptides and polypeptides having fewer amino acids than the native polypeptide. Furthermore, those skilled in the art of mutagenesis will appreciate that homologs to the mouse SRF, CRP, or GATA polynucleotide, including human homologs, which homologs are as yet undisclosed or undiscovered, may be used in the methods and compositions disclosed herein.

The term "SRF gene" "SRF polynucleotide" or "SRF nucleic acid" refers to any DNA sequence that is substantially identical to a DNA sequence encoding an SRF gene product as defined above. Similar terms for CRP and GATA are within the scope of the present invention. The term also refers to RNA or antisense sequences compatible with such DNA sequences. An "SRF gene or SRF polynucleotide" may also comprise any combination of associated control sequences. In a specific embodiment of the present invention, a SRF polynucleotide of SEQ ID NO:3. (NM_003131) or a functionally similar fragment thereof, is utilized. An example of a CRP1 polynucleotide comprises SEQ ID NO:5 (NM_004078). Examples of CRP2 polynucleotides include SEQ ID NO:6 (U95017); SEQ ID NO:8 (NM_001321); SEQ ID NO:10 (U95018); and SEQ ID NO:11 (U95017). Examples of GATA2 polynucleotides include SEQ ID NO: 13 (NM_002050) and SEQ ID NO:15 (M68891).

Thus, nucleic acid compositions encoding SRF, CRP, and/or GATA are herein provided and are also available to a skilled artisan at accessible databases, including the National Center for Biotechnology Information's GenBank database and/or commercially available databases, such as from Celera Genomics, Inc. (Rockville, Md.). Also included are splice variants that encode different forms of the protein, if applicable. The nucleic acid sequences may be naturally occurring or synthetic.

As used herein, the terms "SRF, CRP, and/or GATA nucleic acid sequence," "SRF, CRP, and/or GATA polynucleotide," and "SRF, CRP, and/or GATA gene" refer to nucleic acids provided herein, homologs thereof, and sequences having substantial similarity and function, respectively. A skilled artisan recognizes that the sequences are within the scope of the present invention if they encode a product which, in conjunction with at least one of the other three gene products, facilitates differentiation of a fibroblast into a smooth muscle cell, provides cardiac disease therapy, and furthermore knows how to obtain such sequences, as is standard in the art.

The term "substantially identical", when used to define either a SRF, CRP, and/or GATA amino acid sequence or SRF, CRP, and/or GATA polynucleotide sequence, means that a particular subject sequence, for example, a mutant sequence, varies from the sequence of natural SRF, CRP, and/or GATA, respectively, by one or more substitutions, deletions, or additions, the net effect of which is to retain at least some biological activity of the SRF, CRP, and/or GATA protein, respectively. Alternatively, DNA analog sequences are "substantially identical" to specific DNA sequences disclosed herein if: (a) the DNA analog sequence is derived from coding regions of the natural SRF, CRP, and/or GATA gene, respectively; or (b) the DNA analog sequence is capable of hybridization of DNA sequences of (a) under moderately stringent conditions and which encode biologically active SRF, CRP, and/or GATA, respectively; or (c) DNA sequences which are degenerative as a result of the genetic code to the DNA analog sequences defined in (a) or (b). Substantially identical analog proteins will be greater than about 80% similar to the corresponding sequence of the native protein. Sequences having lesser degrees of similarity but comparable biological activity are considered to be equivalents. In determining polynucleotide sequences, all subject polynucleotide sequences capable of encoding substantially similar amino acid sequences are considered to be substantially similar to a reference polynucleotide sequence, regardless of differences in codon sequence.

1. Percent Similarity

Percent similarity may be determined, for example, by comparing sequence information using the GAP computer program, available from the University of Wisconsin Geneticist Computer Group. The GAP program utilizes the alignment method of Needleman et al., 1970, as revised by Smith et al., 1981. Briefly, the GAP program defines similarity as the number of aligned symbols (i.e. nucleotides or amino acids) which are similar, divided by the total number of symbols in the shorter of the two sequences. The preferred default parameters for the GAP program include (1) a unitary comparison matrix (containing a value of 1 for identities and 0 for non-identities) of nucleotides and the weighted comparison matrix of Gribskov et al., 1986, (2) a penalty of 3.0 for each gap and an additional 0.01 penalty for each symbol and each gap; and (3) no penalty for end gaps.

2. Polynucleotide Sequences

In certain embodiments, the invention concerns the use of SRF, CRP, and/or GATA genes and gene products, such as the SRF, CRP, and/or GATA that includes a sequence which is essentially that of the known SRF, CRP, and/or GATA gene, or the corresponding protein, respectively. The term "a sequence essentially as SRF, CRP, and/or GATA" means that the sequence substantially corresponds to a portion of the SRF, CRP, and/or GATA gene, respectively, and has relatively few bases or amino acids (whether DNA or protein) that are not identical to those of SRF, CRP, and/or GATA (or a biologically functional equivalent thereof, when referring to proteins), respectively. The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids which are identical or functionally equivalent to the amino acids of SRF, CRP, and/or GATA, respectively, will be sequences which are "essentially the same".

SRF, CRP, and/or GATA genes that have functionally equivalent codons, respectively, are also covered by the invention. The term "functionally equivalent codon" is used herein to refer to codons that encode the same amino acid, such as the six codons for arginine or serine, and also refers to codons that encode biologically equivalent amino acids (Table 1).

TABLE 1

FUNCTIONALLY EQUIVALENT CODONS.

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glutamic Acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCU |

TABLE 1-continued

FUNCTIONALLY EQUIVALENT CODONS.

| Amino Acids | | | Codons |
|---|---|---|---|
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and polynucleotide sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to polynucleotide sequences which may, for example, include various non-coding sequences flanking either of the 5' or 3' portions of the coding region or may include various internal sequences, i.e., introns, which are known to occur within genes.

In certain embodiments, the invention concerns the use of truncated SRF, CRP, and/or GATA genes or polynucleotide sequences that encode a SRF, CRP, and/or GATA polypeptide, respectively, with less amino acids than native SRF, CRP, and/or GATA, respectively. The present invention also encompasses the use of DNA segments that are complementary, or essentially complementary, to the sequences set forth in the specification. Polynucleotide sequences that are "complementary" are those which are capable of base-pairing according to the standard Watson-Crick complementarily rules. As used herein, the term "complementary sequences" means polynucleotide sequences which are substantially complementary, as may be assessed by the same nucleotide comparison set forth above, or as defined as being capable of hybridizing to the polynucleotide segment in question under relatively stringent conditions such as those described herein.

3. Biologically Functional Equivalents

As mentioned above, modification and changes may be made in the structure of SRF, CRP, and/or GATA and still obtain a molecule having like or otherwise desirable characteristics, respectively. For example, certain amino acids may be substituted for other amino acids in a protein structure without appreciable loss of activity for upregulating expression of smooth muscle-specific polynucleotides. Since it is the interactive capacity and nature of a protein that defines that protein's biological functional activity, certain amino acid sequence substitutions and/or deletions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of the SRF, CRP, and/or GATA proteins or peptides (or underlying DNA) without appreciable loss of their biological utility or activity, respectively. Included in such changes are truncated SRF, CRP, and/or GATA polypeptides and SRF, CRP, and/or GATA polypeptides having less amino acid residues than native SRF, CRP, and/or GATA, respectively.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where any changes in SRF, CRP, and/or GATA that render the respective polypeptide incapable of preventing or delaying entry into mitosis following DNA damage would result in a loss of utility of the resulting peptide for the present invention.

Amino acid substitutions, such as those that might be employed in modifying SRF, CRP, and/or GATA, respectively, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (□0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

4. Sequence Modification Techniques

Modifications to the SRF, CRP, and/or GATA peptides may be carried out using techniques such as site-directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector that exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes at least the SRF, CRP, and/or GATA gene. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful SRF, CRP, and/or GATA and is not meant to be limiting as there are other ways in which sequence variants of these peptides may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

5. Antisense Constructs

In some cases, a gene is essential to the life of the cell, wherein its removal, such as by homologous replacement, results in the death of the cell. In other cases, a gene may have aberrant functions that cannot be overcome by replacement gene therapy, even where the "wild-type" molecule is expressed in amounts in excess of the mutant polypeptide. Antisense treatments are one way of addressing these situations. Antisense technology also may be used to "knock-out" function of SRF, CRP, and/or GATA in the development of cell lines or transgenic mice for research, diagnostic and screening purposes.

Antisense methodology takes advantage of the fact that nucleic acids tend to pair with "complementary" sequences. By complementary, it is meant that polynucleotides are those that are capable of base-pairing according to the standard Watson-Crick complementarily rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarily to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences that are completely complementary will be sequences which are entirely complementary throughout their entire length and have no base mismatches. Other sequences with lower degrees of homology also are contemplated. For example, an antisense construct that has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

6. RNA Interference

RNA interference (RNAi) is the process of sequence-specific, post-transcriptional gene silencing in animals and plants, initiated by double-stranded RNA (dsRNA) that is homologous in sequence to the silenced gene. Elbashir et al. (2001a) demonstrated that 21- and 22-nt RNA fragments are the sequence-specific mediators of RNAi. In a specific embodiment, the short interfering RNAs (siRNAs) are generated by an RNase III-like processing reaction from long dsRNA. Chemically synthesized siRNA duplexes with overhanging 3' ends mediate efficient target RNA cleavage in the lysate, and the cleavage site is located near the center of the region spanned by the guiding siRNA. Furthermore, the direction of dsRNA processing determines whether sense or antisense target RNA can be cleaved by the siRNA-protein complex. Also, Elbashir et al. (2001b) showed that 21-nucleotide siRNA duplexes specifically suppress expression of endogenous and heterologous genes in different mammalian cell lines, including human embryonic kidney (293) and HeLa cells.

Therefore, a skilled artisan recognizes that 21-nucleotide siRNA duplexes provide an effective tool for studying gene function in mammalian cells and are useful as gene-specific therapeutics.

7. Synthetic Polypeptides

The present invention also describes SRF, CRP, and/or GATA proteins and related peptides for use in various embodiments of the present invention. The SRF, CRP, and/or GATA polypeptide may have fewer amino acids than native SRF, CRP, and/or GATA, respectively. Relatively small peptides can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

8. Other Structural Equivalents

In addition to the SRF, CRP, and/or GATA peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

B. Expression Vectors

In certain aspects of the present invention it may be necessary to express the SRF, CRP, and/or GATA proteins and/or polypeptides. Throughout this application, the term "expression construct" is meant to include any type of genetic construct containing a polynucleotide coding for a gene product in which part or all of the polynucleotide encoding sequence is capable of being transcribed. The transcript may be translated into a protein, but it need not be. Thus, in certain embodiments, expression includes both transcription of a SRF, CRP, and/or GATA polynucleotide, respectively, and translation of the respective SRF, CRP, and/or GATA mRNA into an SRF, CRP, and/or GATA protein or polypeptide product, respectively. In other embodiments, expression only includes transcription of the polynucleotide encoding an SRF, CRP, and/or GATA or its complement. In some embodiments, the SRF, CRP, and GATA sequences are comprised on three or more separate vectors. In other embodiments, the SRF, CRP, and GATA sequences are comprised on one or two vectors.

A skilled artisan recognizes that if more than one vector is utilized, it is preferential to have nonidentical means, such as markers, to monitor uptake of the vector. Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art Examples of some markers include ampicillin, neomycin, kanamycin, tetracycline, and β-galactosidase.

In order for the construct to effect expression of at least a SRF, CRP, and/or GATA transcript, the polynucleotide encoding the SRF, CRP, and/or GATA polynucleotide, respectively, will be under the transcriptional control of a promoter. A "promoter" refers to a DNA sequence recognized by the synthetic machinery of the host cell, or introduced synthetic machinery, that is required to initiate the specific transcription of a gene. The phrase "under transcriptional control" means that the promoter is in the correct location in relation to the polynucleotide to control RNA polymerase initiation and expression of the polynucleotide. In specific embodiments, the promoter comprises a SRE or CArG box, an example of which is provided in SEQ ID NO:1. In a specific embodiment, the promoter is SM22α promoter or SMA promoter In a preferred embodiment the promoter is a synthetic myogenic promoter and hGH 3' untranslated region is in the 3' untranslated region. In a specific embodiment of the present invention there is utilized a synthetic promoter, termed SPc5-12 (Li et al., 1999) (SEQ ID NO:16), which contains a proximal serum response element (SRE) from skeletal α-actin, multiple MEF-2 sites, MEF-1 sites, and TEF-1 binding sites, and greatly exceeds the transcriptional potencies of natural myogenic promoters. Other elements, including trans-acting factor binding sites and enhancers may be used in accordance with this embodiment of the invention. In an alternative embodiment, a natural myogenic promoter is utilized, and a skilled artisan is aware how to obtain such promoter sequences from databases including the National Center for Biotechnology Information (NCBI) GenBank database.

The term promoter will be used herein to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a SRF, CRP, and/or GATA polynucleotide, respectively, is not believed to be critical, so long as it is capable of expressing the polynucleotide in the targeted cell at sufficient levels. Thus, where a human cell is targeted, it is preferable to position the polynucleotide-coding region adjacent to and under the control of a promoter that is capable of being expressed in a human cell. Generally speaking, such a promoter might include either a human or viral promoter. However, in specific embodiments, the promoter is operable in fibroblasts, stem cells, smooth muscle cells, and/or a combination thereof.

In various embodiments, the human cytomegalovirus (CMV) immediate early gene promoter, the SV40 early promoter and the Rous sarcoma virus long terminal repeat can be used to obtain high-level expression of the SRF, CRP, and/or GATA polynucleotide(s). The use of other viral or mammalian cellular or bacterial phage promoters that are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter that is active in muscle cells will permit tissue-specific expression of SRF, CRP, and/or GATA polynucleotides, respectively. Table 2 lists several elements/promoters that may be employed, in the context of the present invention, to regulate the expression of SRF, CRP, and/or GATA constructs. This list is not intended to be exhaustive of all the possible elements involved in the promotion of SRF, CRP, and/or GATA expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally, any promoter/enhancer combination (as per the Eukaryotic Promoter Data Base EPDB) could also be used to drive expression of a SRF, CRP, and/or GATA construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

TABLE 2

| ENHANCER |
| --- |
| Immunoglobulin Heavy Chain |
| Immunoglobulin Light Chain |
| T-Cell Receptor |
| HLA DQ a and DQ β |
| β-Interferon |
| Interleukin-2 |
| Interleukin-2 Receptor |
| MHC Class II 5 |
| MHC Class II HLA-DRa |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| α1-Antitrypsin |

TABLE 2-continued

ENHANCER

H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus Further, selection of a promoter that is regulated in response to specific physiologic signals can permit inducible expression of the SRF, CRP, and/or GATA constructs, respectively. For example, with the polynucleotide under the control of the human PAI-1 promoter, expression is inducible by tumor necrosis factor. Table 3 illustrates several promoter/inducer combinations:

TABLE 3

| Element | Inducer |
| --- | --- |
| MT II Phorbol Ester (TFA) | Heavy metals |
| MMTV (mouse mammary tumor virus) | Glucocorticoids |
| β-Interferon | Poly(rI)XPoly(rc) |
| Adenovirus 5 E2 | Ela |
| c-jun | Phorbol Ester (TPA), H2O2 |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease |
| GRP78 Gene | A23187 |
| a-2-Macroglobulin | IL-6 |
| Vimentin | Serum |
| MHC Class I Gene H-2 kB | Interferon |
| HSP70 Ela, SV40 Large T Antigen | Phorbol Ester-TPA |
| Proliferin | |
| Tumor Necrosis Factor | FMA |
| Thyroid Stimulating Hormone a Gene | Thyroid Hormone |

In certain embodiments of the invention, the delivery of an expression vector in a cell may be identified in vitro or in vivo by including a marker in the expression vector. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed along with the polynucleotide encoding SRF, CRP, and/or GATA. Further examples of selectable markers are well known to one of skill in the art.

One typically will include a polyadenylation signal to effect proper polyadenylation of the transcript. The nature of the polyadenylation signal is not believed to be crucial to the successful practice of the invention, and any such sequence may be employed. The inventor has employed the SV40 polyadenylation signal in that it was convenient and known to function well in the target cells employed. Also contemplated as an element of the expression construct is a terminator. These elements can serve to enhance message levels and to minimize read through from the construct into other sequences.

The expression construct may comprise a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes, expression vectors need not be viral but, instead, may be any plasmid, cosmid or phage construct that is capable of supporting expression of encoded genes in mammalian cells, such as pUC or Bluescript™ plasmid series.

C. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration, or which may affect the function of various other molecules. In one approach, one would generate a three-dimensional structure for SRF, CRP, and/or GATA, respectively or a fragment thereof. This could be accomplished by x-ray crystallography, computer modeling or by a combination of both approaches. An alternative approach, "alanine scan" involves the random replacement of residues throughout molecule with alanine, and the resulting affect on function determined.

It also is possible to isolate a SRF, CRP, and/or GATA specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved SRF, CRP, and/or GATA activity or which act as stimulators, inhibitors, agonists, antagonists or SRF, CRP, and/or GATA or molecules affected by SRF, CRP, and/or GATA function. By use of cloned SRF, CRP, and/or GATA sequences, sufficient amounts of SRF, CRP, and/or GATA, respectively, can be produced to perform crystallographic studies. In addition, knowledge of the polypeptide sequences permits computer employed predictions of structure-function relationships.

The present invention also contemplates the use of SRF, CRP, and/or GATA, respectively, and active fragments, and nucleic acids coding therefor, in the screening of compounds for activity in either stimulating SRF, CRP, and/or GATA activity, overcoming the lack of SRF, CRP, and/or GATA or blocking the effect of a mutant SRF, CRP, and/or GATA molecule.

The present invention also encompasses the use of various animal models. By developing or isolating mutant cells lines that fail to express normal SRF, CRP, and/or GATA, one can, in some embodiments, generate cardiac disease models in mice that will be highly predictive of same in humans and other mammals. Transgenic animals that lack a wild-type SRF, CRP, and/or GATA may be utilized as models for cardiac disease development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

D. In Vivo Delivery and Treatment Protocols

Where the gene itself is employed to introduce the gene products, a convenient method of introduction will be through the use of a recombinant vector or vectors that incorporates the desired gene(s), together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the SRF, CRP, and/or GATA gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the SRF, CRP, and/or GATA will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

For introduction of the SRF, CRP, and/or GATA gene, it is proposed that one will desire to preferably employ a vector construct that will deliver the desired gene to the affected cells. This will, of course, generally require that the construct be delivered to the targeted tumor cells, for example, breast, genital, or lung tumor cells. It is proposed that this may be achieved most preferably by introduction of the desired gene through the use of a viral or non-viral vector or vectors to carry the SRF, CRP, and/or GATA sequences to efficiently transfect a cell. This infection may be achieved preferably by liposomal delivery but may also be via adenoviral, a retroviral, a vaccinia virus, herpesvirus or adeno-associated virus vector, or a combination thereof. These vectors have been successfully used to deliver desired sequences to cells and tend to have a high infection efficiency.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment that also contains the SV40 viral origin of replication. Smaller or larger SV40 fragments may also be used, provided there is included the approximately 250 bp sequence extending from the HindIII site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

1. Liposomal Transfection

The expression construct may be entrapped in a liposome. Liposomes are structures created by mixing phospholipids with water, or hydration of phospholipid. The resultant bilayer structures tend to fold back upon themselves. Liposomes are frequently multilamellar, composed of concentric bilayer membranes separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

The present invention also provides particularly useful methods for introducing SRF, CRP, and/or GATA gene products into cells. One method of in vivo gene transfer which can lead to expression of genes transfected into cells involves the use of liposomes. Liposomes can be used for both in vitro and in vivo transfection. Liposome-mediated gene transfer seems to have great potential for certain in vivo applications in animals (Nicolau et al., 1987). Studies have shown that intravenously injected liposomes are taken up essentially in the liver and the spleen, by the macrophages of the reticuloendothelial system. The specific cellular sites of uptake of injected liposomes appears to be mainly spleen macrophages and liver Kupffer cells. Intravenous injection of liposomes/DNA complexes can lead to the uptake of DNA by these cellular sites, and result in the expression of a gene product encoded in the DNA (Nicolau, 1982).

The inventors contemplate that SRF, CRP, and/or GATA gene products can be introduced into cells using liposome-mediated gene transfer. It is proposed that such constructs can be coupled with liposomes and directly introduced via a catheter, as described by Nabel et al. (1990). By employing these methods, SRF, CRP, and/or GATA gene products can be expressed efficiently at a specific site in vivo, not just the liver and spleen cells which are accessible via intravenous injection. Therefore, this invention also encompasses compositions of DNA constructs encoding an SRF, CRP, and/or GATA gene product formulated as a DNA/liposome complex and methods of using such constructs.

Liposomal transfection can be via liposomes composed of, for example, phosphatidylcholine (PC), phosphatidylserine (PS), cholesterol (Chol), N-[1-(2,3-dioleyloxy)propyl]-N,N-trimethylammonium chloride (DOTMA), dioleoylphosphatidyl-ethanolamine (DOPE), and/or 3b[N—(N'N'-dimethylaminoethane)-carbarmoyl cholesterol (DC-Chol), as well as other lipids known to those of skill in the art. Those of skill in the art will recognize that there are a variety of liposomal transfection techniques which will be useful in the present invention. Among these techniques are those described in Nicolau et al., 1987, Nabel et al., 1990, and Gao et al., 1991. In one embodiment of the present invention, liposomes comprising DC-Chol and DOPE which have been prepared following the teaching of Gao et al., 1991, are used. The inventors also anticipate utility for liposomes comprised of DOTMA, such as those which are available commercially under the trademark Lipofectin™, from Vical, Inc., in San Diego, Calif.

Liposomes may be introduced into contact with cells to be transfected by a variety of methods. In cell culture, the liposome-DNA complex can simply be dispersed in the cell culture solution. For application in vivo, liposome-DNA complex are typically injected. Intravenous injection allows liposome-mediated transfer of DNA complex, for example, the liver and the spleen. In order to allow transfection of DNA into cells which are not accessible through intravenous injection, it is possible to directly inject the liposome-DNA complexes into a specific location in an animal's body. For example, Nabel et al. teach injection via a catheter into the arterial wall. In another example, the inventors have used intraperitoneal injection to allow for gene transfer into mice.

The present invention also contemplates compositions comprising a liposomal complex. This liposomal complex will comprise a lipid component and a DNA segment encoding a SRF, CRP, and/or GATA polynucleotide.

The lipid employed to make the liposomal complex can be any of the above-discussed lipids. In particular, DOTMA, DOPE, and/or DC-Chol may form all or part of the liposomal complex. The inventors have had particular success with complexes comprising DC-Chol. In a preferred embodiment, the lipid will comprise DC-Chol and DOPE. While any ratio of DC-Chol to DOPE is expected to have utility, it is expected that those comprising a ratio of DC-Chol:DOPE between 1:20 and 20:1 will be particularly advantageous. The inventors have found that liposomes prepared from a ratio of DC-Chol:DOPE of about 1:10 to about 1:5 have been useful.

It is proposed that it will ultimately be preferable to employ the smallest region needed to suppress the SRF, CRP, and/or GATA polynucleotide so that one is not introducing unnecessary DNA into cells which receive a SRF, CRP, and/or GATA polynucleotide construct. Techniques well known to those of skill in the art, such as the use of restriction enzymes, will allow for the generation of small regions of SRF, CRP, and/or GATA. The ability of these regions to promote smooth muscle cell differentiation can easily be determined by the assays reported in the Examples.

In certain embodiments of the invention, the liposome may be complexed with a hemagglutinatin virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of polynucleotide in vitro and in vivo, then they are applicable for the present invention. Where a bacterial promoter is employed in the DNA construct, it also will be desirable to include within the liposome an appropriate bacterial polymerase.

2. Adenovirus

Another method for in vivo delivery involves the use of an adenovirus vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

Adenovirus is a particularly suitable gene transfer vector because of its midsized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, located at 16.8 mm is particularly efficient during the late phase of infection, and all the mRNA's issued from this promoter possess a 5'-tripartite leader (TL) sequence which makes them preferred mRNA's for translation.

In some cases, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

A particular method of introducing the SRF, CRP, and/or GATA to an animal is to introduce at least one replication-deficient adenovirus comprising the SRF, CRP, and/or GATA polynucleotide. The replication-deficient construct made by E1B and E3 deletion also avoids the viral reproduction inside the cell and transfer to other cells and infection of other people, which means the viral infection activity is shut down after it infects the target cell. The SRF, CRP, and/or GATA gene is still expressed inside the cells. Also, unlike retrovirus, which can only infect proliferating cells, adenovirus is able to transfer the SRF, CRP, and/or GATA gene into both proliferating and non-proliferating cells. Further, the extrachromosomal location of adenovirus in the infected cells decreases the chance of cellular oncogene activation within the treated animal.

Introduction of the adenovirus containing the SRF, CRP, and/or GATA gene product gene into a suitable host is typically done by injecting the virus contained in a buffer.

The nature of the adenovirus vector is not believed to be crucial to the successful practice of the invention. Of course, as discussed above, it is advantageous if the adenovirus vector is replication defective, or at least conditionally defective, The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Adenovirus is easy to grow and manipulate and exhibits broad host range in vitro and in vivo. This group of viruses can be obtained in high titers, e.g., 109-1011 plaque-forming units per ml, and they are highly infective. The life cycle of adenovirus does not require integration in to the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus have been used in eukaryotic gene expression (Levrero et al., 1991; Gomez-Foix et al., 1992) and vaccine development (Grunhaus and Horwitz, 1992; Graham and Prevec, 1992). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotatic inoculation into the brain (Le Gal La Salle et al., 1993).

3. Retroviruses

The retroviruses are a group of single-stranded RNA viruses characterized by an ability to convert their RNA to double-stranded DNA to infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed y components is constructed (Mann et al., 1983). When a recombinant plasmid containing a human cDNA, together with the retroviral LTR and y sequences is introduced into this cell line (by calcium phosphate precipitation for example), the y sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. One limitation to the use of retrovirus vectors in vivo is the limited ability to produce retroviral vector titers greater than 106 infections U/mL. Titers 10- to 1,000-fold higher are necessary for many in vivo applications.

Several properties of the retrovirus have limited its use in lung cancer treatment (Stratford-Perricaudet and Perricaudet, 1991; (i) Infection by retrovirus depends on host cell division. In human cancer, very few mitotic cells can be found in tumor lesions. (ii) The integration of retrovirus into the host genome may cause adverse effects on target cells, because malignant cells are high in genetic instability. (iii) Retrovirus infection is often limited by a certain host range. (iv) Retrovirus has been associated with many malignancies in both mammals and vertebrates. (v) The titer of retrovirus, in general, is 100- to 1,000-fold lower than that of adenovirus.

In one embodiment of the present invention, the SRF, CRP, and/or GATA polynucleotide(s) are comprised on at least 1 retroviral vector.

4. Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. They offer several attractive features for various mammalian cells (Friedmann, 1989; Ridgeway, 1988; Baichwal and Sugden, 1986; Coupar et al., 1988; Howrich et al., 1990).

With the recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Cultures media containing high titers of the recombinant virus were used to infect primary duckling hepatocytes. Stable CAT gene expression was detected for at least 24 days after transfection (Chang et al., 1991).

5. Other Non-viral Vectors

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. As described above, delivery may be via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the polynucleotide encoding the gene of interest may be positioned and expressed at different sites. In certain embodiments, the polynucleotide encoding the gene may be stably maintained in the cell as a separate, episomal segment of DNA. Such polynucleotide segments or "episomes" encode sequences sufficient to permit maintenance and replication independent of or in synchronization with the host cell cycle. How the expression construct is delivered to a cell and where in the cell the polynucleotide remains is dependent on the type of expression construct employed.

In one embodiment of the invention, the expression construct or constructs may simply consist of naked recombinant DNA or plasmids. Transfer of the construct may be performed by any of the methods mentioned above which physically or chemically permeabilize the cell membrane. This is particularly applicable for transfer permeabilize the cell membrane. This is particularly applicable for transfer in vitro but it may be applied to in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Reshef (1986) also demonstrated that direct intraperitoneal injection of $CaPO_4$ precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

Other expression constructs which can be employed to deliver a polynucleotide encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific.

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). A synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a polynucleotide encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a polynucleotide encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a polynucleotide into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

6. Protein Therapy

Another therapy approach is the provision, to a subject, of SRF, CRP, and/or GATA polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

7. Lipid Compositions

In certain embodiments, the present invention concerns a novel composition comprising one or more lipids associated with at least one SRF, CRP, and/or GATA polynucleotide or SRF, CRP, and/or GATA polypeptide, protein, or peptide. A lipid is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. Of course, compounds other than those specifically described herein that are understood by one of skill in the art as lipids are also encompassed by the compositions and methods of the present invention.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

a. Lipid Types

A neutral fat may comprise a glycerol and a fatty acid. A typical glycerol is a three carbon alcohol. A fatty acid generally is a molecule comprising a carbon chain with an acidic moeity (e.g., carboxylic acid) at an end of the chain. The carbon chain may of a fatty acid may be of any length, however, it is preferred that the length of the carbon chain be of from about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, to about 30 or more carbon atoms, and any range derivable therein. However, a preferred range is from about 14 to about 24 carbon atoms in the chain portion of the fatty acid, with about 16 to about 18 carbon atoms being particularly preferred in certain embodiments. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated.

Specific fatty acids include, but are not limited to, linoleic acid, oleic acid, palmitic acid, linolenic acid, stearic acid, lauric acid, myristic acid, arachidic acid, palmitoleic acid, arachidonic acid, ricinoleic acid, tuberculosteric acid, lactobacillic acid. An acidic group of one or more fatty acids is covalently bonded to one or more hydroxyl groups of a glycerol. Thus, a monoglyceride comprises a glycerol and one fatty acid, a diglyceride comprises a glycerol and two fatty acids, and a triglyceride comprises a glycerol and three fatty acids.

A phospholipid generally comprises either glycerol or an sphingosine moiety, an ionic phosphate group to produce an amphipathic compound, and one or more fatty acids. Types of phospholipids include, for example, phophoglycerides, wherein a phosphate group is linked to the first carbon of glycerol of a diglyceride, and sphingophospholipids (e.g., sphingomyelin), wherein a phosphate group is esterified to a sphingosine amino alcohol. Another example of a sphingophospholipid is a sulfatide, which comprises an ionic sulfate group that makes the molecule amphipathic. A phopholipid may, of course, comprise further chemical groups, such as for example, an alcohol attached to the phosphate group. Examples of such alcohol groups include serine, ethanolamine, choline, glycerol and inositol. Thus, specific phosphoglycerides include a phosphatidyl serine, a phosphatidyl ethanolamine, a phosphatidyl choline, a phosphatidyl glycerol or a phosphotidyl inositol. Other phospholipids include a phosphatidic acid or a diacetyl phosphate. In one aspect, a phosphatidylcholine comprises a dioleoylphosphatidylcholine (a.k.a. cardiolipin), an egg phosphatidylcholine, a dipalmitoyl phosphalidycholine, a monomyristoyl phosphatidylcholine, a monopalmitoyl phosphatidylcholine, a monostearoyl phosphatidylcholine, a monooleoyl phosphatidylcholine, a dibutroyl phosphatidylcholine, a divaleroyl phosphatidylcholine, a dicaproyl phosphatidylcholine, a diheptanoyl phosphatidylcholine, a dicapryloyl phosphatidylcholine or a distearoyl phosphatidylcholine.

A glycolipid is related to a sphinogophospholipid, but comprises a carbohydrate group rather than a phosphate group attached to a primary hydroxyl group of the sphingosine. A type of glycolipid called a cerebroside comprises one sugar group (e.g., a glucose or galactose) attached to the primary hydroxyl group. Another example of a glycolipid is a ganglioside (e.g., a monosialdganglioside, a GM1), which comprises about 2, about 3, about 4, about 5, about 6, to about 7 or so sugar groups, that may be in a branched chain, attached to the primary hydroxyl group. In other embodiments, the glycolipid is a ceramide (e.g., lactosylceramide).

A steroid is a four-membered ring system derivative of a phenanthrene. Steroids often possess regulatory functions in cells, tissues and organisms, and include, for example, hormones and related compounds in the progestagen (e.g., progesterone), glucocoricoid (e.g., cortisol), mineralocorticoid (e.g., aldosterone), androgen (e.g., testosterone) and estrogen (e.g., estrone) families. Cholesterol is another example of a steroid, and generally serves structural rather than regulatory functions. Vitamin D is another example of a sterol, and is involved in calcium absorption from the intestine.

A terpene is a lipid comprising one or more five carbon isoprene groups. Terpenes have various biological functions, and include, for example, vitamin A, coenyzme Q and carotenoids (e.g., lycopene and β-carotene).

b. Charged and Neutral Lipid Compositions

In certain embodiments, a lipid component of a composition is uncharged or primarily uncharged. In one embodiment, a lipid component of a composition comprises one or more neutral lipids. In another aspect, a lipid component of a composition may be substantially free of anionic and cationic lipids, such as certain phospholipids (e.g., phosphatidyl choline) and cholesterol. In certain aspects, a lipid component of an uncharged or primarily uncharged lipid composition comprises about 95%, about 96%, about 97%, about 98%, about 99% or 100% lipids without a charge, substantially uncharged lipid(s), and/or a lipid mixture with equal numbers of positive and negative charges.

In other aspects, a lipid composition may be charged. For example, charged phospholipids may be used for preparing a lipid composition according to the present invention and can carry a net positive charge or a net negative charge. In a non-limiting example, diacetyl phosphate can be employed to confer a negative charge on the lipid composition, and stearylamine can be used to confer a positive charge on the lipid composition.

c. Making Lipids

Lipids can be obtained from natural sources, commercial sources or chemically synthesized, as would be known to one of ordinary skill in the art. For example, phospholipids can be from natural sources, such as egg or soybean phosphatidylcholine, brain phosphatidic acid, brain or plant phosphatidylinositol, heart cardiolipin and plant or bacterial phosphatidylethanolamine. In another example, lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). In certain embodiments, stock solutions of lipids in chloroform or chloroform/methanol can be stored at about −20° C. Preferably, chloroform is used as the only solvent since it is more readily evaporated than methanol.

d. Lipid Composition Structures

In a preferred embodiment of the invention, the SRF, CRP, and/or GATA composition may be associated with a lipid. A SRF, CRP, and/or GATA composition associated with a lipid may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure. A lipid or lipid/SRF, CRP, and/or GATA composition associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine(Gibco BRL)-SRF, CRP, and/or GATA composition or Superfect (Qiagen)-SRF, CRP, and/or GATA composition complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

e. Emulsions

A lipid may be comprised in an emulsion. A lipid emulsion is a substantially permanent heterogenous liquid mixture of two or more liquids that do not normally dissolve in each other, by mechanical agitation or by small amounts of additional substances known as emulsifiers. Methods for preparing lipid emulsions and adding additional components are well known in the art (e.g., Modern Pharmaceutics, 1990, incorporated herein by reference).

For example, one or more lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada).

f. Micelles

A lipid may be comprised in a micelle. A micelle is a cluster or aggregate of lipid compounds, generally in the form of a lipid monolayer, and may be prepared using any micelle producing protocol known to those of skill in the art (e.g., Canfield et al., 1990; El-Gorab et al, 1973; Colloidal Surfactant, 1963; and Catalysis in Micellar and Macromolecular Systems, 1975, each incorporated herein by reference). For example, one or more lipids are typically made into a suspension in an organic solvent, the solvent is evaporated, the lipid is resuspended in an aqueous medium, sonicated and then centrifuged.

g. Liposomes

In particular embodiments, a lipid comprises a liposome. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In certain less preferred embodiments, phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition or a liposome, because of the instability and leakiness of the resulting liposomes.

In particular embodiments, a SRF, CRP, and/or GATA composition may be, for example, encapsulated in the aqueous interior of a liposome, interspersed within the lipid bilayer of a liposome, attached to a liposome via a linking molecule that is associated with both the liposome and the SRF, CRP, and/or GATA composition, entrapped in a liposome, complexed with a liposome, etc.

h. Making Liposomes

A liposome used according to the present invention can be made by different methods, as would be known to one of ordinary skill in the art. Phospholipids can form a variety of structures other than liposomes when dispersed in water, depending on the molar ratio of lipid to water. At low ratios the liposome is the preferred structure.

For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with the SRF, CRP, and/or GATA composition, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline.

The average diameter of the particles obtained using Tween 20 for encapsulating the SRF, CRP, and/or GATA composition is about 0.7 to about 1.0 mm in diameter.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Uster 1983, Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al. 1987; Mayhew et al., 1984; Cheng et al., 1987; and Liposome Technology, 1984, each incorporated herein by reference).

A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (III) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures. This preparation produces liposomal/SRF, CRP, and/or GATA composition or liposomes only of appropriate and uniform size, which are structurally stable and produce maximal activity. Such techniques are well-known to those of skill in the art (see, for example Martin, 1990).

Once manufactured, lipid structures can be used to encapsulate compounds that are toxic (e.g., chemotherapeutics) or labile (e.g., nucleic acids) when in circulation. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs. Liposomal encapsulation has resulted in a lower toxicity and a longer serum half-life for such compounds (Gabizon et al., 1990).

Liposomes interact with cells to deliver agents via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Numerous disease treatments are using lipid based gene transfer strategies to enhance conventional or establish novel therapies, in particular therapies for treating hyperproliferative diseases. Advances in liposome formulations have improved the efficiency of gene transfer in vivo (Templeton et al., 1997) and it is contemplated that liposomes are prepared by these methods. Alternate methods of preparing lipid-based formulations for nucleic acid delivery are described (WO 99/18933).

In another liposome formulation, an amphipathic vehicle called a solvent dilution microcarrier (SDMC) enables integration of particular molecules into the bi-layer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

i. Liposome Targeting

Association of the SRF, CRP, and/or GATA composition with a liposome may improve biodistribution and other properties of the SRF, CRP, and/or GATA composition. For example, liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980). Successful liposome-mediated gene transfer in rats after intravenous injection has also been accomplished (Nicolau et al., 1987).

It is contemplated that a liposome/SRF, CRP, and/or GATA composition may comprise additional materials for delivery to a tissue. For example, in certain embodiments of the invention, the lipid or liposome may be associated with a hemagglutinating virus (HVJ). This has been shown to facilitate fusion with the cell membrane and promote cell entry of liposome-encapsulated DNA (Kaneda et al., 1989). In another example, the lipid or liposome may be complexed or employed in conjunction with nuclear non-histone chromosomal proteins (HMG-1) (Kato et al., 1991). In yet further embodiments, the lipid may be complexed or employed in conjunction with both HVJ and HMG-1.

Targeted delivery is achieved by the addition of ligands without compromising the ability of these liposomes deliver large amounts of a SRF, CRP, and/or GATA composition. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with the lipid complex, and can be conjugated to the liposomes by a variety of methods.

j. Cross-Linkers

Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. No. 5,603,872 and U.S. Pat. No. 5,401,511, each specifically incorporated herein by reference in its entirety). Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites will be dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides and sugars. Table 4 details certain hetero-bifunctional cross-linkers considered useful in the present invention.

TABLE 4

HETERO-BIFUNCTIONAL CROSS-LINKERS

| Linker | Reactive Toward | Advantages and Applications | Spacer Arm Length\after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |

TABLE 4-continued

HETERO-BIFUNCTIONAL CROSS-LINKERS

| Linker | Reactive Toward | Advantages and Applications | Spacer Arm Length\after cross-linking |
|---|---|---|---|
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

In instances where a particular polypeptide does not contain a residue amenable for a given cross-linking reagent in its native sequence, conservative genetic or synthetic amino acid changes in the primary sequence can be utilized.

k. Targeting Ligands

The targeting ligand can be either anchored in the hydrophobic portion of the complex or attached to reactive terminal groups of the hydrophilic portion of the complex. The targeting ligand can be attached to the liposome via a linkage to a reactive group, e.g., on the distal end of the hydrophilic polymer. Preferred reactive groups include amino groups, carboxylic groups, hydrazide groups, and thiol groups. The coupling of the targeting ligand to the hydrophilic polymer can be performed by standard methods of organic chemistry that are known to those skilled in the art. In certain embodiments, the total concentration of the targeting ligand can be from about 0.01 to about 10% mol.

Targeting ligands are any ligand specific for a characteristic component of the targeted region. Preferred targeting ligands include proteins such as polyclonal or monoclonal antibodies, antibody fragments, or chimeric antibodies, enzymes, or hormones, or sugars such as mono-, oligo- and poly-saccharides (see, Heath et al., Chem. Phys. Lipids 40:347 (1986)) For example, disialoganglioside GD2 is a tumor antigen that has been identified neuroectodermal origin tumors, such as neuroblastoma, melanoma, small-cell lung carcenoma, glioma and certain sarcomas (Mujoo et al., 1986, Schulz et al., 1984). Liposomes containing anti-disialoganglioside GD2 monoclonal antibodies have been used to aid the targeting of the liposomes to cells expressing the tumor antigen (Montaldo et al., 1999; Pagan et al., 1999). In another non-limiting example, breast and gynecological cancer antigen specific antibodies are described in U.S. Pat. No. 5,939,277, incorporated herein by reference. In a further non-limiting example, prostate cancer specific antibodies are disclosed in U.S. Pat. No. 6,107,090, incorporated herein by reference. Thus, it is contemplated that the antibodies described herein or as would be known to one of ordinary skill in the art may be used to target specific tissues and cell types in combination with the compositions and methods of the present invention. In certain embodiments of the invention, contemplated targeting ligands interact with integrins, proteoglycans, glycoproteins, receptors or transporters. Suitable ligands include any that are specific for cells of the target organ, or for structures of the target organ exposed to the circulation as a result of local pathology, such as tumors.

In certain embodiments of the present invention, in order to enhance the transduction of cells, to increase transduction of target cells, or to limit transduction of undesired cells, antibody or cyclic peptide targeting moieties (ligands) are associated with the lipid complex. Such methods are known in the art. For example, liposomes have been described further that specifically target cells of the mammalian central nervous system (U.S. Pat. No. 5,786,214, incorporated herein by reference). The liposomes are composed essentially of N-glutarylphosphatidylethanolamine, cholesterol and oleic acid, wherein a monoclonal antibody specific for neuroglia is conjugated to the liposomes. It is contemplated that a monoclonal antibody or antibody fragment may be used to target delivery to specific cells, tissues, or organs in the animal, such as for example, brain, heart, lung, liver, etc.

Still further, a SRF, CRP, and/or GATA composition may be delivered to a target cell via receptor-mediated delivery and/or targeting vehicles comprising a lipid or liposome. These take advantage of the selective uptake of macromolecules by receptor-mediated endocytosis that will be occurring in a target cell. In view of the cell type-specific distribution of various receptors, this delivery method adds another degree of specificity to the present invention.

Thus, in certain aspects of the present invention, a ligand will be chosen to correspond to a receptor specifically expressed on the target cell population. A cell-specific SRF, CRP, and/or GATA composition delivery and/or targeting vehicle may comprise a specific binding ligand in combination with a liposome. The SRF, CRP, and/or GATA composition to be delivered is housed within a liposome and the specific binding ligand is functionally incorporated into a liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In certain embodiments, a receptor-mediated delivery and/or targeting vehicles comprise a cell receptor-specific ligand and a SRF, CRP, and/or GATA composition-binding agent. Others comprise a cell receptor-specific ligand to which SRF, CRP, and/or GATA composition to be delivered has been operatively attached. For example, several ligands have been used for receptor-mediated gene transfer (Wu and Wu, 1987; Wagner et al., 1990; Perales et al., 1994; Myers, EPO 0273085), which establishes the operability of the technique. In another example, specific delivery in the context of another mammalian cell type has been described (Wu and Wu, 1993; incorporated herein by reference).

In still further embodiments, the specific binding ligand may comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). The asialoglycoprotein, asialofetuin, which contains terminal galactosyl residues, also has been demonstrated to target liposomes to the liver (Spanjer and Scherphof, 1983; Hara et al., 1996). The sugars mannosyl, fucosyl or N-acetyl glucosanine, when coupled to the backbone of a polypeptide, bind the high affinity manose receptor (U.S. Pat. No. 5,432,260, specifically incorporated herein by reference in its entirety). It is contemplated that the cell or tissue-specific transforming constructs of the present invention can be specifically delivered into a target cell or tissue in a similar manner.

In another example, lactosyl ceramide, and peptides that target the LDL receptor related proteins, such as apolipoprotein E3 ("Apo E") have been useful in targeting liposomes to the liver (Spanjer and Scherphof, 1983; WO 98/0748).

Folate and the folate receptor have also been described as useful for cellular targeting (U.S. Pat. No. 5,871,727). In this example, the vitamin folate is coupled to the complex. The folate receptor has high affinity for its ligand and is overexpressed on the surface of several malignant cell lines, including lung, breast and brain tumors. Anti-folate such as methotrexate may also be used as targeting ligands. Transferrin mediated delivery systems target a wide range of replicating cells that express the transferrin receptor (Gilliland et al., 1980).

l. Liposome/Nucleic Acid Combinations

In certain embodiments, a liposome/SRF, CRP, and/or GATA composition may comprise a nucleic acid, such as, for example, an oligonucleotide, a polynucleotide or a nucleic acid construct (e.g., an expression vector). Where a bacterial promoter is employed in the DNA construct that is to be transfected into eukaryotic cells, it also will be desirable to include within the liposome an appropriate bacterial polymerase.

It is contemplated that when the liposome/SRF, CRP, and/or GATA composition comprises a cell or tissue specific nucleic acid, this technique may have applicability in the present invention. In certain embodiments, lipid-based non-viral formulations provide an alternative to viral gene therapies. Although many cell culture studies have documented lipid-based non-viral gene transfer, systemic gene delivery via lipid-based formulations has been limited. A major limitation of non-viral lipid-based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use aerosolization, subcutaneous, intradermal, intratumoral, or intracranial injection to avoid the toxicity and stability problems associated with cationic lipids in the circulation. The interaction of liposomes and plasma proteins is largely responsible for the disparity between the efficiency of in vitro (Felgner et al., 1987) and in vivo gene transfer (Zhu et al., 1993; Philip et al., 1993; Solodin et al., 1995; Liu et al., 1995; Thierry et al., 1995; Tsukamoto et al., 1995; Aksentijevich et al., 1996).

An exemplary method for targeting viral particles to cells that lack a single cell-specific marker has been described (U.S. Pat. No. 5,849,718). In this method, for example, antibody A may have specificity for tumor, but also for normal heart and lung tissue, while antibody B has specificity for tumor but also normal liver cells. The use of antibody A or antibody B alone to deliver an anti-proliferative nucleic acid to the tumor would possibly result in unwanted damage to heart and lung or liver cells. However, antibody A and antibody B can be used together for improved cell targeting. Thus, antibody A is coupled to a gene encoding an anti-proliferative nucleic acid and is delivered, via a receptor mediated uptake system, to tumor as well as heart and lung tissue. However, the gene is not transcribed in these cells as they lack a necessary transcription factor. Antibody B is coupled to a universally active gene encoding the transcription factor necessary for the transcription of the anti-proliferative nucleic acid and is delivered to tumor and liver cells. Therefore, in heart and lung cells only the inactive anti-proliferative nucleic acid is delivered, where it is not transcribed, leading to no adverse effects. In liver cells, the gene encoding the transcription factor is delivered and transcribed, but has no effect because no an anti-proliferative nucleic acid gene is present. In tumor cells, however, both genes are delivered and the transcription factor can activate transcription of the anti-proliferative nucleic acid, leading to tumor-specific toxic effects.

The addition of targeting ligands for gene delivery for the treatment of hyperproliferative diseases permits the delivery of genes whose gene products are more toxic than do non-targeted systems. Examples of the more toxic genes that can be delivered includes pro-apoptotic genes such as Bax and Bak plus genes derived from viruses and other pathogens such as the adenoviral E4orf4 and the *E. coli* purine nucleoside phosphorylase, a so-called "suicide gene" which converts the prodrug 6-methylpurine deoxyriboside to toxic purine 6-methylpurine. Other examples of suicide genes used with prodrug therapy are the *E. coli* cytosine deaminase gene and the HSV thymidine kinase gene.

It is also possible to utilize untargeted or targeted lipid complexes to generate recombinant or modified viruses in vivo. For example, two or more plasmids could be used to introduce retroviral sequences plus a therapeutic gene into a hyperproliferative cell. Retroviral proteins provided in trans from one of the plasmids would permit packaging of the second, therapeutic gene-carrying plasmid. Transduced cells, therefore, would become a site for production of non-replicative retroviruses carrying the therapeutic gene. These retroviruses would then be capable of infecting nearby cells. The promoter for the therapeutic gene may or may not be inducible or tissue specific.

Similarly, the transferred nucleic acid may represent the DNA for a replication competent or conditionally replicating viral genome, such as an adenoviral genome that lacks all or part of the adenoviral E1a or E2b region or that has one or more tissue-specific or inducible promoters driving transcription from the E1a and/or E1b regions. This replicating or conditional replicating nucleic acid may or may not contain an additional therapeutic gene such as a tumor suppressor gene or anti-oncogene.

m. Lipid Administration

The actual dosage amount of a lipid composition (e.g., a liposome-SRF, CRP, and/or GATA composition) administered to a patient can be determined by physical and physiological factors such as body weight, severity of condition, idiopathy of the patient and on the route of administration. With these considerations in mind, the dosage of a lipid composition for a particular subject and/or course of treatment can readily be determined.

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, subcutaneously, intravesicularlly, mucosally, intrapericardially, orally, topically, locally and/or using aerosol, injection, infusion, continuous infusion, localized perfusion bathing target cells directly or via a catheter and/or lavage.

VII. Pharmaceutical Compositions and Routes of Administration

Compositions of the present invention may have an effective amount of a smooth muscle cell and/or tissue derived therefrom (by methods of the present invention) for therapeutic administration for cardiac disease and, in some embodiments, in combination with an effective amount of a compound (second agent) that is an anti-cardiac disease agent. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

The expression vectors and delivery vehicles of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The vectors of the present invention are advantageously administered in the form of injectable compositions either as liquid solutions or suspensions; solid forms suitable for solution in, or suspension in, liquid prior to injection also may be prepared. These preparations also may be emulsified. A typical compositions for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as theyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

All the essential materials and reagents required for differentiating a cell into a smooth muscle cell and/or treat cardiac disease may be assembled together in a kit. When the components of the kit are provided in one or more liquid solutions, the liquid solution preferably is an aqueous solution, with a sterile aqueous solution being particularly preferred.

For in vivo use, an anti-cardiac disease agent may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the gene therapy and/or the anti-cardiac disease drug.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

The active compounds of the present invention will often be formulated for parenteral administration, e.g., formulated for injection via the intravenous, intramuscular, subcutaneous, or even intraperitoneal routes. The preparation of an aqueous composition that contains a second agent(s) as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fingi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Targeting of cardiovascular tissues may be accomplished in any one of a variety of ways. Plasmid vectors and retroviral vectors, adenovirus vectors, and other viral vectors all present means by which to target cardiovascular tissue. The inventors anticipate particular success for the use of liposomes to target SRF, CRP, and/or GATA genes to cells, examples of which include fibroblasts or stem cells, for differentiating into smooth muscle cells. For example, DNA encoding SRF, CRP, and/or GATA may be complexed with liposomes in the manner described above, and this DNA/liposome complex is injected into patients with cardiac disease, intravenous injection can be used to direct the gene to all cell. Directly injecting the liposome complex into the proximity of the diseased tissue can also provide for targeting of the complex with some forms of cardiac disease. Of course, the potential for liposomes that are selectively taken up by a population of cells exists, and such liposomes will also be useful for targeting the gene.

Those of skill in the art will recognize that the best treatment regimens for using SRF, CRP, and/or GATA to generate differentiation of a cell into a smooth muscle cell and/or to treat diseased cardiac tissue can be straightforwardly determined. This is not a question of experimentation, but rather one of optimization, which is routinely conducted in the medical arts. In one exemplary embodiment, in vivo studies in nude mice provide a starting point from which to begin to optimize the dosage and delivery regimes. The frequency of injection will initially be once a wk, as was done some mice studies. However, this frequency might be optimally adjusted from one day to every two weeks to monthly, depending upon the results obtained from the initial clinical trials and the needs of a particular patient. Human dosage amounts can initially be determined by extrapolating from the amount of SRF, CRP, and/or GATA used in mice. In certain embodiments it is envisioned that the dosage may vary from between about 1 mg SRF, CRP, and/or GATA DNA/Kg body weight to about 5000 mg SRF, CRP, and/or GATA DNA/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg SRF, CRP, and/or GATA DNA/Kg body to about 20 mg SRF, CRP, and/or GATA DNA/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Exemplary Methods and Materials

Expression Vectors and Reporter Genes

Luciferase reporter plasmids Gal4-Luc, SMA-Luc, SM22-Luc, and c-fosSRE1-Luc, and expression vectors pCGN-SRF, pCGN-SRFAC, pCGN-GATA2, pcDNA-GATA6, Gal-DB, Gal-MADS, and MBP-GATA4 were described previously (Sepulveda et al., 1998); (Belaguli et al., 2000). V5-tag full length CRP2 (1-193) and deletion mutants CRP2ΔN (1-112), CRP2ΔZF1 (aa 35-193), CRP2ΔC (aa 113-193), CRP2ZF2+ZF3 (aa 35-145) and CRP2DZF4 (aa 1-145) were constructed by ligation of PCR-amplified fragments from rat pBSSK-CRP2 into eukaryotic expression vectors pcDNA3.1D/V5 (Invitrogen). HA-tag full length rat CRP2 was generated by subcloning CRP2 fragment from pBSSK-CRP2 into CMV-driven expression vector pCGN. Myc-tag full length mouse GATA4 (1-440) and deletion mutants G4ΔN (188-440), G4ΔN+ΔZF1 (248-440), G4ZF1+ZF2 (188-335), G4ΔC (1-304) and G4ΔZF2+ΔC (1-249) were constructed by ligation of RT-PCR-amplified fragments into eukaryotic expression vectors pcDNA3.1myc-His (Invitrogen), which were obtained from Carl Brown (Houston, Tex.). Myc-tag full length chicken GATA6 (1-443) was constructed by ligating PCR-amplified fragments from pcDNA-GATA6 into eukaryotic expression vectors pcDNA3.1myc-His (Invitrogen). Full length human SRF or rat CRP2 cDNA were cloned into pGEX-2T (Stratagene) to construct bacterial expressed GST-SRF and GST-CRP2 vectors. Luciferase reporters, cloned in pGL2 (Promega), SMGA5-Luc (from Dr. Warren Zimmer, Mobile, Ala.) and -549Calp-LucI (from Dr. Joseph Miano, Milwaukee, Wis.), were generous gifts. Expression vector pcDNA-FLAG-E12 was obtained from Dr. Eric Olson (Dallas, Tex.).

Antibodies

Polyclonal rabbit anti-chicken CRP2 antibodies were generated by Louis et al. (1997). Monoclonal antibodies for smooth muscle α-actin (SMA, 1A4), h-caldesmon (hHCD), calponin (hCP), SM-MHC(HSM-V), sarcomeric α-actin (5C5), and avian calponin (CP-93) were from Sigma; smooth muscle g-actin (SMGA, B4) was from ICN; epitope tags V5, myc (Invitrogen), HA-probe (Santa Cruz), and FLAG (M2, Sigma), were purchased commercially. Monoclonal anti-SM22α (1A8) was obtained from Dr. Saverio Sartore (Padua, Italy).

Whole Mount In Situ Hybridization of CRP1 and CRP2 in Early Chick Embryos

To examine the expression patterns of CRP1 and CRP2, antisense probes were synthesized from the chick partial cDNAs covering nucleotides 49 to 941 (CRP1) and 4 to 806 (CRP2). Whole mount in situ hybridization of chick embryos was carried out by methods well known in the art (Yamada et al., 1999).

Transfection Assays to Assess SMC Target Gene Promoters

CV1 cells were grown and maintained at subconfluence (<70%) level in Dulbecco modified Eagle medium (DMEM) containing 10% fetal bovine serum. Transient transfections were performed using Fugene 6 (Roche) according to manufacturer's recommendation. A series of luciferase assays was performed by transient transfection in combination of CMV-driven expression vectors pCGN-SRF (200 ng), pcDNA-myc-GATA6 (400 ng), pcDNA-V5-CRP2 (500 ng), pCGN-SRFAC, luciferase reporters (200 ng), and empty expression vectors pCGN to a balanced total of 1.3 mg of plasmids per 2-cm-diameter well of 12-well plate. For one-hybrid analysis of recruitment of CRP2 by a Gal-MADS fusion, luciferase reporter Gal-Luc (200 ng), Gal-DB (200 ng) or Gal-MADS (200 ng), and CRP2 (500 ng) or CRP2-VP16 (500 ng) were used. Co-transfection experiments were performed in duplicate and repeated at least 3 times. Luciferase activity was normalized to base-line reporter gene activity as fold-activation, with error bars representing SEM.

Co-Immunoprecipitation of CRP2, SRF and GATA4

CV1 fibroblasts were co-transfected with epitope-tag expression vectors, pcDNA-V5-CRP2, pCGN-SRF (HA), pcDNA-myc-GATA6, and pcDNA-FLAG-E12. Approximately 100 µg of total protein were incubated with different primary antibodies against specific epitopes (anti-V5, 2 ml/ml; anti-HA, 10 ml/ml; anti-myc, 2 ml/ml; anti-FLAG 2 ml/ml) and retrieved with Protein-G Sepharose resin. Co-immunoprecipitated proteins were resolved on 4-20% SDS-polyacrylamide gel, followed by Coomassie staining or Western immunoblot analysis (anti-V5, 1:5,000; anti-HA, 1:1,000; anti-myc, 1:5,000; anti-FLAG, 1:5,000).

Electrophoretic Mobility Assays of SRF and Cofactors

PCR-amplified double-stranded oligonucleotides (−141 to +1) from the 5' flanking sequence of murine smooth muscle α-actin (M57409) containing SRE1 and SRE2 were used for electrophoretic mobility shift assays, by methods well known in the art (Sepulveda et al., 1998).

In Vitro Pull-Down Assays

Recombinant fusion proteins, GST-CRP2, GST-SRF and MBP-GATA4, and control GST and MBP were expressed in bacteria (Sepulveda et al., 1998) and affinity purified. In vitro translation of various [$^{35}$S] methionine-labeled protein products were performed using rabbit reticulocyte lysates from TnT In vitro Translation kit (Promega). Pull-down assay was performed by methods well known in the art (Sepulveda et al., 1998).

Transdifferentiation Assays in Pluripotent 10T1/2 Cells

Murine pluripotent 10T1/2 fibroblasts (ATCC) were between passages 5 to 12 and maintained at low confluence (~25%) in DMEM containing 2% horse serum. Transfection in combination of different expression plasmids (3 µg each) was performed using Fugene 6. Two days after transfection, half of the cells per plate was extracted for RNA using an RNeasy Kit (Qiagen), and the RNA was treated with RNase-free DNase I. RT-PCR assays were carried out on the extracted RNA with specific primers for SMA, SM22α, calponin, SM-MHC (Yamashita et al., 2000), cardiac a-actin, SMGA (Chang et al., 1984) and GAPDH (Dugaiczyk, 1983). Approximately 2 weeks following transfection, 95% of cells were harvested for Western immunoblot analysis while the remaining 5% of cells were plated on glass slides for indirect immunofluorescence analysis Isolation of Proepicardial Organ (PEO) Cells Quail stage HH17 PEOs were dissected and cultured as described (Landerholm et al., 1999). To localize endogenous CRP2 protein, explanted PEOs were cultured in glass chamber slides for 3 to 5 days and then characterized by immunofluorescence assays as described (Lu et al., 2001) with primary antibodies (CRP2, 1:200 Probes).

EXAMPLE 2

Avian CRP1 and CRP2 Genes are Co-Expressed During Early Cardiovascular Development In situ hybridization analysis revealed CRP1 expression in the lateral plate precardiac mesoderm at HH7 (FIG. 1A), prior to the migration and fusion of the bilateral cardiac precursors. Previously, it was observed that SRF transcripts overlapped with GATA4 and Nkx2-5 mRNA (Wei et al., 2001; Sepulveda et al., 2002) in regions where SMA and cardiac α-actin gene activity were superimposed in early committed myocardial cells of the heart (Ruzicka and Schwartz, 1988). Thus, CRP1 appears coincident with cardiac-restricted transcription factors during the onset of cardiac differentiation. At HH10, CRP1 expression was also evident in the underlying foregut endoderm and the myocardium, but absent in the endocardium and the overlying pharynx (FIG. 1A, lower panel). Cardiac-specific expression of CRP1 is maintained as the heart takes on the familiar looped-tube appearance by stage HH12. FIG. 1B revealed CRP2 expression beginning at HH7 in the anterior portion of the crescent and the region of the developing head fold and anterior intestinal portal. CRP2 is expressed in the region of the developing head fold and outflow tract at early stages (HH7 and HH8). By HH12, CRP2 appears in the left and right dorsal aortae and the truncus and bulbus arteriosus with some degree of ventricular overlap (the bulbo-ventricular region) and in a discrete area of expression at the junction of the vitelline veins in the sinus venosus (FIG. 1B, lower panel), consistent with the upregulation of SMA expression and VSMC differentiation (Ruzicka and Schwartz, 1988).

It was previously reported that CRP2 expression was increased in proepicardial cells during differentiation to coronary SMCs in vitro (Landerholm et al., 1999). Using rabbit anti-chicken CRP2 (Louis et al., 1997), it was observed that endogenous CRP2 was localized to the nucleus during initial activation of SMC-specific transcription in proepicardial cells (FIG. 1Ci). Specifically, Endogenous CRP2 is localized to the nucleus in epicardial cells (i) during the period of initial activation of SMC-specific gene transcription (iv). Upon epithelial to mesenchymal transformation (ii) and progression to mature SMCs (iii), Thus, as these nascent SMCs matured to a more fully differentiated phenotype, CRP2 was upregulated and became localized to the cytoskeleton (FIGS. 1Cii and 1Ciii) This cellular distribution in mature coronary SMCs is consistent with the existing expression and functional data for CRP2 in developing and mature vascular smooth muscle (Jain et al., 1996; Louis et al., 1997).

EXAMPLE 3

Synergistic Interactions of CRPS with SRF and GATA Factors Transactivated SMC Target Gene Promoters Both LIM-only proteins (including the CRPs) and GATA transcription factors contain similar zinc-finger motifs that could potentially heterodimerize. For example, Lmo2, a LIM-only protein, was demonstrated as an associating molecule with GATA1 in transcriptional complex assembly important for erythropeoisis (Wadman et al., 1997; Mead et al., 2001). This suggested the possibility that LIM-only CRP1 or CRP2 may interact with GATA family members enriched in the cardiovascular system, such as GATA4 and GATA6. Previously, synergism was shown between SRF and GATA4, GATA5 and GATA6 in mediating the activation of SRF-dependent gene promoters, including SMC marker genes SMαA, SM22α and SM γ-actin (Belaguli et al., 2000).

Figure 2:
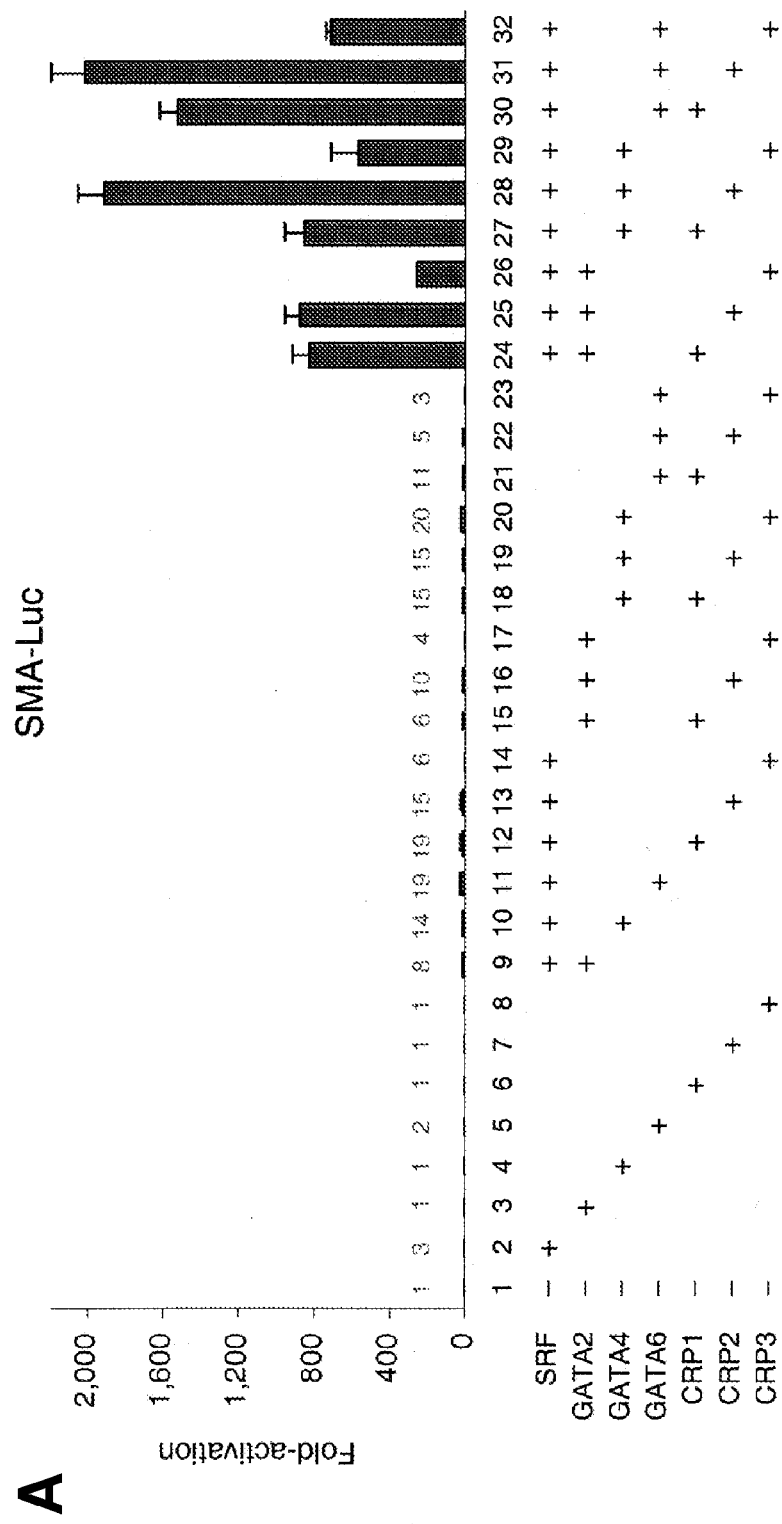
FIGS. 2A through 2D show that combinatorial interactions among CRPs, SRF, and GATA factors facilitated robust activation of SMC-target gene promoters.
Figure 2:
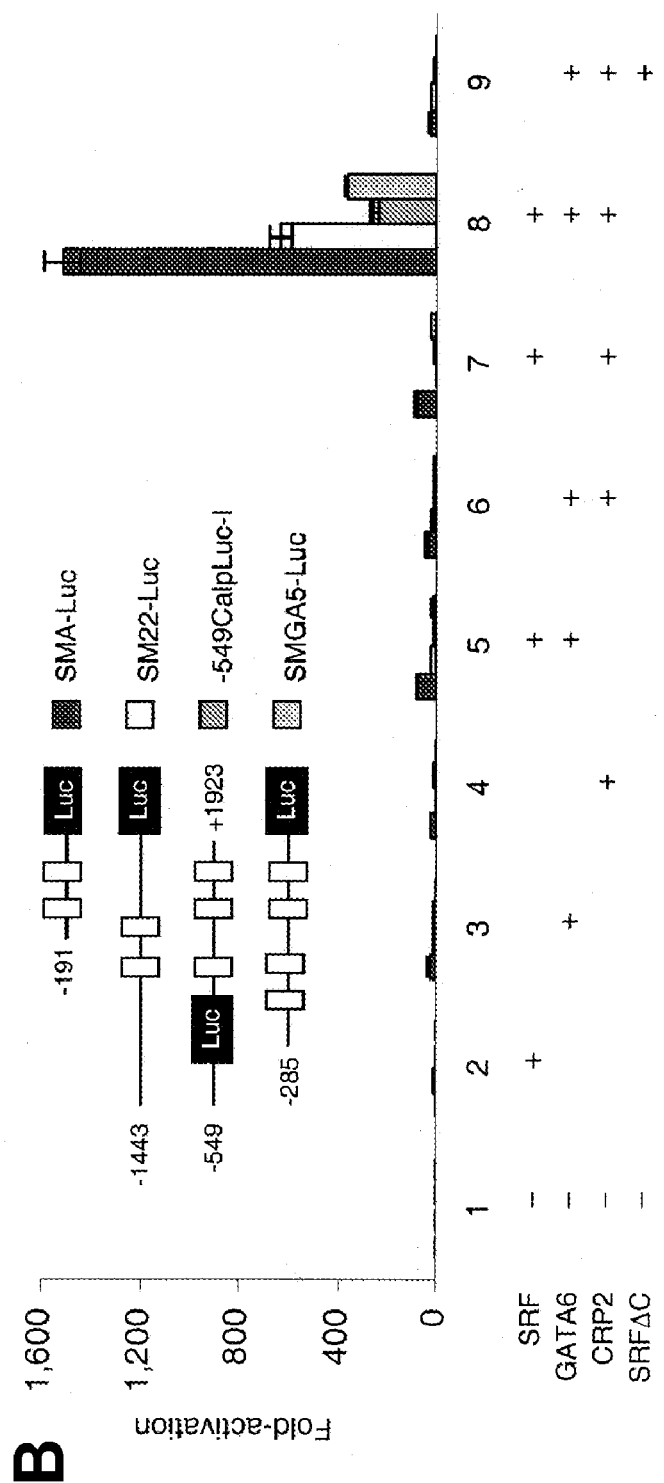
Figure 2:
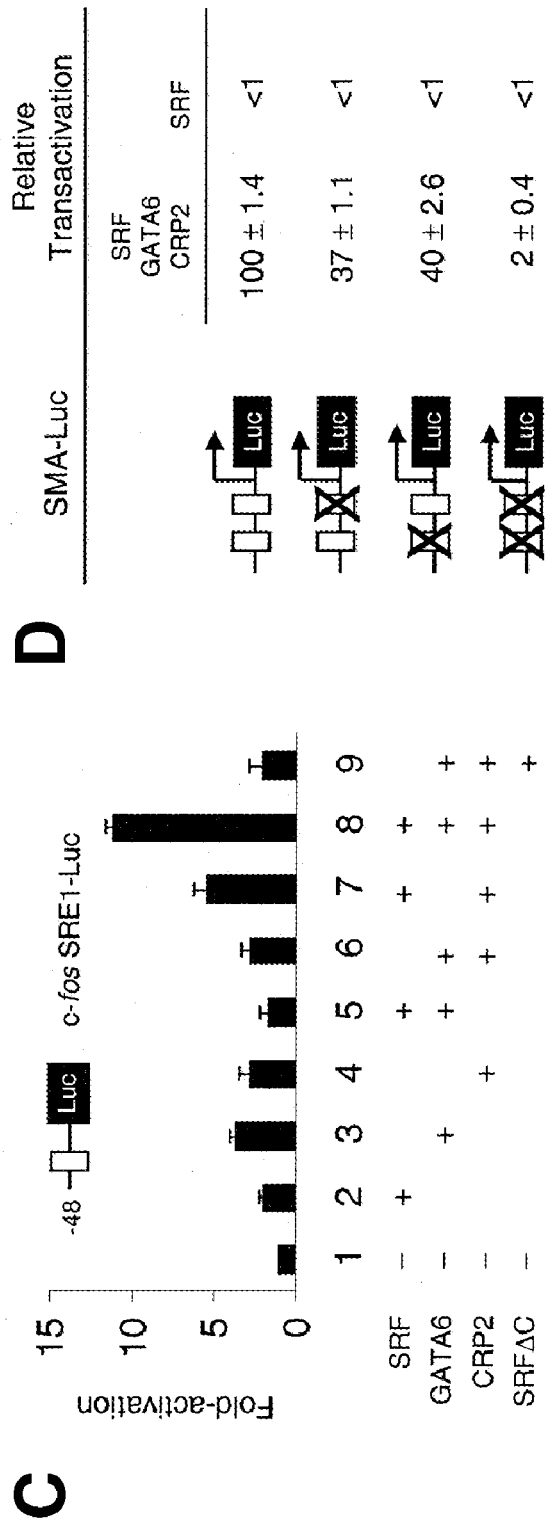
Figure 3:
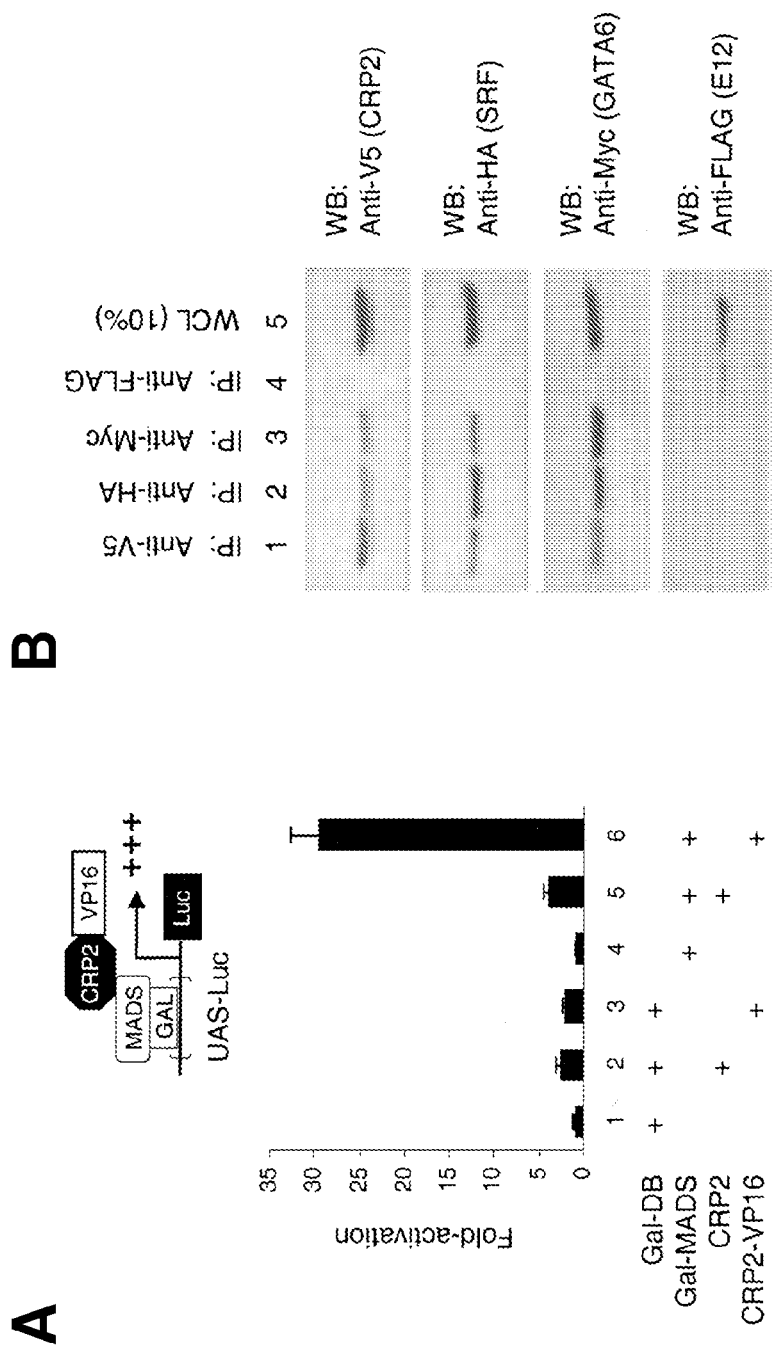
FIGS. 3A through 3C show that CRP2 co-associated with SRF and GATA factors and formed in vivo protein complexes.
Figure 3:
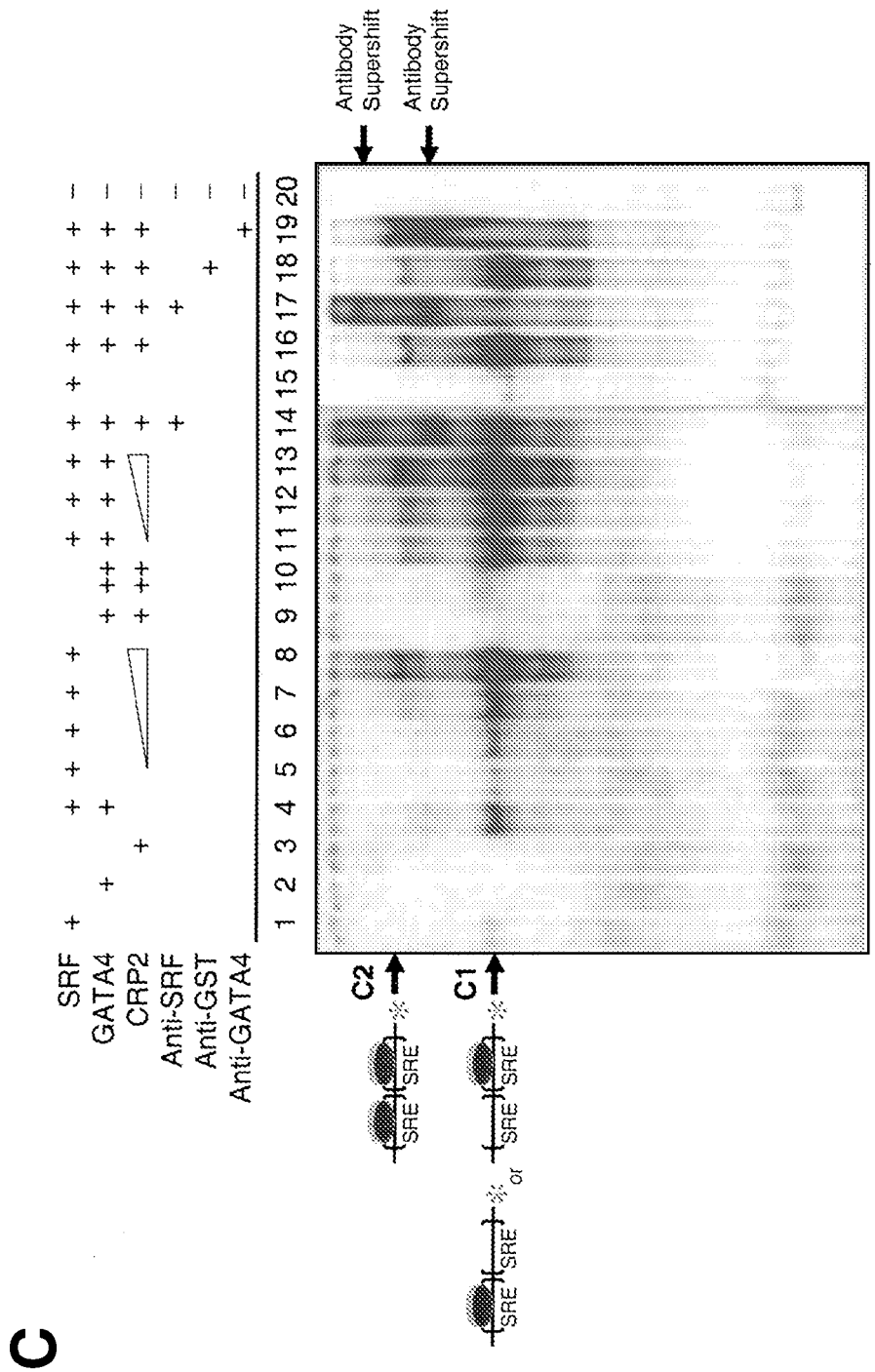

It was determined that CRPs could facilitate transcriptional activity of the SRF-GATA-complex, especially of promoters encoding the SMC target genes. Expression of CRP1, CRP2 and/or CRP3 alone had minimal effects on SMA reporter activity in a heterologous system using monkey CV1 fibroblasts (FIG. 2A, lanes 6-8). Pairings with SRF and/or with GATA2, GATA4 or GATA6, however, resulted in co-activation of about 10 to 30-fold above basal levels (FIG. 2A, lanes 9-23). In the presence of SRF and GATA factors, addition of CRP1 or CRP2, co-activated the SMA promoter several orders of magnitude (FIG. 2A, lanes 24 and 25, 27 and 28, 30 and 31). Weaker activation was found with CRP3 (FIG. 2A, lanes 26, 29, 32). Previously, it was shown that GATA4 and GATA6 are equivalent in co-transfection assays with SRF (Belaguli et al., 2000). Again, the two GATA factors can substitute for each other in combinatorial interactions with CRP2 and SRF to drive SMA promoter (FIG. 3A, lanes 28, 31). Even GATA2, an important transcription factor in erythrogenesis and myogenesis, was able to augment SRF-CRP-induced transactivation of SMA promoter (FIG. 3A, lane 24-26). Thus, CRP1 and CRP2 and the GATA factors appeared to be interchangeable, while CRP3 was nonequivalent.

Other smooth muscle gene promoters were also responsive to this triple-factor combination in fibroblasts (FIG. 2B). The SM22α promoter, which contains two SREs, was activated about 600 fold by the combination of these three factors, while the −549Calponin-I reporter (Miano et al., 2000), with three intronic SREs, and the smooth muscle γ-actin SMGA5 promoter, with four SREs, were activated about 250 and 300 fold, respectively (FIG. 2B). In contrast, weak co-activation was seen with the single SRE containing c-fos promoter (FIG. 2C). Furthermore, mutation in either SRE on the SMA promoter reduced the synergistic transactivation by these transcription factors (FIG. 3D). In the double-SRE-mutant reporter, the responsiveness to CRP2 is completely abolished (FIG. 3D). These results suggest that most of the synergistic co-activation by CRP2 requires efficient binding of SRF to multiple SREs. Consistent with this idea, substitution of the transactivation defective SRFAC mutant (Belaguli et al., 2000) for wildtype SRF in combination with GATA6 and CRP2 resulted in a greater than 95% reduction in co-activation of these multi-SRE containing smooth muscle gene promoters (FIGS. 2B and 2C).

EXAMPLE 4

CRP2 Co-Associated with Nuclear Transcription Factors

The synergistic activation displayed by CRP2, SRF, and GATA factors on SMC target genes requires their physical interaction, which was confirmed by a mammalian two-hybrid study, specifically to determine if CRP2 was recruited by SRF to target DNA (FIG. 3A). CV1 cells were transfected with Gal4 UAS-luciferase reporter and expression plasmids encoding SRF MADS box-Gal4 DNA-binding domain fusion protein (FIG. 3A, lanes 4, 5, 6). Cotransfection of wildtype CRP2 expression vector stimulated the reporter activity five-fold (FIG. 3A, lane 5) whereas addition of a fusion CRP2 protein containing a viral transactivation domain, VP16, greatly augmented Gal4 reporter activity by 30 fold (FIG. 3A, lane 6). These results indicate that the minimal DNA-binding domain of SRF, the MADS box, facilitated recruitment of CRP2 to the Gal4 minimal promoter.

Figure 4:
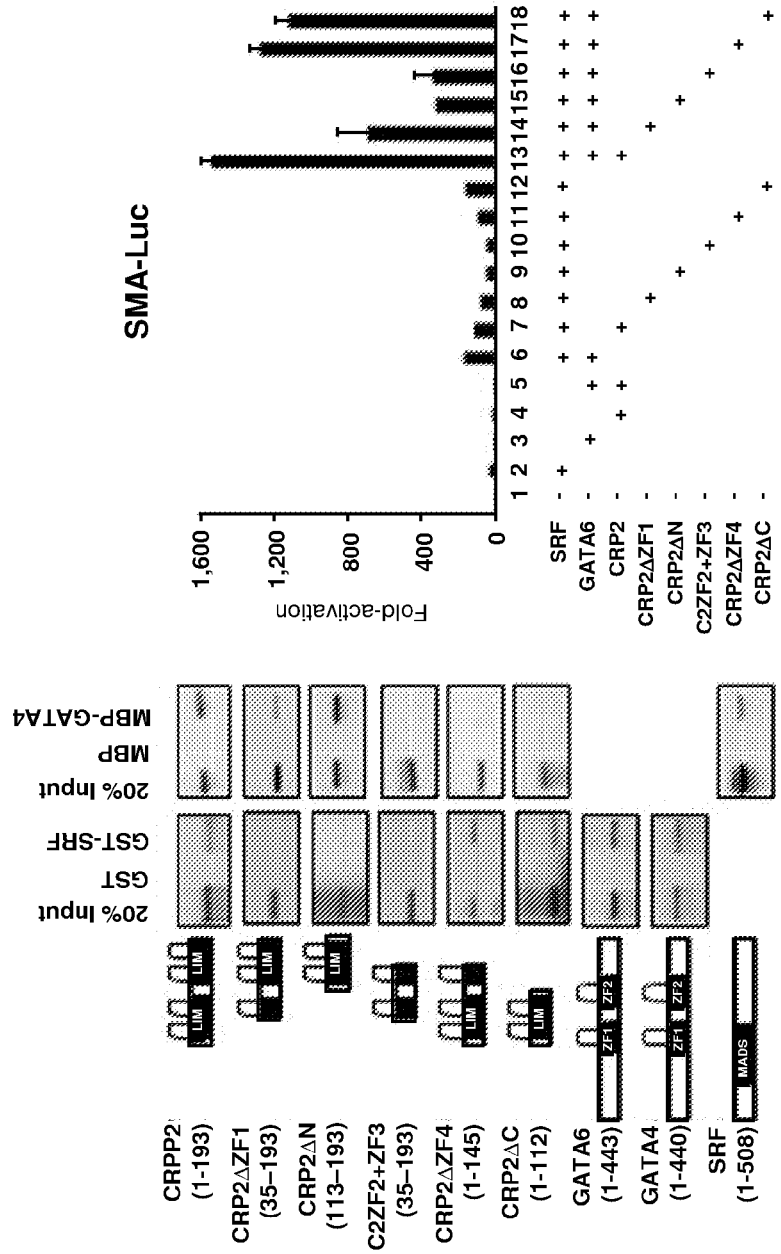
FIGS. 4A through 4D demonstrate that CRP2 is a bridging molecule. Fine mapping revealed obligatory roles for intact LIM domains of CRP2 and the C-terminal zinc-finger of GATA protein for co-association and transactivation.
Figure 4:
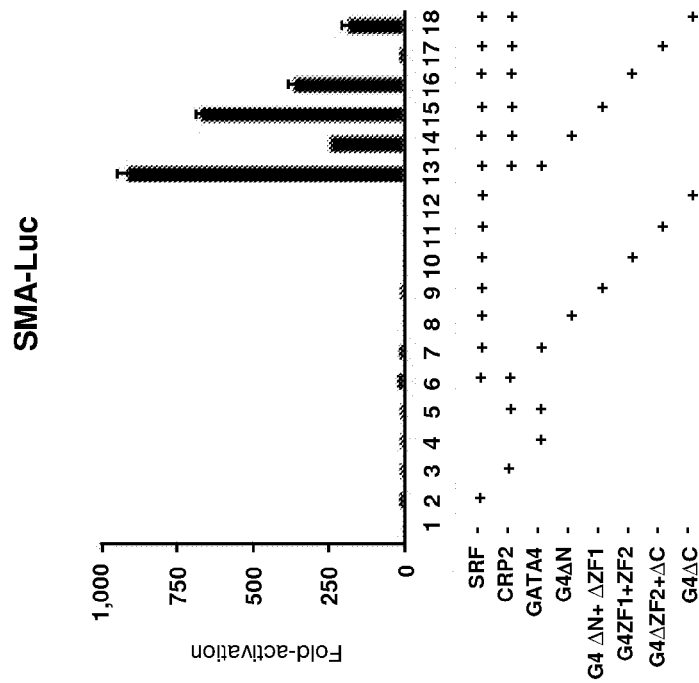
Figure 4:
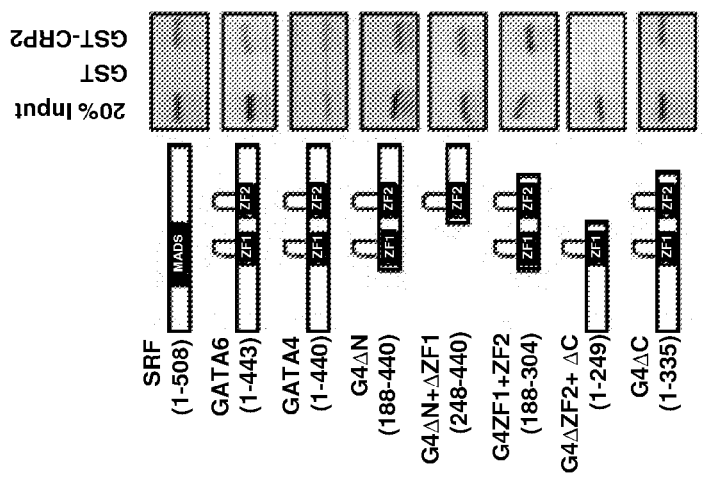

The physical association of CRP2, SRF and GATA6 in cells was further characterized by co-immunoprecipitation assays of epitope-tagged proteins. CV1 fibroblasts were cotransfected with constructs overexpressing V5-tag CRP2, HA-tag SRF, myc-tag GATA6, and FLAG-tag E112. The non-tissue-specific basic-helix-loop-helix (bHLH) transcription factor E12 served as a negative control. Cell lysates were divided into equal aliquots and immunoprecipitated with antibodies directed against each epitope-tag protein. As seen in the immunoblot analysis, CRP2, SRF and GATA6 co-immunoprecipitated with each other (FIG. 3B, lanes 1, 2 and 3), while none of the transfactors interacted with E12 (FIG. 4B, lane 4).

In FIG. 3C, EMSAs were performed with a sub-optimal amount of SRF that resulted in a barely detected complex (C1) on the SMA promoter (FIG. 3C, lanes 1 and 15). Increasing amounts of CRP2 added to a constant sub-optimal amount of SRF caused increased SRF binding (FIG. 3C, lanes 5-8), while GATA4 also stimulated SRF binding (FIG. 3C, lane 4). Even though CRP2 and GATA4 were unable by themselves to bind to the SMA promoter (FIG. 3C, lanes 9 and 10), they facilitated SRF binding as a major complex, demonstrating occupation of either the first and/or the second SRE. However, CRP2 and GATA4 together strongly increased SRF binding resulting in two well-resolved complexes (C1 and C2, FIG. 3C, lanes 11-13, 16), indicating progressive occupancy of two SREs in the SMA promoter. These two complexes were super-shifted by an antibody against SRF (FIG. 3C, lane 14 and 17). An antibody against the recombinant GST-CRP2 resulted in diminished C1 band (FIG. 3C, lane 19), while anti-GATA4 did not super shift the complexes (FIG. 3C, lane 18), possibly due to interference of the protein-protein binding domain with the epitope. Thus, CRP2 and GATA4 recruited by SRF significantly increased cooperative SRF DNA binding affinity.

EXAMPLE 5

CRP2 Functioned as a Bridging Molecule for Association with SRF and GATA Factors The domains that are required for physical association of CRP2, SRF and GATA factor were mapped. Previously, LIM-only protein Lmo2 served as a bridging molecule assembling a transcription complex important in hematopoeisis (Wadman et al., 1997). As shown in FIG. 4A, the two LIM domains of CRP2 independently co-associated with SRF (N-terminal LIM) and with GATA protein (C-terminal LIM), respectively. Deletion of the first zinc finger (in CRP2ΔZF1 and C2ZF2+ZF3 mutants) or complete removal of both zinc fingers (in CRP2ΔN mutant) of the N-terminal LIM domain of CRP2 disrupts its binding to GST-SRF (FIG. 4A, lanes 1-3) and reduced co-activation of SMA promoter activity (FIG. 4B, lanes 8-10 and 14-16). On the other hand, intact C-terminal LIM motif is necessary for CRP2's interaction with GATA4. As shown, removal of the second zinc finger (in CRP2ΔZF4 and C2ZF2+ZF3 mutants) or complete removal of both zinc fingers (in CRP2ΔC mutant) of the C-terminal LIM domain of CRP2 abolished its binding to MBP-GATA4 (FIG. 4A, lanes 4-6). Retention of the N-terminal LIM domain, even in the presence of partial or complete deletion of the C-terminal LIM domain of CRP2 (in CRP2Δ4 and CRP2ΔC mutants, respectively), was sufficient for robust co-activation of SMA promoter activity (FIG. 4B, lanes 11, 12, 17 and 18). These results revealed three important observations. First, intact LIM motif is obligatory for its function as a protein-protein interface: "half-LIM" is not equivalent to a functional zinc-finger motif, which was known for mediating protein-protein and protein-DNA interaction. Second, the ability of each LIM domain of CRP2 to function independently, with the N-terminal and C-terminal LIM co-associated with SRF and GATA protein, respectively, affirms its adaptor role, as previous studies have suggested (Konrat et al., 1998). Lastly, the N-terminal LIM domain of CRP2 has an important functional role, required for the synergistic transactivation.

CRP2 also co-associated with GATA factors, GATA4 and GATA6, in solution. This interaction is mediated through the C-terminal zinc finger of GATA4 (aa 250 to 304), deduced from the evidence that G4ΔC mutant (lacking aa 336 to 440) co-associated with GST-CRP2 while G4ΔC+ΔZF2 mutant (without aa 250 to 440) did not bind to GST-CRP2 (FIG. 4C). Analysis of the GATA4 mutants in co-activation assays with the SMA promoter also indicated that the C-terminal zinc finger of GATA4 is required for transcriptional activity (FIG. 4D, lane 17). The basic region (aa 305 to 335) of GATA4 was ruled out as a contributor to CRP2-GATA4 association, because G4ZF1+ZF2 (aa 188 to 304) co-associated with GST-CRP2 (FIG. 4C). Deletion of the N-terminal region proximal to the zinc finger revealed an N-terminal activation domain (FIG. 4D, lane 14), while deletion of the N-terminal zinc finger resulted in a strong activation (FIG. 4D, lane 15), consistent with loss of inhibitory activity. It was also confirmed that GATA4 and GATA6 are equivalent in these physical binding experiments (FIGS. 4A and 4C). Together, these physical association and complementary co-transfection analyses identified specific protein-protein interaction domains that are responsible for CRP2-SRF and CRP2-GATA binding.

EXAMPLE 6

CRP2 Dependent Expression of Endogenous SMC Genes

Figure 5:
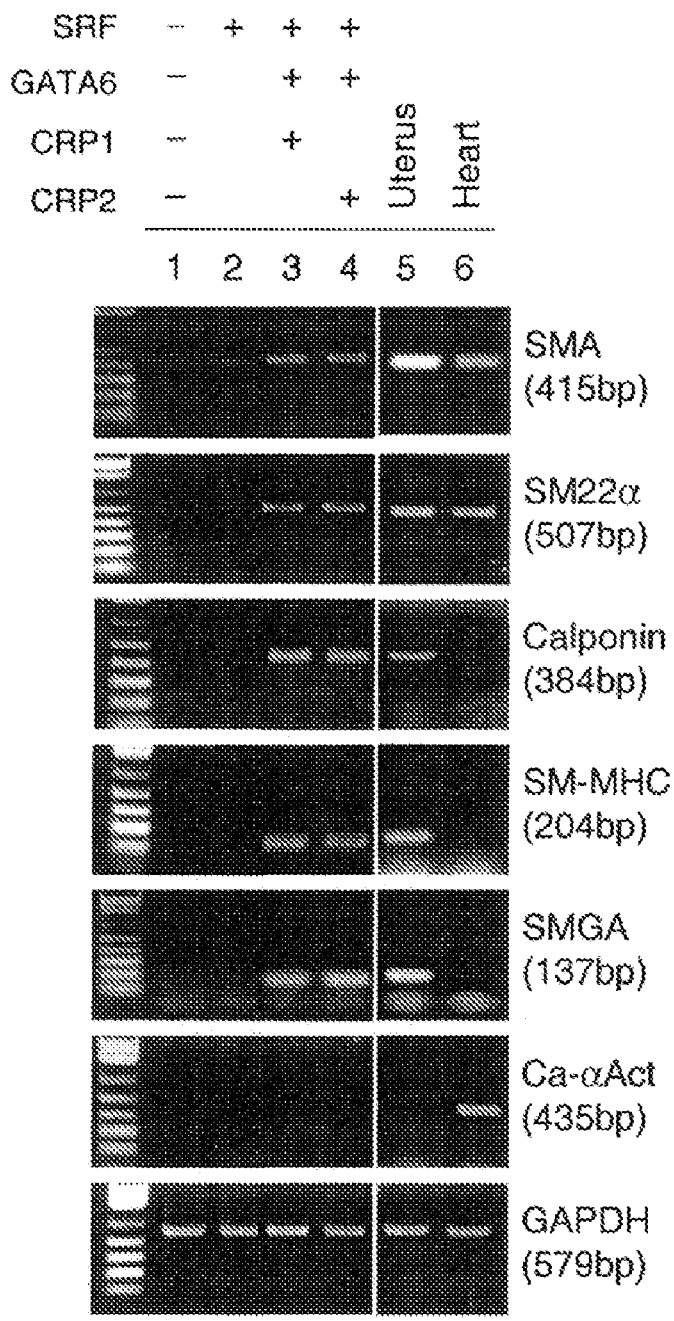
FIGS. 5A through 5C show that co-expression of CRP2, SRF and GATA factors induced endogenous SMC contractile genes.
Figure 5:
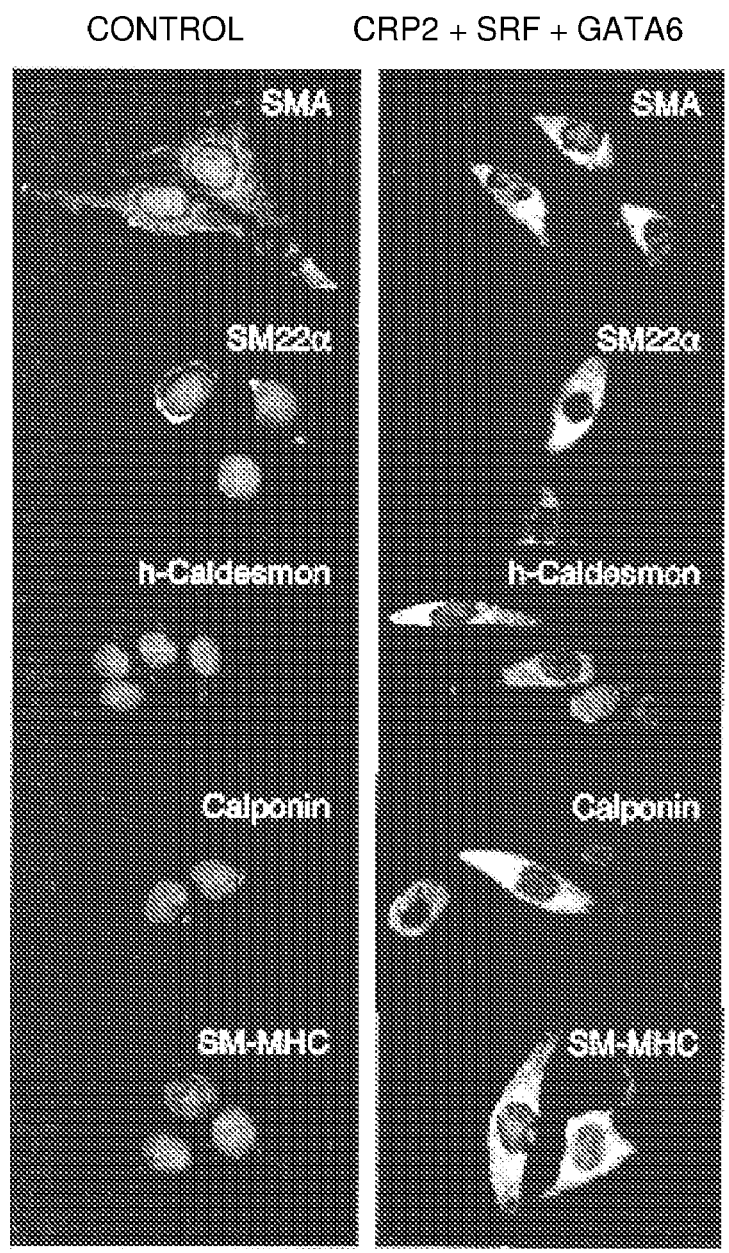
Figure 5:
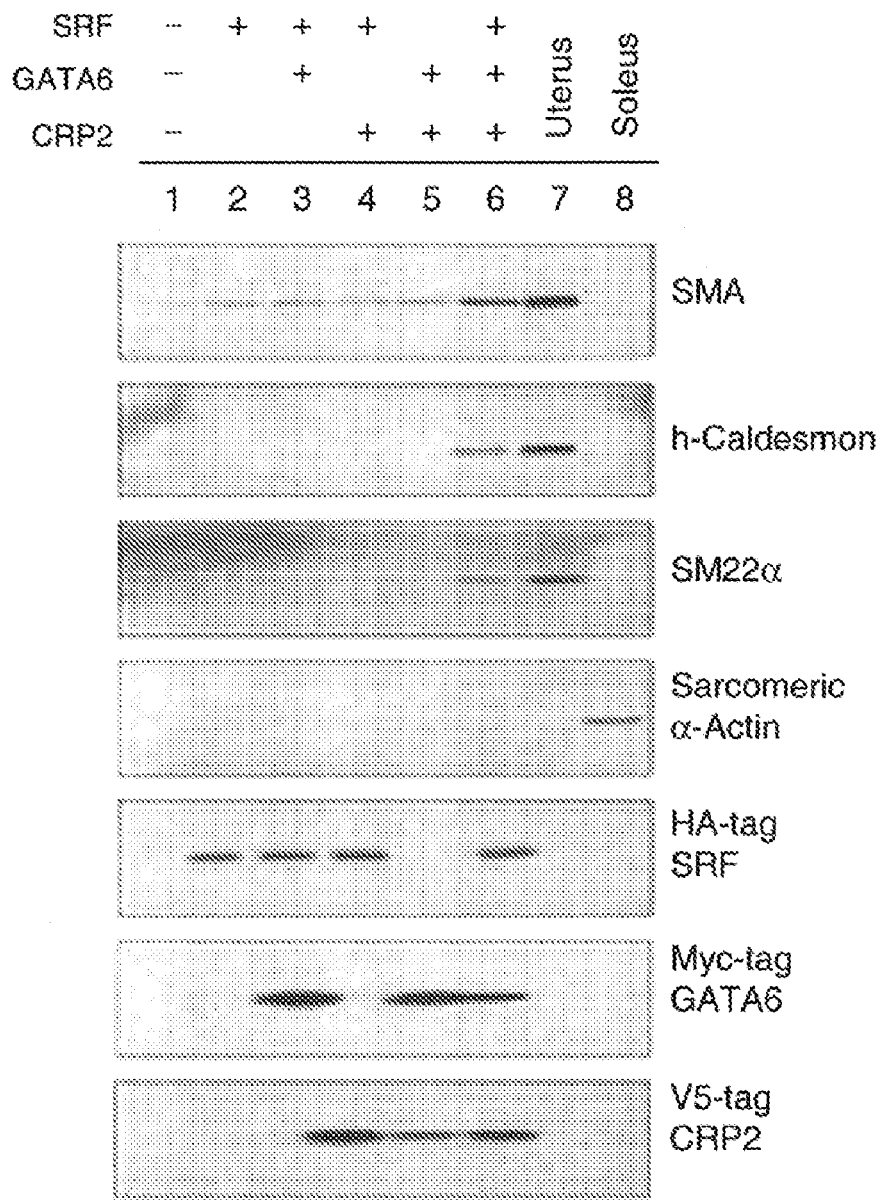

Based on the observation that synergistic interaction among CRP2, SRF and GATA factors produced robust promoter activity, the effects of these transcription factors were tested in combination in murine pluripotent 10T1/2 mesenchymal cells. Within two days following co-transfection with CMV-driven expression plasmids encoding SRF, GATA6, in combination with CRP1 or CRP2 but not CRP3, transcripts encoding SMαA, SM22α, SM-calponin, SM-MHC and SMγA, were detected by RT-PCR assays (FIG. 5A, lanes 3-5). Transfection with SRF alone or with an empty control vector did not result in gene upregulation (FIG. 5A, lanes 1, 2). Also, transfection efficiency (~50%) of individual plasmid expression vectors was not altered greatly in co-transfection experiments and was reduced to only 20% for three plasmid vector co-transfections. Furthermore in this transdifferentiation assay, both immunofluorescence (FIG. 5B) and Western blot (FIG. 5C) analyses have confirmed the expression of each of these SMC specific proteins, including SM-calponin and SM-MHC. Striated muscle-specific sarcomeric α-actin and cardiac α-actin were not induced (FIGS. 5A, 5C), indicating that the differentiation pattern is uniquely SMC-specific. Together, expression of CRP2 with SRF and GATA factors activated a SMC-lineage specific gene program in 10T1/2 cells.

EXAMPLE 7

Figure 6:
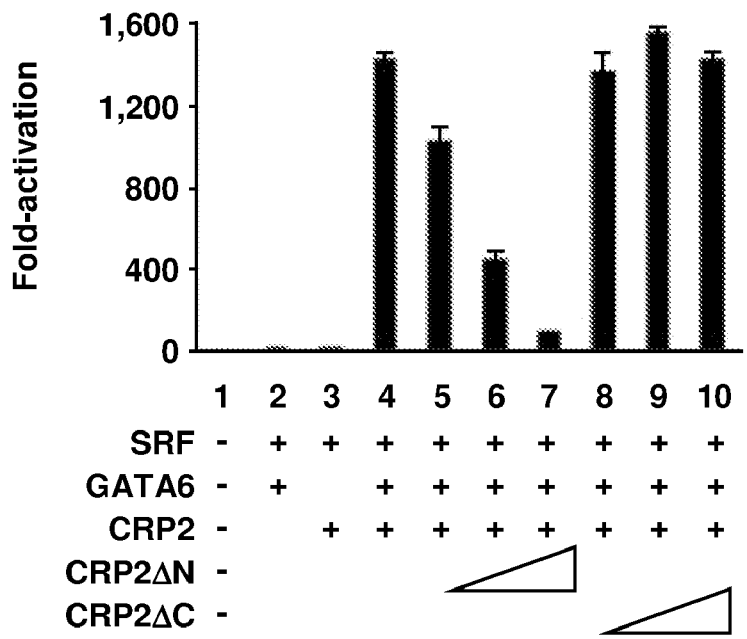
FIGS. 6A through 6B demonstrate that a dominant negative CRP2 mutant blocks vascular smooth muscle differentiation of proepicardial organ (PEO) cells.
Figure 6:
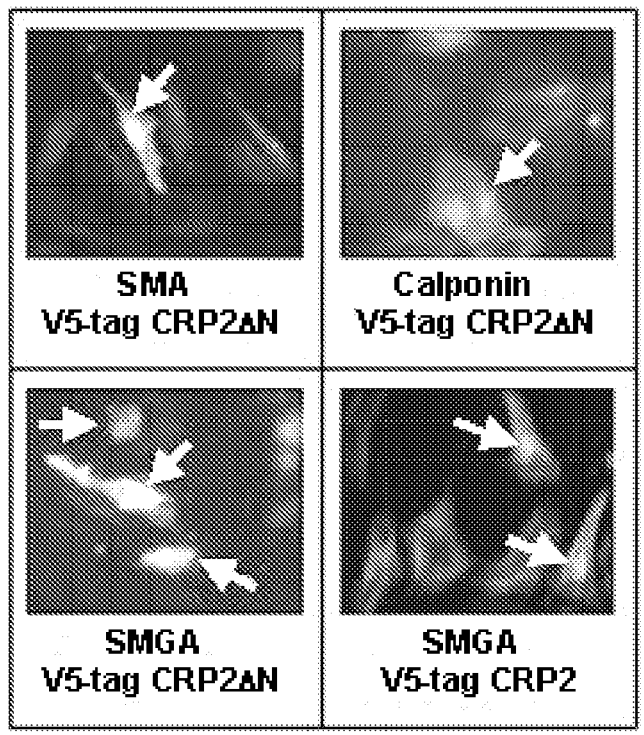

Dominant Negative CRP2 Blocked Vascular Smooth Muscle Differentiation of Proepicardial Cells From the physical mapping of CRP2, it was observed that the CRP2ΔN mutant (aa 112-193) binds strongly with GATA4 but was null for both co-association and co-activation with SRF. To check if CRP2ΔN could act as a dominant negative mutant, cotransfection assays were performed with SRF, GATA6 and wild type CRP2 (FIG. 6A). In a dose-dependent manner, CRP2DN effectively shut down co-activation of SMA-Luc reporter (FIG. 6A, lanes 5-7). The other C-terminal LIM deletion mutant CRP2DC (aa 1-112) had no effect in this co-transfection assay (FIG. 6A, lanes 8-10).

Next, the PEO system was utilized to determine if CRP2 was functionally important for SMC differentiation. Freshly isolated proepicardial cells were transfected with dominant negative CRP2ΔN and examined 2-3 days later for effects on SMC marker protein expression. In each of three independent experiments, transfection of proepicardial cells with CRP2ΔN inhibited vascular smooth muscle differentiation, as determined by expression of the smooth muscle marker genes SMαA, calponin and SMγA (FIG. 6B). Expression of CRP2ΔN inhibited the appearance of calponin-positive cells by 50-70% when compared to untreated or empty vector-treated cells. CRP2ΔN inhibited the appearance of SMαA-positive cells by a similar extent. By comparison, a dominant negative form of SRF inhibited vascular SMC differentiation in this system by about 80% (Landerholm et al., 1999).

EXAMPLE 8

Significance of the Present Invention

In a specific embodiment of the present invention, in progenitor cells undergoing differentiation to promyocardial or prevascular SMCs, CRP1 and CRP2 function as transcriptional co-activators involved in the assembly of multiprotein DNA-binding complexes that contain SRF, GATA factors and/or chromatin remodeling enzymes that collectively mediate SMC-specific gene transcription. In other embodiments, in more fully differentiated SMCs, including SMCs in the mature artery wall, CRP2 plays a scaffold role for assembly and maintenance of a SMC cytoskeleton involved in cell-substrate adhesion and contractile responses to vasoactive stimuli. A cytoarchitectural role of CRP2 is preferably related to the strong binding of the N-terminal LIM domain to cytoskeleton-associated proteins, such as α-actinin and zyxin (Louis et al., 1997; Pomies et al., 1997).

In one aspect of the present invention, CRP1 and CRP2 act as co-adaptor molecules that bridge together two cardiovascular-enriched nuclear factors, SRF and GATA6, into a transcriptosome that confers strong activation of SMC-specific promoters. This strong activation may partly be due to the effect of CRP2 on the DNA binding activities of SRF and GATA6. Highly related striated muscle-restricted protein CRP3/MLP has been shown earlier to potentiate the DNA binding activity of MyoD (Kong et al., 1997). The recruitment of Nkx2-5 and GATA4 by SRF strongly enhanced SRF DNA binding affinity, a mechanism that allowed for the formation of higher ordered cardiac α-actin promoter DNA binding complexes (Sepulveda et al., 2002). Similarly, the combination of GATA4 and CRP2 greatly increased SRF DNA binding affinity and thereby increased the apparent concentration or mass of SRF (FIG. 3C). Further support for the co-adaptor embodiment comes from related LIM only proteins, CRP3/MLP, Lmo2 and Lmo3, which have been shown to assemble transcription factor complexes involved in myogenic, erythrogenic and neurogenic gene regulation, respectively (Kong et al., 1997; Mead, et al 2001; Bao et al., 2000). The three dimensional structure of CRP2 revealed individual LIM domains as independent structural modules separated by a flexible glycine rich linker domain that imposes minimal constraint on freedom of movement of the LIM domains (Konrat et al., 1998). Thus, the ability of nuclear LIM domain proteins and their binding partners to mediate long range interactions among chromosomal regulatory elements (Morcillo et al., 1997; Milan et al., 1998) in specific embodiments enables CRPs to integrate the activities of several factors involved in coordinated regulation of gene expression characteristic of a specific cell type.

Despite extensive similarities in the structure of the N-terminal LIM domains of CRP1/2/3, sufficient divergence in the structure of the C-terminal LIM domains and conformational plasticity of these factors may allow selective recruitment of factors that in turn may determine muscle subtype specificity (Konrat et al., 1998). In support of this notion, all three CRPs bind with similar affinities to α-actinin and zyxin through their N-terminal LIM domains while both the N- and C-terminal LIM domains of CRP2 and CRP3 specifically interact with additional unrelated factors (Louis et al., 1997). The N- and C-terminal LIM domains of CRP3 but not CRP1 and CRP2 bind. MyoD (Kong et al., 1997) and bI-spectrin, respectively (Flick and Konieczny, 2000). Similarly the N- and C-terminal domains of CRP2 specifically interact with the CRP2BP and PIAS1, respectively (Weiskirchen and Gressner, 2000; Weiskirchen et al., 2001). Such subtle differences in the ability of CRPs to recruit distinct regulatory factors may be the basis by which CRPs discriminate among muscle lineages and confer muscle subtype specificity. CRP3/MLP, by being a poor co-activator of smooth muscle gene promoters (FIG. 2A), may also act as a de facto competitive inhibitor of CRP2 dependent gene activity (FIG. 5A).

Figure 7:
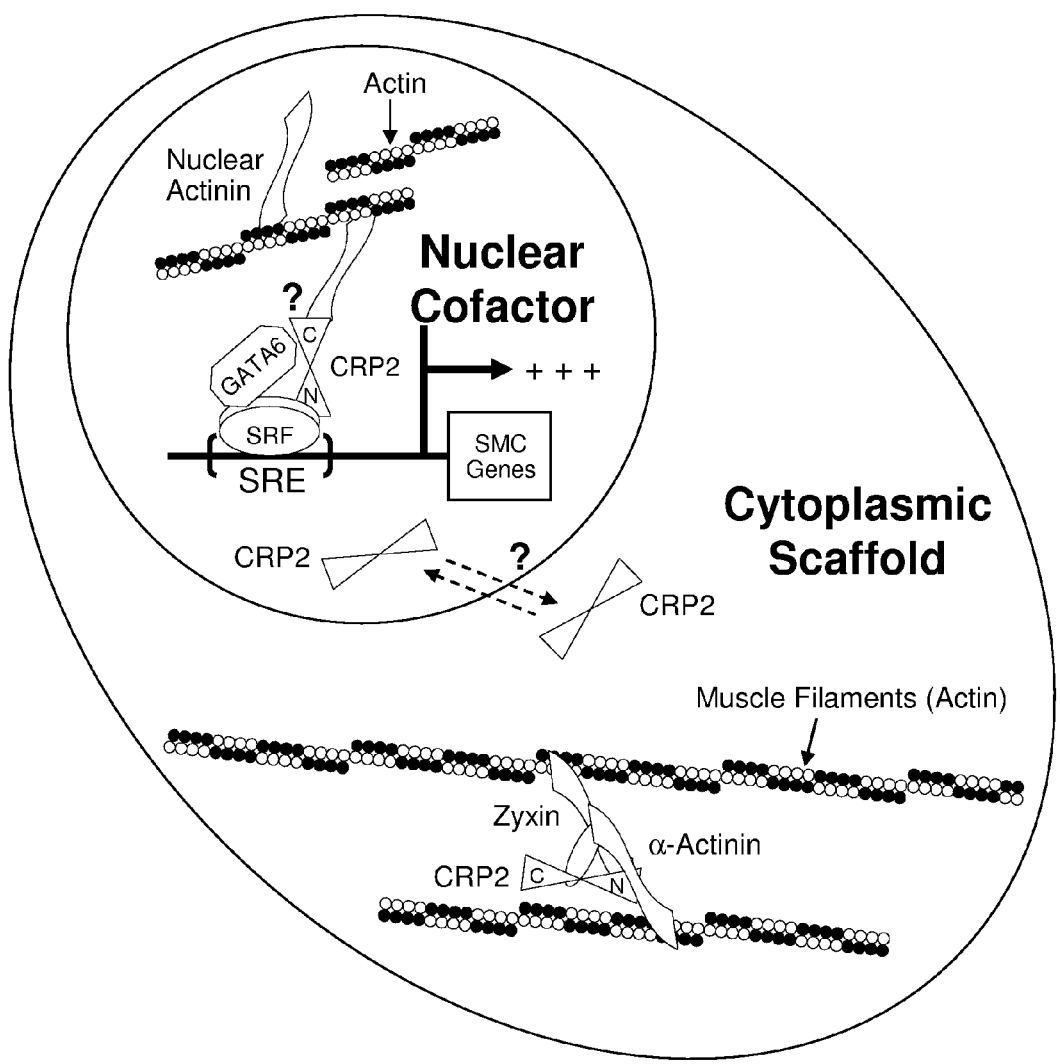
FIG. 7 illustrates an exemplary schematic for the dual roles of CRP2: a LIM-only shuttling protein that functions both as a cytoplasmic scaffold protein and as a nuclear transcription cofactor.

Recently, Rando et al., (2000) proposed that actin localizes to the nuclear matrix. Actin and actin-related proteins may be likely candidates for targeting mSWI/SNF or BAF complexes to selective chromatin domains (Zhao et al., 1998). CRP interacting proteins, such as zyxin and actin itself have been found to contain an NES (nuclear export sequence) and to shuttle between the cytoplasm and nucleus (Nix and Beckerle, 1997; Wada et al., 1998). In specific embodiments, CRPs are involved in chromatin remodeling by being physically associated to an actin based nuclear matrix that shuttles from the cytoskeleton to the nucleus (FIG. 7). Nuclear non-muscle actinins and/or zyxin isoforms might serve as molecular tethers that recruit LIM-associated transcriptosomes to the actin matrix; thus, increasing the local concentration of transcription factors. Short oligomers of actin may lead to placing transcriptosome complexes periodically along a short actin filament (FIG. 7). These actin-based nuclear complexes in essence might form a semi-rigid platform that could help bend or twist chromatin to optimize transcriptional activity. An actin-based nuclear matrix with associated nuclear myosins (Nowak et al., 1997)) may even provide motor activity that twists chromatin. The ability of SRF, GATA6 and CRP2, in combination and not individually, to activate SMC-restricted marker genes such as SMA, SM22α, calponin, caldesmon and SM-MHC (FIG. 5B), may be due to the ability of LIM factors to assemble transcriptosome complexes and facilitate chromatin remodeling.

EXAMPLE 9

De Novo Smooth Muscle Gene Activity is Dependent Upon CRP2 Expression in Adult Cardiac Myocytes As discussed herein, LIM only proteins CRP1 and CRP2 are multifunctional proteins, recently shown to be central for the specification of cardiovascular lineages. CRP1 and CRP2 act as co-adaptor molecules that bridge together two cardiovascular enriched nuclear factors, SRF and GATA4/5/6, into a transcriptosome that confers strong activation of SMC-specific genes. This strong activation in specific embodiments is due to the effect of CRP2 on the DNA binding activities of SRF and GATA6. The combination of GATA factors and CRP2 greatly increased SRF DNA binding affinity and thereby increased the apparent concentration or mass of SRF, making SRF a more powerful transactivator. Further support for the co-adaptor model comes from related LIM only proteins, CRP3/MLP, Lmo2 and Lmo3, which have been shown to assemble transcription factor complexes involved in myogenic, erythrogenic and neurogenic gene regulation, respectively (Kong et al., 1997; Mead, et al 2001; Bao et al., 2000). In addition, each member of the CRP family contains two LIM domains with associated glycine-rich repeats. The three dimensional structure of CRP2 revealed individual LIM domains as independent structural modules separated by a flexible glycine rich linker domain that imposes minimal constraint on freedom of movement of the LIM domains (Konrat et al., 1998). Thus, the ability of nuclear LIM domain proteins and their binding partners to mediate long range interactions among chromosomal regulatory elements (Morcillo et al., 1997; Milan et al., 1998) may enable CRPs to integrate the activities of several factors involved in coordinated regulation of gene expression characteristic of a specific cell type.

During specification of cardiovascular lineages, Gannon and Bader defined a differentiated but non-contractile cardiomyocyte, as a distinct cell type within the cardiac lineage prior to overt cardiomyoblast commitment. De novo gene expression of smooth muscle contractile protein genes occurs during this interval providing molecular markers for promyocardial cells, which coincided well with the appearance of the overlapping expression of CRP1, CRP2 GATA4/5/6 and SRF in early avian embryos. Specific expression of the SMA gene actually marks the onset of differentiation of cardiac cells and represented the first demonstration of coexpression of both smooth muscle and striated α-actin genes within the same myogenic cells, well before the events of looping and maturation to the multichambered heart. Myocardin, another powerful regulator of smooth muscle gene activity, also appears during early cardiovascular development. However, during the onset of rhythmic contractility and formation of cardiac chambers smooth muscle gene activity is switched off in the myocardium, correlating well with the down regulation of both CRP1 and CRP2 in the heart. During this key transition point in the progression from a promyocardial cell type to a differentiated myocyte, myocardin expression is still maintained, while CRP3, an apparent repressor of smooth muscle gene activity, is switched on. Later, CRP1, CRP2 and the smooth muscle gene transcripts reappear in developing organs enriched in smooth muscle, including arteries, stomach, gizzard and intestine/colon.

Repression of CRP1 and/or CRP2 gene activity may be central for the down regulation of smooth muscle gene activity in the heart. In progenitor cells undergoing differentiation into promyocardial or prevascular SMCs, CRP1 and CRP2 appear to function as transcriptional co-activators involved in the assembly of multiprotein DNA-binding complexes that collectively mediate SMC-specific gene transcription. On the other hand, CRPs may also play a scaffold role for assembly and maintenance of a SMC cytoskeleton involved in cell-substrate adhesion and contractile responses to vasoactive stimuli, In addition, a cytoarchitectural role of CRP2 may be related to the strong binding of the N-terminal LIM domain to cytoskeleton-associated proteins such as α-actinin and zyxin (Louis et al., 1997; Pomies et al., 1997). Since, CRP2 cycles in and out of the nucleus, is it possible that when CRP2 is sequestered on the cytoskeleton it is there to simply mask its nuclear regulatory role? Or does CRP2 have another regulatory agenda to foster smooth gene activity by signaling through its association with the cytoskeleton? As described in the following examples, the inventors characterized the idea that CRP2 largely controls the expression of smooth muscle gene activity in the heart and that one reason smooth muscle contractile protein was down-regulated might be due to the diminished levels of potent SMC differentiation factor such as CRP2. If CRP2 protein is re-introduced back to heart cells, will exogenous synthesis of SMC fibers occur? The following examples show that smooth muscle gene activity is dependent upon CRP2 expression to promote de novo upregulation of exemplary smooth muscle specified genes in adult cardiac myocytes. CRP2 has a clear nuclear role, and disruption of the cytoskeleton releases CRP2 to the nucleus and stimulates CRP2 dependent gene activity. Furthermore, the following examples show that inactive smooth muscle genes in adult cardiac myocytes were strongly activated by chromatin remodeling induced by enhanced re-expression of CRP2.

EXAMPLE 10

CRP2 Clearly Plays a Role as Nuclear Transcription Cofactor

Earlier works have identified CRPs' function as scaffolding protein that associate with contractile sarcomeric filaments and with adhesion plaques. The inventors and others, however, have observed that CRPs colocalize in the nucleus, which may play a vital function as transcription coactivators (Arber et al., 1994; Chang et al., 2003; Ecarnot-Laubriet et al., 2000; Kong et al., 1997). In order to further characterize the role of CRP2's subcellular compartmentation, the inventors generated CRP2 fusion construct (FIG. 8A), which contain either: 1) a viral SV40 nuclear localization signal (NLS); 2) a protein kinase inhibitor (PKI) nuclear export signal (NES); 3) sequences encoding the strong repression (SR) domain (aa 1-69) of the mouse Mxi1 gene (Schreiber-Agus et al., 1995); or 4) for control, sequences encoding a single mutation (L19P) of the SR domain (SRpm) that abolishes the ability of SR to interact with Sin3 or repress transcription.

Figure 8:
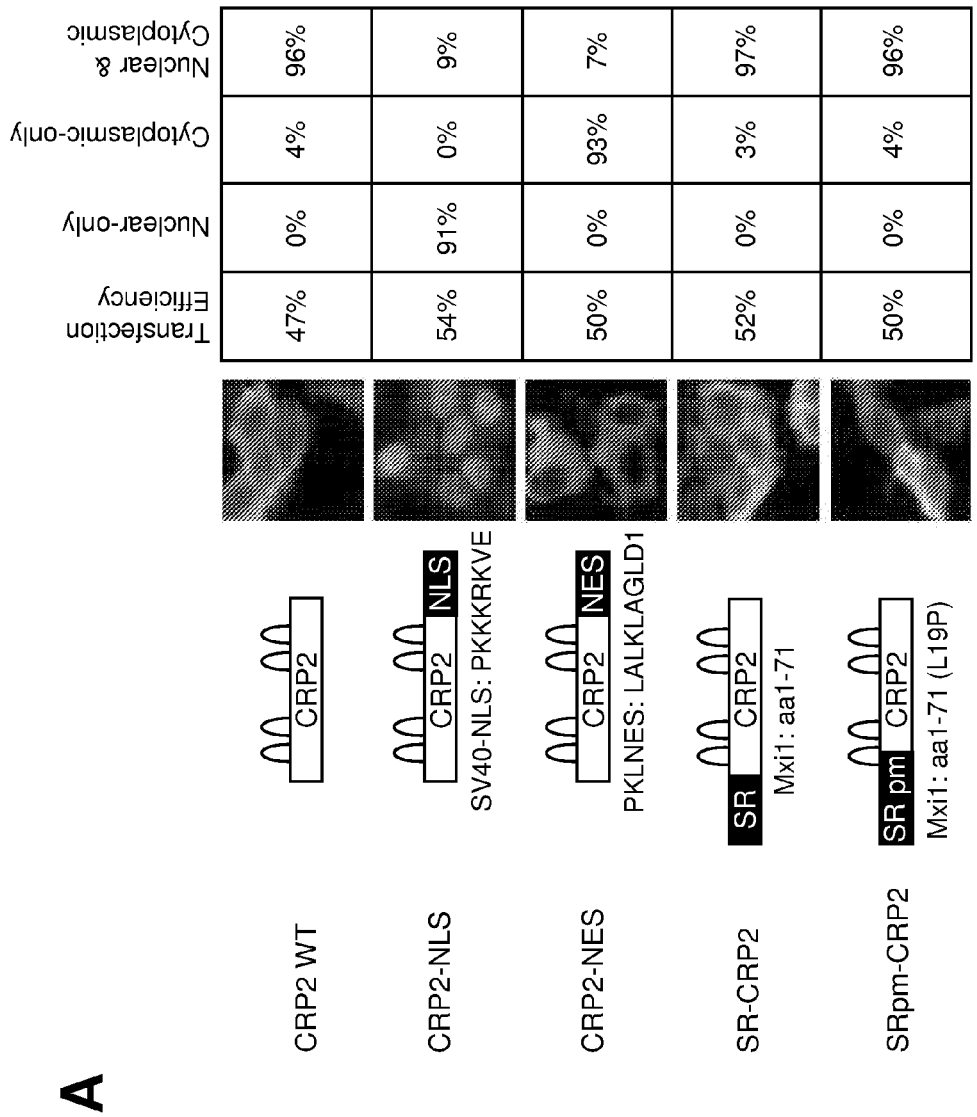
FIGS. 8A-8B show that intra-cellular localization of CRP2 regulates gene transactivation.
Figure 8:
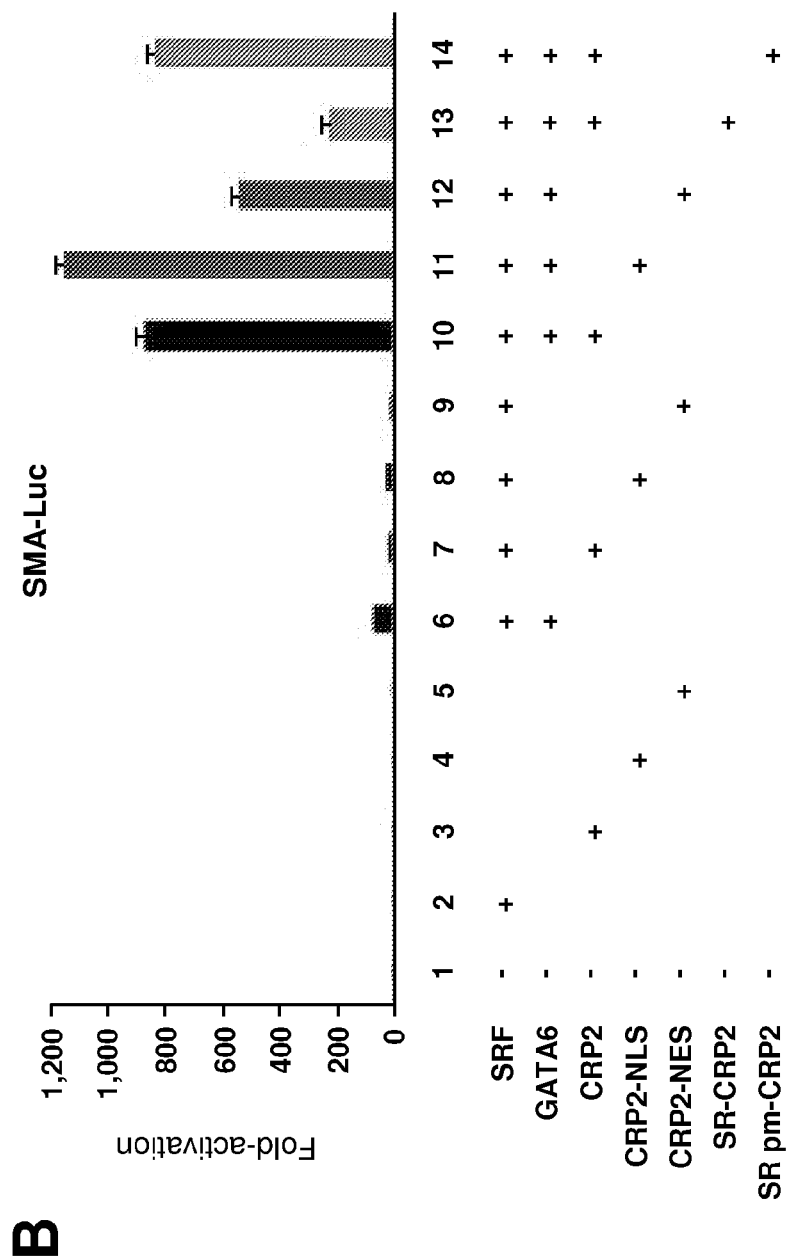

In CV1 fibroblasts, overexpressed wild type CRP2 localizes both in the nucleus and in the cytoplasmic compartments, similar to the subcellular distribution pattern of endogenous CRP2 (Chang et al., 2003). When NLS- or NES-tag is added, the fusion CRP2-NLS or CRP2-NES protein becomes over 90% nuclear- or cytoplasmic-exclusive localized, respectively (FIG. 8A). These reagents allow functional analyses to differentiate nuclear versus cytoplasmic functions of CRP2. As shown in FIG. 8B, co-transfection of CRP2-NLS species with SRF and GATA6 has an increase in transactivation of SMA promoter by 39% (lane II) comparing to CRP2 wild type (lane 10), while substitution with the CRP2-NES vector decreases SMA reporter activation by 37% (lane 12). Nuclear distribution of CRP2 is coincident with reporter gene activation.

To further demonstrate that CRP2's nuclear role is directly involved in gene transactivation, the inventors employed SR-CRP2 construct that acts as a dominant negative species in transcription initiation. Similar to the wild type CRP2, SR-CRP2 is seen both in the cytoplasmic and in the nuclear compartments. When SR-CRP2 coassociates with SRF and GATA6 in SMA gene activation (lane 13), the SR domain interacts with Sin3A, which allows recruitment of corepressors, and thus abolishes synergism seen in wild type CRP2 (lane 10). The SRpm-CRP2 construct, lacking the ability to bind to Sin3A, serves as a control for the SR-fusion domain.

EXAMPLE 11

RHO Kinase Mediated Signaling May be Involved in CRP2 Shuttling

Figure 9:
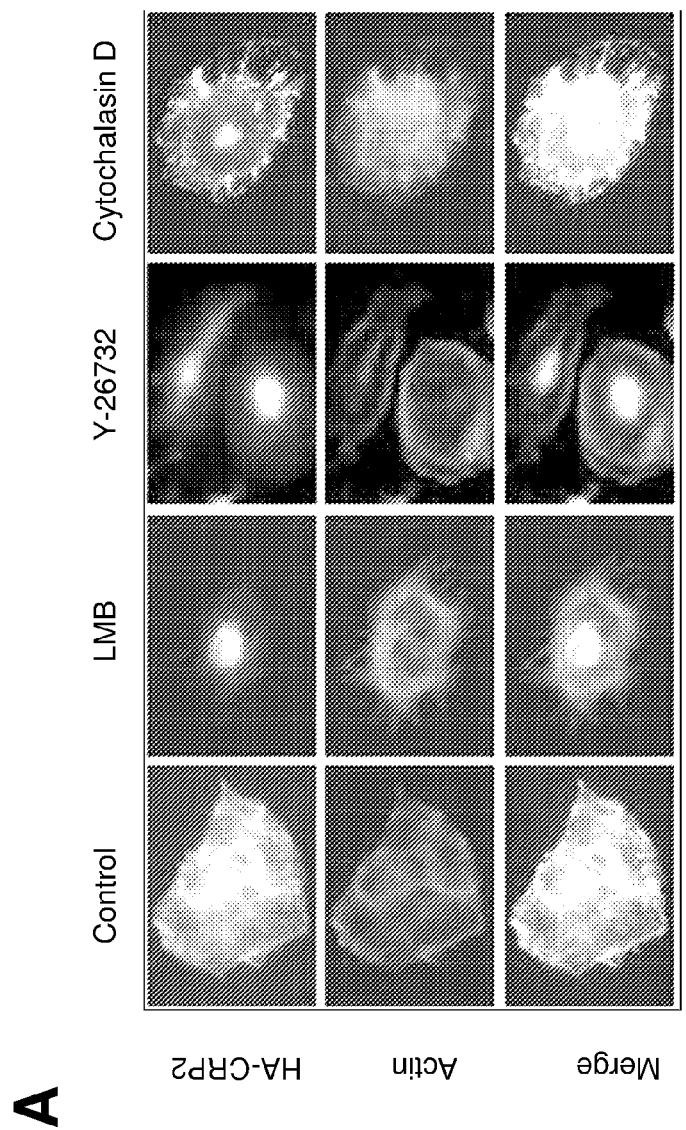
FIGS. 9A-9B show signaling mechanisms involved in CRP2 nuclear localization.
Figure 9:
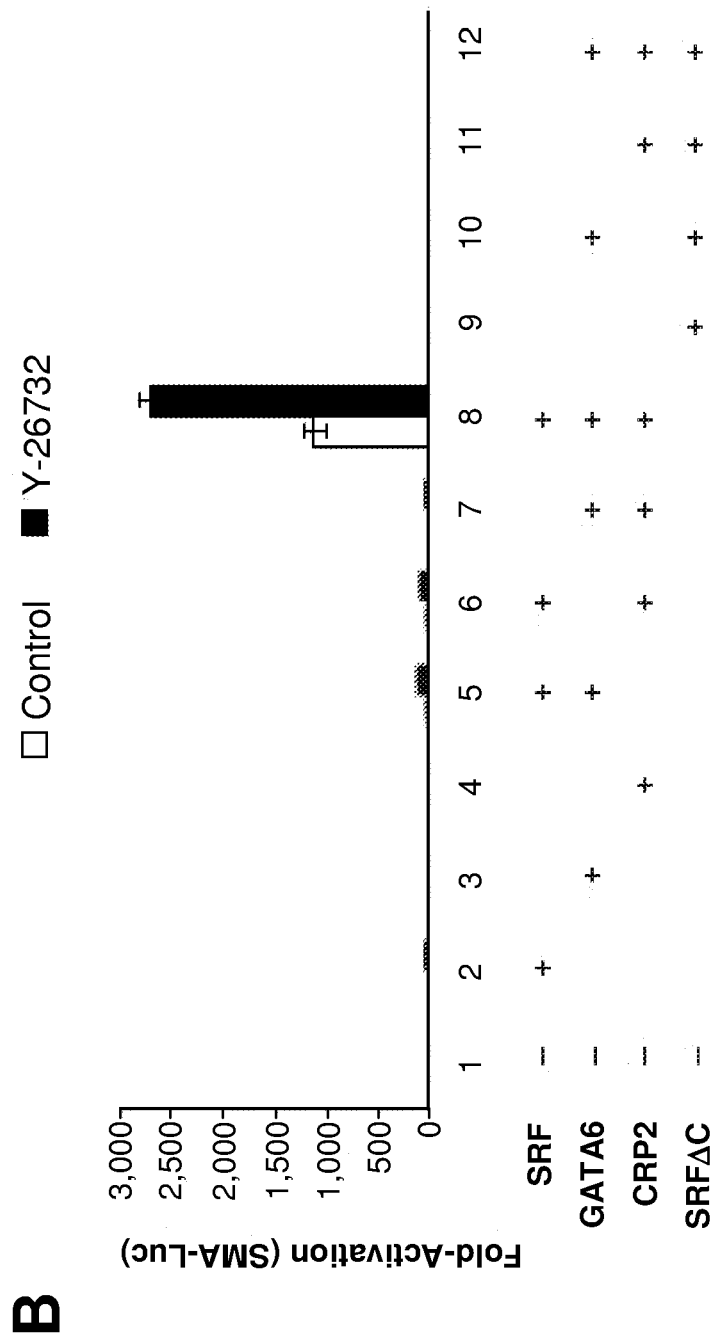

To elucidate the mechanism controlling CRP2 shuttling, the inventors treated transiently transfected monkey CV1 fibroblasts with drugs that either affect cytoskeletal integrity (Y-26732, cytochalasin D, latrunculin B) or are inhibitors of nuclear export (leptomycin B) and looked for changes in the distribution of CRP2. After 2 hr of 10 µg/ml treatment of leptomycin B (LMB), a specific inhibitor of nuclear export signal-dependent nuclear exclusion (Fukuda et al., 1997), 82% of transfected CV1 cells displayed CRP2 accumulation in the nucleus (FIG. 9A). Next, addition of 10 µM of p160-Rho kinase inhibitor, Y-27632, into the growth medium of transfected CV1 fibroblasts resulted in CRP2 nuclear localization in 68% of the cells (FIG. 9A). Nuclear localization of epitope-tagged CRP2 was also observed in cells treated with cytochalasin D (5 µg/ml, FIG. 9A) or latrunculin B (not shown), which completely dissolved the actin cytoskeleton within one hour. These results demonstrate that the cytoarchitecture plays a major role in mediating CRP2 localization.

Drug treatments were examined for effect on gene activation. Twelve hours after cotransfection of CRP2, SRF and GATA6 expression plasmids into CV1 cells, Y-26732 were added to the medium. At various time points (6 h, 12 h, 18 h, and 24 h) post-drug treatment, cell lysates were harvested for luciferase assay. Treatment of the Rho-kinase inhibitor increases SMA gene activation (FIG. 9B), coincident with CRP2 nuclear localization (FIG. 9A). Overall, nuclear localization is important in CRP2's ability to play a role in transcription activation. In a specific embodiment of the present invention, CRP2 functions as a molecular sensor that detects cellular changes.

EXAMPLE 12

Upregulation of Smooth Muscle Target Genes in the Adult Heart of αMHC-CRP2 Transgenic Mice Previously the inventors have reported combinatorial overexpression of CRP2, SRF and GATA6 in fibroblast cells is sufficient and necessary for SMC gene expression (Chang et al., 2003). In heart, SRF and GATA factors 4 and 6 are present from embryogenesis through adulthood, while CSRP2 is expressed only transiently during early development. Cardiomyocytes in the primitive contractile linear tube show SMC-like phenotype and expressed SMC markers such as SMA. Though later down-regulated, CRP2 may be essential for the synthesis of SMA in primitive cardiomyocytes, in specific embodiments of the present invention. Smooth muscle contractile protein gene activity in the heart was examined for dependency upon the expression of CRP2. If CRP2 protein is re-introduced back to heart cells, will exogenous synthesis of SMC fibers occur?

Figure 10:
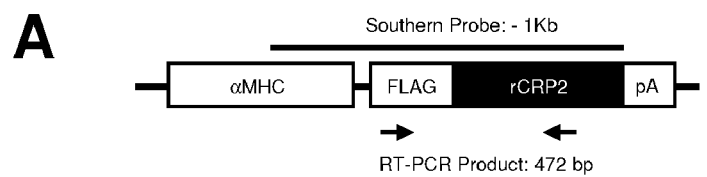
FIGS. 10A-10D show cardiac-specific overexpression of CRP2 in αMHC-CRP2 transgenic mice results in stable production of SMC filaments.
In FIG. 10E, western blot analysis shows expression of cardiac specific markers (cardiac troponin T and sarcomeric α-actin) and transcription factors (SRF, GATA6, and Nkx2-5) in adult hearts of aMHC--CRP2 mice.
Figure 10:
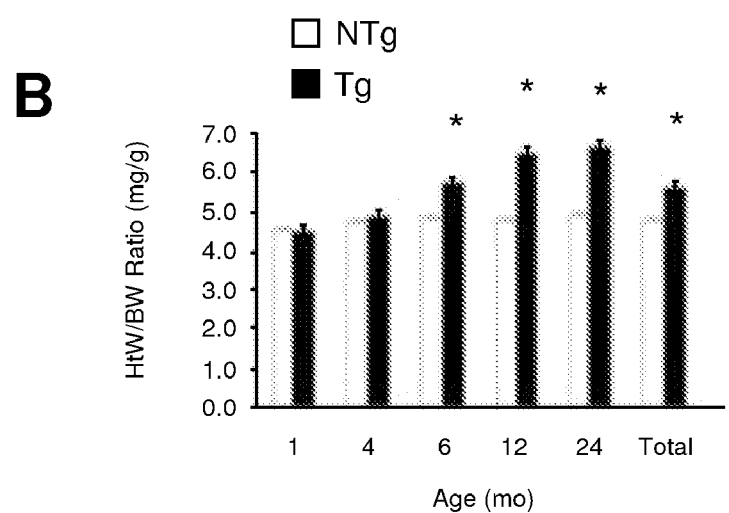
Figure 10:
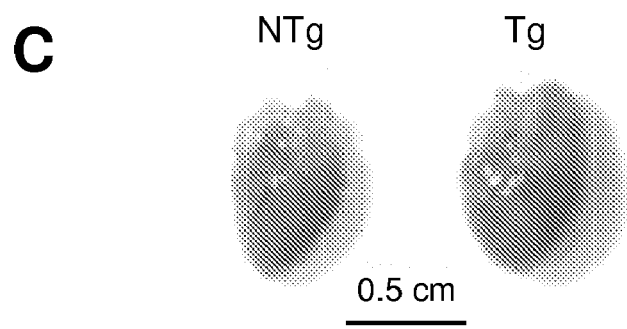
Figure 10:
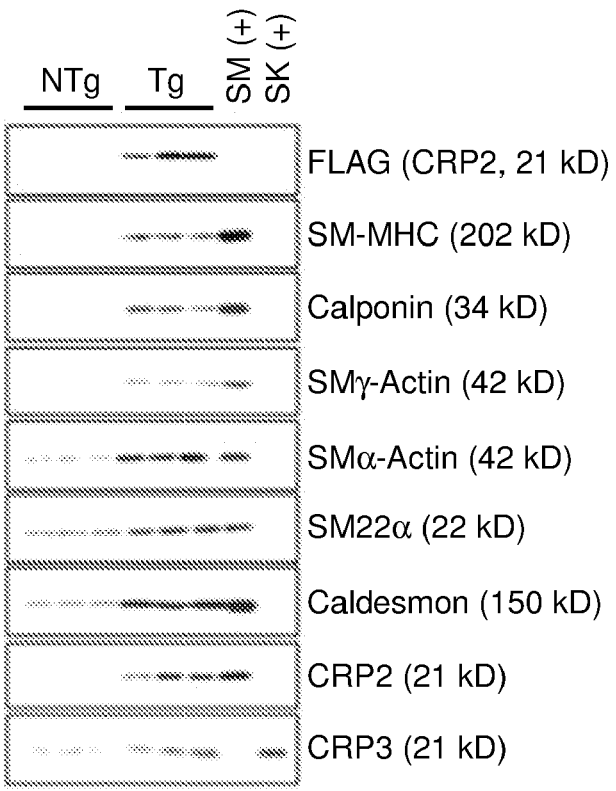
Figure 10:
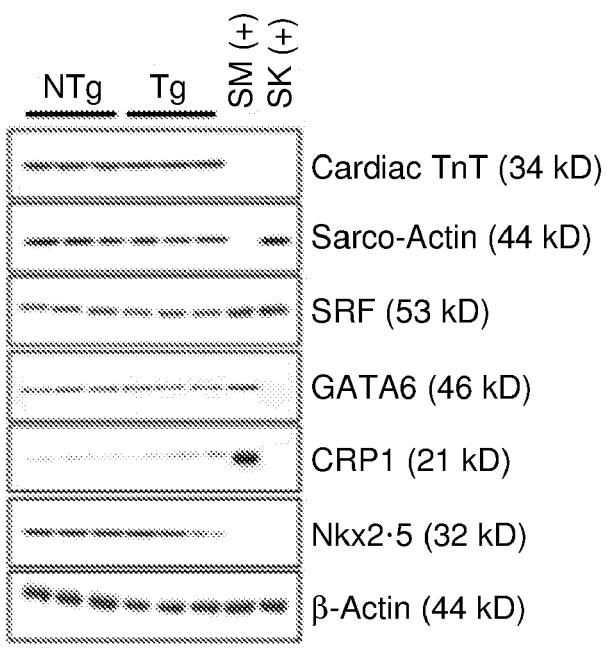

This was investigated at the organismal level, and FIG. 10A shows misexpression of CRP2 in adult heart of transgenic mice leads to exogenous re-expression of SMC contractile proteins. FLAG epitope-tagged rat CRP2 cDNA transgene was driven by the α-myosin heavy chain (α MHC) promoter in embryonic and adult hearts. Two founder lines with highest copy number of transgenes were chosen to establish subsequent colonies. Mice were screened by Southern blot analysis and confirmed by detection of both mRNA (RT-PCR) and protein products (FIG. 10C) of the transgene in the hearts of positive animals. Twelve pairs of transgenic (Tg) and non-transgenic (NTg) littermates, ages range from 4-wk, 15-wk, 6-mo, 1-yr and 2-yr, were examined for heart-weight to body-weight (HtW/BW) ratio in order to assess sign of cardiac hypertrophy (FIG. 10B). There is a slight but statistically significant increase in HtW/BW ratio in transgenic animals over the age of 4 mo. Moreover, these older transgenic animals harbored morphologically larger hearts (FIG. 10C). However, careful histological examination empolying Masson's trichrome staining indicated no chamber dilation nor increase in ventricular wall thickness nor any sign of interstitial fibrosis in the heart of transgenic mouse.

To profile the effects of CRP2 misexpression in the heart, the expression level of several SMC and cardiac marker genes was examined. Protein lysates and total RNA were collected from the ventricular portion of the hearts from 3 pairs of transgenic and non-transgenic littermates, and subsequently analyzed by Western immunoblot analysis (FIG. 10D). Equal loadings of protein were shown by α-actin staining. FLAG-CRP2 appeared specifically in the transgenic but not in the non-transgenic hearts. SMC-specific contractile filaments such as SM-MHC, calponin, SM α-actin, SM α-actin, SM22 α and caldesmon were upregulated in the transgenic hearts, while cardiac specific markers (cardiac troponin T and sarcomeric α-actin) and transcription factors (SRF, GATA6, and Nkx2-5) were not affected. CRP1 proteins in the hearts remained at basal level in transgenic mice, even though RT-PCR analysis indicated a slight increase at the mRNA level. CRP2 is normally absent in NTg adult myocardium. On the other hand, CRP3 is augmented in transgenic hearts, a possible compensatory response to CRP2 misexpression. RT-PCR analysis revealed no other alteration in marker genes for cardiac hypertrophy (α-myosin heavy chain, skeletal α-actin, atrial natriuretic factor), calcium handling (SERCA2, phospholamban) transcription factors (myocardin, MEF2C, GATA4, dHAND), or immediate early gene, c-Fos.

Though the increased heart-weight to body-weight ratio in transgenic animals is statistically significant and may indicate cardiac hypertrophy, possibly due to exogenous upregulation of SMC contractile filaments, in specific embodiments, careful histological examination should elucidate other pathophysiological conditions such as cardiac dilation or fibrosis. Cardiac samples were harvested from transgenic and non-transgenic littermates and age-matched C57 wild type mouse of 6 mo old, the starting age of increased HtW/BW ratio. Coronal sections of the heart, showing all four chambers, were subject to Masson's trichrome staining, which stains muscle cytoplasm red, collagen green and nucleus blue. No chamber dilation or increase in ventricular wall thickness were found in 3 transgenic animals examined. The cardiomyocytes of α MHC-CRP2 mice were homogenous in size and not much larger than those of non-transgenic animals. Furthermore, Masson's trichrome staining did not revealed any sign of interstitial fibrosis in the heart of transgenic mouse.

EXAMPLE 13

CRP2 Directs Production of SMC Specific Filaments in Heart Cells

Figure 11:
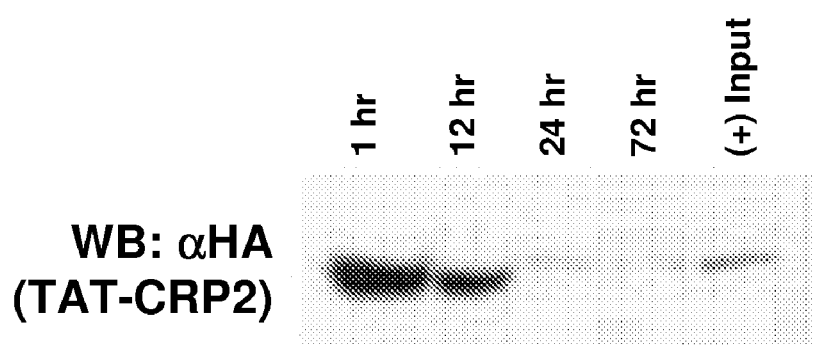
FIGS. 11A-11E show that protein transduction of recombinant TAT-CRP2 into neonatal cardiomyocytes induces upregulation of SMC genes.
Figure 11:
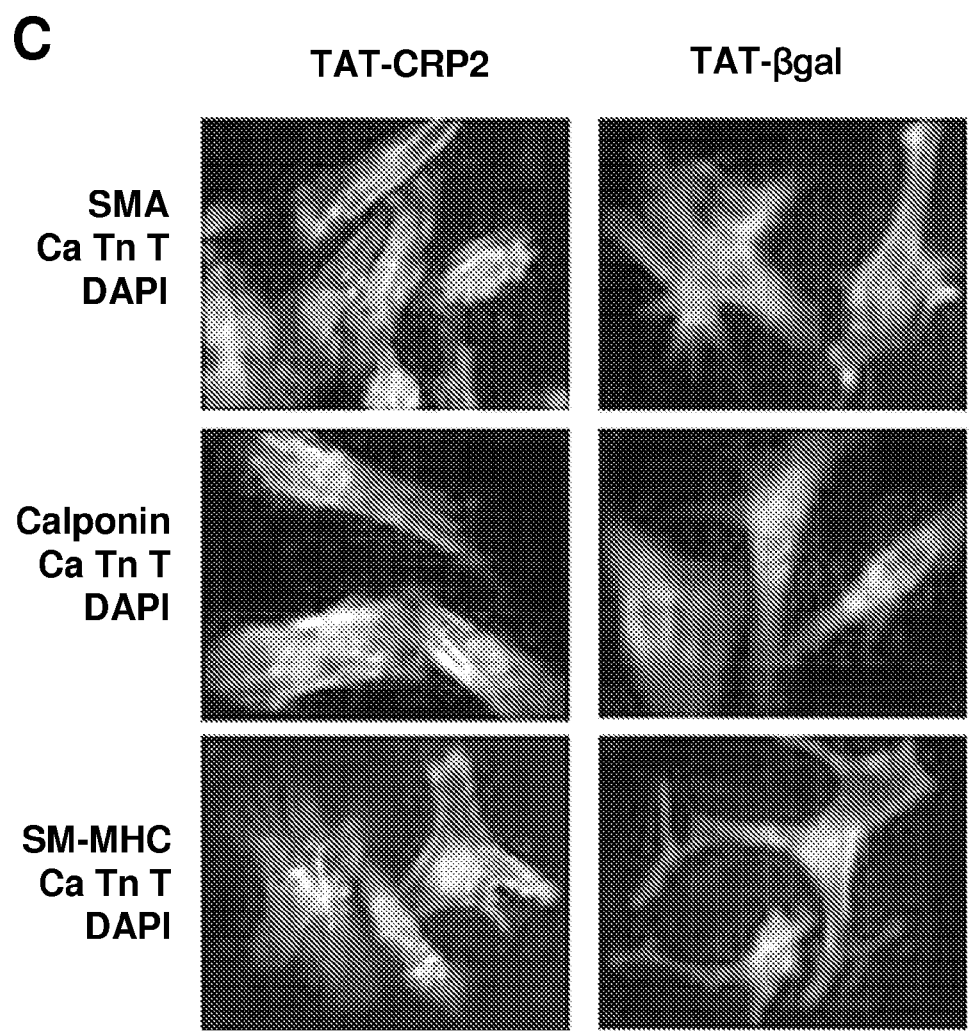
Figure 11:
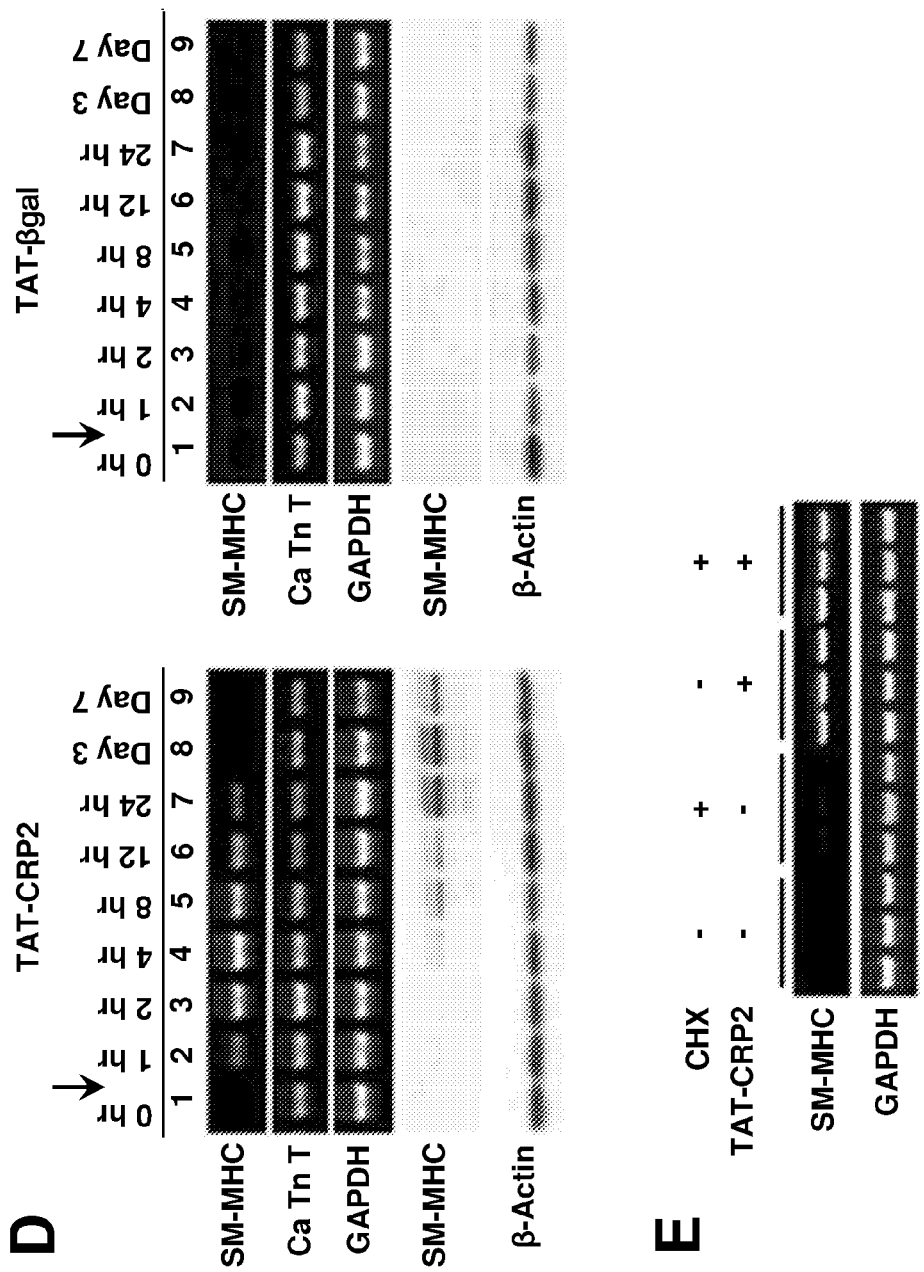

Previous in vivo mouse model demonstrated induction of SMC phenotype when CRP2 is overexpressed in cardiomyocytes. Tissue culture studies were then used to further characterize at the mechanistic level this differentiation event. Since primary tissue culture cells such as heart cells are impervious to DNA transfection, a recombinant CRP2 protein, fused to the exemplary protein transduction domain (PTD) from the human immunodeficiency virus (HIV) TAT protein, was generated (FIG. 11A) following methods described by Steven Dowdy's laboratory (Nagahara et al., 1998). The recombinant TAT-PTD-CRP2 proteins were added to tissue culture medium incubating freshly isolated neonatal cardiomyocytes. Protein transduction occurs in a rapid (<15 min), efficient (~99.9%), and concentration dependent fashion. The PTD is able to target and transverse eukaryotic lipid bilayer, independent of receptor, endosome or transporter pathway [Reviewed in (Schwarze et al., 2000)]. Western blot analysis demonstrated protein transduction of TAT-CRP2 into cardiomyocytes within an hour (FIG. 11B). Although the transduced proteins were rapidly degraded within 24 hr, nevertheless, TAT-CRP2, but not control TAT-βgal, induced upregulation of SMC contractile proteins, including SMA, calponin and SM-MHC, in neonatal rat cardiac cells harvested three days after treatment (FIG. 11C).

In a time course analysis, the acute and potent induction of SM-MHC was further confirmed in response to TAT-CRP2 treatment (FIG. 11D). Though SM-MHC mRNA level leveled off after 24 hr, coincident with TAT-CRP2 depletion in cardiomyocytes, SM-MHC protein was stably maintained up to 7 d, possibly due to slow turn-over rate of the thick filament. Studies performed in the presence of the protein synthesis inhibitor, cyclohexamide, showed that the rapid effects obtained for SM-MHC occur independently of de novo protein synthesis (FIG. 11E). This means, in cardiac cells, which already expressed SRF and GATA6, differentiation cofactor CRP2 alone can potentiate SMC gene program.

EXAMPLE 14

In Vivo Evidence of CRP2 Interactions

Figure 12:
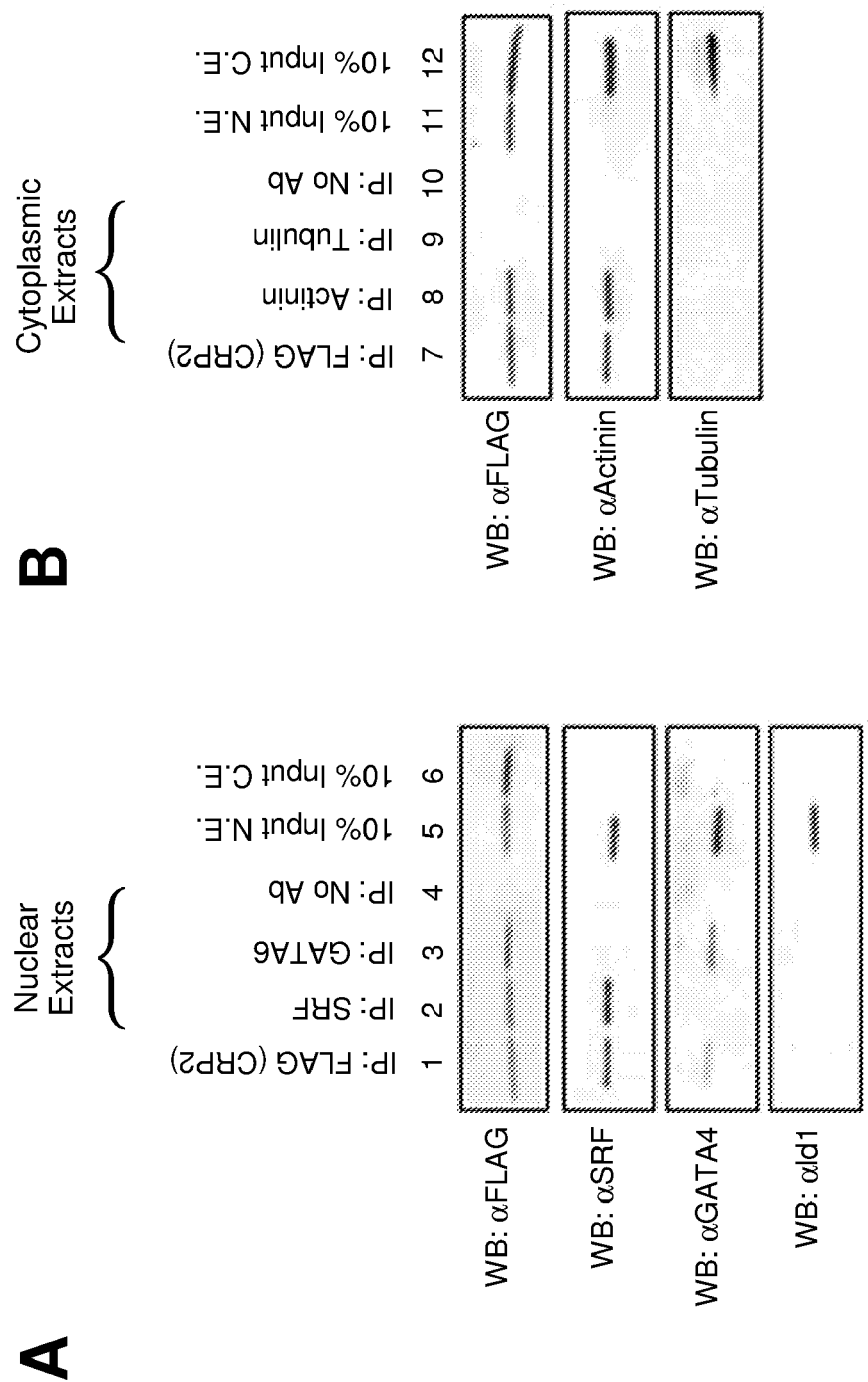
FIGS. 12A-12D show that CRP2 coassociates with nuclear transcription factors, cytoplasmic structural protein and chromatin remodeling complexes.
Figure 12:
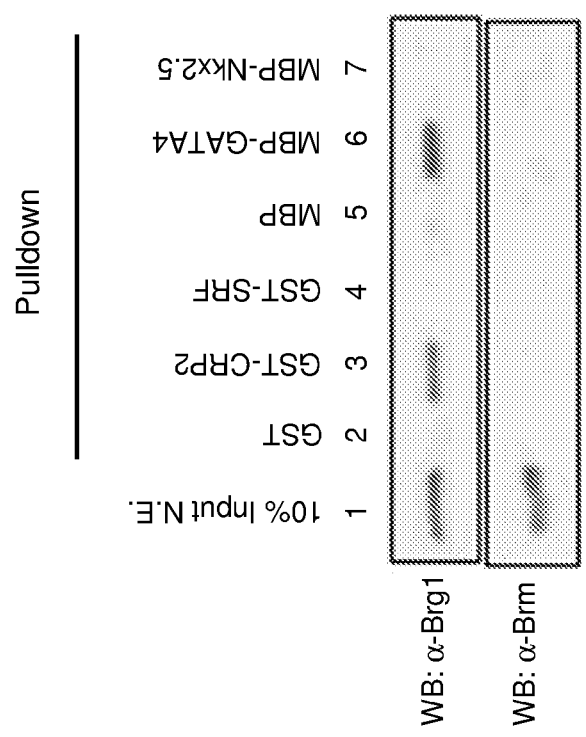
Figure 12:
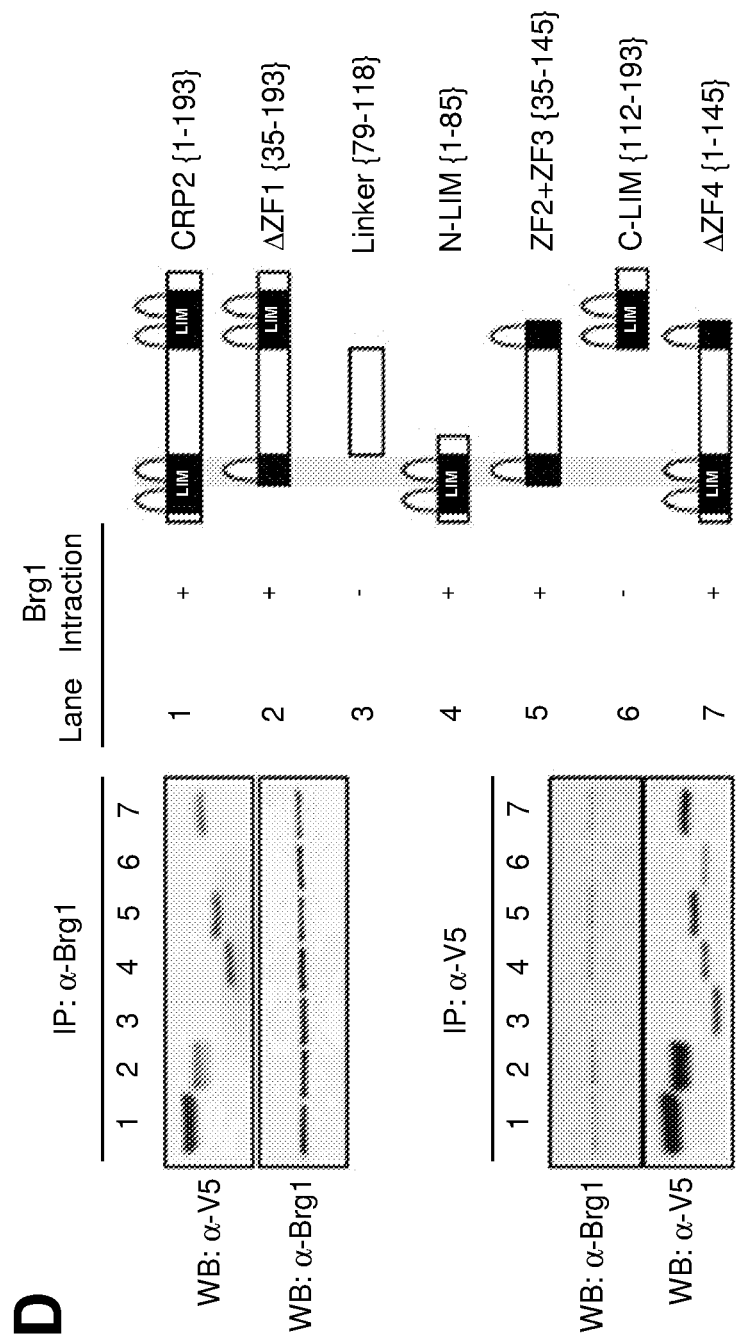

The transgenic CRP2 mice could be a valuable tool for validating previous in vitro protein-protein studies. In adult heart, cardiomyocytes comprise only ~20% of the organ mass, and many nuclear transcription factors are present in low, basal quantities. In vivo co-immunoprecipitation (co-IP) was accomplished by enriching the starting materials in two steps. First, several whole heart were homogenized and centrifuged briefly to remove extracellular components. Cell pellet was then lysed and harvested separately for cytoplasmic and nuclear extracts. Antibodies specific for endogenous SRF and GATA6 or polyclonal antibody against FLAG-tagged CRP2 were used for co-IP, using the concentrated nuclear extracts (FIG. 12A). Since CRP2 is now known to have dual functions both in the nucleus and in the cytoplasm, co-IP utilizing the enriched cytoplasmic extracts was performed to pull out interacting partner of CRP2 in vivo (FIG. 12B). As shown in the immunoblot analysis, CRP2-SRF and CRP2-GATA6 coassociate with each other. (FIG. 12A, lanes 1, 2 and 3), while none coprecipitated with an endogenous cardiac bHLH transcription factor, Id1, demonstrating that these in vivo interactions are specific. Interestingly, SRF and GATA4 do not coasoociate in this in vivo assay, although numerous in vitro experiments have demonstrated these factors' interactions (Belaguli et al., 2000; Chang et al., 2003). Overexpressed CRP2, however, can co-immunoprecipitate with other important nuclear transcription factors in the adult heart, including Nkx2-5, Tbx5 and dHAND. This validates a recent discovery about a multimeric complex regulating cardiac α-actin gene expression (Wang et al, 2003, manuscript in preparation). The versatile CRP2 is also able to bind specifically with the endogenous cytoplasmic α-actinin, but not α-tubulin (FIG. 12B, lanes 7, 8 and 9), confirmed its role as a thin filament scaffold in vivo.

The potent SMC differentiation potential of CRP2 makes us wonder whether chromatin remodeling event is involved in this dramatic activation. Several reports have established that Brg1 and Brm ATPase of the SWI/SNF chromatin remodeling complexes, through selective association with certain classes of transcription factors, plays critical role in cellular differentiation (Kadam and Emerson, 2003; Kadam et al., 2000). In particular, Brg1 SWVSNF complexes were shown to coactivate β-globin transcription by zinc-finger containing factors such as EKLF and GATA1 (Kadam and Emerson, 2003). In specific embodiments of the present invention, the LIM domain of CRP2, which consists of two tandemly attached zinc-finger motifs, can interact with chromatin remodeling complexes. CRP2, as well as zinc-finger GATA4, was capable of "pulling down" endogenous Brg1, but not Brm, complexes in the cardiomyocytes (FIG. 12C). In contrast, MADS-box protein SRF and homedomain factor Nkx2-5 do not coassociate with Brg1 or Brm complexes.

The specificity of Brg1-containing SWI/SNF for LIM domain of CRP2 was further studied. Different V5-tagged CRP2 deletion constructs were transfected into C2C12 mouse myoblasts. The second zinc-finger of CRP2 LIM domain was fine-mapped to be required for the in vivo interaction with Brg1 (FIG. 12D).

EXAMPLE 15

CRP2 Binds to the Endogenous Cis-Elements of Upregulated SMC Target Genes

Figure 13:
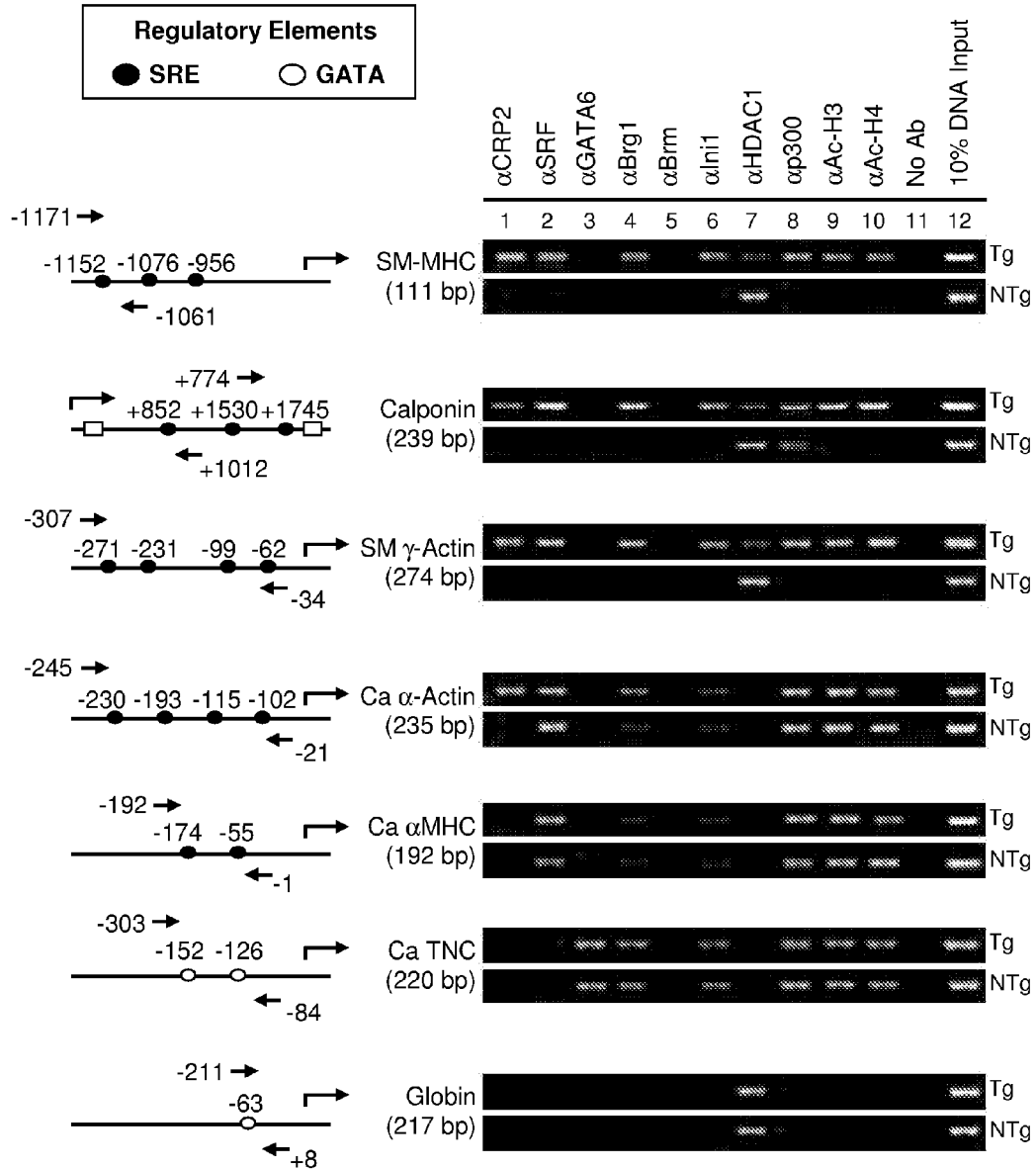
FIG. 13 shows promoter-specific recruitment of CRP2, SWI/SNF complexes and chromatin modifiers in transgenic cardiomyocytes. Chromatin immunoprecipitation (ChIP) analyses of transcriptional activators (CRP2, SRF, GATA6; lanes 1-3), SWI/SNF remodeling complexes (Brg1, Brm, core subunit Ini1; lanes 4-6), chromatin coactivators/corepressors (HDAC1, p300; lanes 7 and 8), and histone modifications (Ac-H3, ACH4; lanes 9 and 10) were performed using a variety of promoters (schematic on the left) which are either exogenously upregulated (SM-MHC, calponin, and SM γ-actin), constitutively activated (Ca α-actin, Ca αMHC and Ca TnT), or permanently inactivated (β-globin) in the heart cells. Briefly, cardiomyocytes from αMHC-CRP2 transgenic (Tg) or non-transgenic (NTg) littermate mice were harvested and treated with formaldehyde to crosslink DNA. DNA recovered from immunoprecipitated samples using specific antibodies (lane 1-10) or no antibody negative control (lane 11) was subjected to PCR amplification, employing primers directed against different promoters. Amplification products contain the regulatory sequence elements (CArG boxes or GATA binding sites) were shown schematically in the top box. Genomic DNA input (10%, lane 12) was included as a positive control.

In a similar manner, the protein-DNA interactions in vivo were studied. The same immunoprecipitation techniques utilized to extract out endogenous and epitope-tagged transgenic trans-factors can also be used to pull out cis-elements bound by these nuclear factors. Chromatin immunoprecipitation (ChIP) was performed, which detects binding of transcription factors to target sites in the genome (FIG. 13). Several hearts were collected from αMHC-CRP2 mice. After homogenizing and centrifugation steps, concentrated cardiomyocytes were treated with formaldehyde, and cross-linked chromatin was sonicated into ~400 bp fragments and subjected to chromatin immunoprecipitation with antibodies against FLAG epitope-tagged CRP2, SRF, GATA4 and acetylated-H4 histone. Immunoprecipitated protein-DNA extracts were reverse cross-linked and purified for DNA fragments. Chromatins eluted were used in PCR amplification of the target sequences. Anti-FLAG and anti-SRF antibodies specifically enriched 5'-flanking regions of upregulated SMC markers (SM-MHC, calponin, SM γ-actin) embedded with previously characterized CArG elements. Anti-FLAG antibody was also able to pull out promoter fragments of some activated cardiac genes, including ANP and cardiac α-actin, but not αMHC, cardiac troponin C, skeletal α-actin, or c-fos. Regions upstream of ANP and cardiac troponin-C contain GATA binding elements. These chromatin fragments were amplified from ChIP assays using anti-GATA4 antibody. Acetylation of histone H4 plays a central role in chromatin remodeling and activation of endogenous genes. All marker genes examined, except globin, were expressed in the cardiac tissue of αMHC-CRP2 mice, and thus enriched in anti-acetylated-H4ChIP assay.

References

All patents and publications mentioned in the specification are indicative of the levels of those skilled in the art to which the invention pertains. All patents and publications are herein incorporated by reference in their entirety to the same extent as if each individual publication was specifically and individually indicated to be incorporated by reference.

Publications

Arber, S., and Caroni, P. (1996). Specificity of single LIM motifs in targeting and LIM/LIM interactions in situ. Genes Dev 10, 289-300.

Arber, S., Halder, G., and Caroni, P. (1994). Muscle LIM protein, a novel essential regulator of myogenesis, promotes myogenic differentiation. Cell 79, 221-231.

Arber, S., Hunter, J. J., Ross, J., Jr., Hongo, M., Sansig, G., Borg, J., Perriard, J. C., Chien, K. R., and Caroni, P. (1997). MLP-deficient mice exhibit a disruption of cardiac cytoarchitectural organization, dilated cardiomyopathy, and heart failure. Cell 88, 393-403.

Arsenian, S., Weinhold, B., Oelgeschlager, M., Ruther, U., and Nordheim, A. (1998). Serum response factor is essential for mesoderm formation during mouse embryogenesis. Embo J 17, 6289-6299.

Bao, J., Talmage, D. A., Role, L. W., and Gautier, J. (2000). Regulation of neurogenesis by interactions between HEN1 and neuronal LMO proteins. Development 127, 425-435.

Belaguli, N. S., Zhou, W., Trinh, T., Majesky, M. W., and Schwartz, R. J. (1999) Dominant negative murine serum response factor: Alternative splicing within the activation domain inhibits transactivation of serum response factor binding sites. Mol Cell Biol 19, 4582-4591.

Belaguli, N. S., Sepulveda, J. L., Nigam, V., Charron, F., Nemer, M., and Schwartz, R. J. (2000). Cardiac tissue enriched factors serum response factor and GATA-4 are mutual coregulators. Mol Cell Biol 20, 7550-7558.

Colas, J F, Lawson, A., Schoenwolf, G. (2000) Evidence that translation of smooth muscle alpha actin mRNA is delayed in the chick promyocardium until fusion of the bilateral heart forming regions. Dev, Dyn. 218, 218, 316-330

Chang, K. S., Zimmer, W. E., Jr., Bergsma, D. J., Dodgson, J. B. and Schwartz, R. J. (1984) Isolation and characterization of six different chicken actin genes. Mol. Cell. Biol. 4:2498-2508.

Dawid, I. B., Toyama, R., and Taira, M. (1995). LIM domain proteins. C R Acad Sci III 318, 295-306.

Dugaiczyk, A., Haron, J. A., Dennison, O., Stone, E. M., Rothblum, K. N. and Schwartz, R. J. (1983) Cloning of a DNA copy of glyceraldehyde-3-phosphate dehydrogenase messenger RNA isolated from chicken muscle: complete nucleic acid sequence of coding region. Biochemistry 22:1605-1613

Flick, M. J., and Konieczny, S. F. (2000). The muscle regulatory and structural protein MLP is a cytoskeletal binding partner of betaI-spectrin. J Cell Sci 113 (Pt 9), 1553-1564.

Gineitis, D, and Treisman, R. (2001) Differential usage of signal transduction pathways defines two types of serum response factor target gene. J. Biol. Chem. 276, 24531-24539

Henderson J. R., Macalma T, Brown, D., Richardson, J. A., Olson, E. N., Beckerle M. C. (1999). The LIM protein, CRP1, is a smooth muscle marker. Dev Dyn. 214, 229-238.

Hirschi, K. K., Lai, L., Belaguli, N. S., Dean, D. A., Schwartz, R. J., Zimmer, W. E. Transforming growth factor-beta induction of smooth muscle cell phenotype requires transcriptional and post-transcriptional control of serum response factor. J. Biol. Chem. 277(8):6287-95.

Jain, M. K., Fujita, K. P., Hsieh, C. M., Endege, W. O., Sibinga, N. E., Yet, S. F., Kashiki, S., Lee, W. S., Perrella, M. A., Haber, E., and Lee, M. E. (1996). Molecular cloning and characterization of SmLIM, a developmentally regulated LIM protein preferentially expressed in aortic smooth muscle cells. J Biol Chem 271, 10194-10199.

Kim, S., Ip, H., Lu, M., Clendenin, C., and Parmacek, M. S. (1997) A serum response factor-dependent transcriptional regulatory program identifies distinct smooth muscle cell sublineages. Mol Cell Biol 17, 2266-2278.

Kocher, A. A., Schuster M. D., Szabolcs M. J., Takuma S., Burkhoff D., Wang J., Homma S., Edwards N. M., Itescu S. (2001). Neovascularization of ischemic myocardium by human bone-marrow-derived angioblasts prevents cardiomyocyte apoptosis, reduces remodeling and improves cardiac function. Nat. Med. 7(4):430-6.

Kong, Y., Flick, M. J., Kudla, A. J., and Konieczny, S. F. (1997). Muscle LIM protein promotes myogenesis by enhancing the activity of MyoD. Mol Cell Biol 17, 4750-4760.

Konrat, R., Krautler, B., Weiskirchen, R., and Bister, K. (1998). Structure of cysteine- and glycine-rich protein CRP2. Backbone dynamics reveal motional freedom and independent spatial orientation of the lim domains. J Biol Chem 273, 23233-23240.

Landerholm, T. E., Dong, X. R., Lu, J., Belaguli, N. S., Schwartz, R. J., and Majesky, M. W. (1999). A role for serum response factor in coronary smooth muscle differentiation from proepicardial cells. Development 126, 2053-2062.

Li, L, Liu, Z., Mercer, B., Overbeek, P., and Olson, E. N. (1997) Evidence for serum response factor-mediated regulatory networks governing SM22α transcription in smooth, skeletal and cardiac muscle cells. Dev Biol 187, 311-321.

Liebhaber, S. A., Emery, J. G., Urbanek, M., Wang, X. K., and Cooke, N. E. (1990). Characterization of a human cDNA encoding a widely expressed and highly conserved cysteine-rich protein with an unusual zinc-finger motif. Nucleic Acids Res 18, 3871-3879.

Louis, H. A., Pino, J. D., Schmeichel, K. L., Pomies, P., and Beckerle, M. C. (1997). Comparison of three members of the cysteine-rich protein family reveals functional conservation and divergent patterns of gene expression. J Biol Chem 272, 27484-27491.

Mack, C. P., and Owens, G. K. (1999) Regulation of smooth muscle alpha-actin expression in vivo is dependent on CArG elements within the 5' and first intron promoter regions. Circ Res 84, 852-861.

Manabe, I., and Owens, G. K. (2001). Recruitment of serum response factor and hyperacetylation of histones at smooth muscle-specific regulatory regions during differentiation of a novel P19-derived in vitro smooth muscle differentiation system. Circ Res 88, 1127-1134.

Mead, P. E., Deconinck, A. E., Huber, T. L., Orkin, S. H., and Zon, L. I. (2001). Primitive erythropoiesis in the *Xenopus* embryo: the synergistic role of LMO-2, SCL and GATA-binding proteins. Development 128, 2301-2308.

Miano, J. M., Carlson, M. J., Spencer, J. A., and Misra, R. P. (2000). Serum response factor-dependent regulation of the smooth muscle calponin gene. J Biol Chem 275, 9814-9822.

Michelsen, J. W., Schmeichel, K. L., Beckerle, M. C., and Winge, D. R. The LIM motif defines a specific zinc-binding protein domain. Proc. Natl. Acad. Sci. 90: 4404-4408.

Milan, M., Diaz-Benjumea, F. J., and Cohen, S. M. (1998). Beadex encodes an LMO protein that regulates Apterous LIM-homeodomain activity in *Drosophila* wing development: a model for LMO oncogene function. Genes Dev 12, 2912-2920.

Morcillo, P., Rosen, C., Baylies, M. K., and Dorsett, D. (1997). Chip, a widely expressed chromosomal protein required for segmentation and activity of a remote wing margin enhancer in *Drosophila*. Genes Dev 11, 2729-2740.

Niklason, L. E., Gao, J., Abbott, W. M., Hirschi, K. K., Houser, S., Marini, R., Langer, R. (1999). Functional arteries grown in vitro. Science 284(5413): 489-493.

Niklason, L. E., Abbott, W., Gao, J., Klagges, B., Hirshi, K. K., Ulubayram, K., Conroy, N., Jones, R., Vasanawala, A., Sanzgiri, S., Langer, R. (2001). Morphologic and mechanical characteristics of engineered bovine arteries. J. Vasc. Surg. 33(3):628-38.

Nishida, W., Nakamura, M., Mori, S., Takahashi, M., Ohkawa, Y., Tadokoro, S., Yoshida, K., Hiwada, K., Hayashi, K., and Sobue, K. (2002). A triad of serum response factor and the GATA and NK families governs the transcription of smooth and cardiac muscle genes. J Biol Chem 277, 7308-7317.

Nix, D. A., and Beckerle, M. C. (1997). Nuclear-cytoplasmic shuttling of the focal contact protein, zyxin: a potential mechanism for communication between sites of cell adhesion and the nucleus. J Cell Biol 138, 1139-1147.

Noveroski J. K., Lai, L., Gaussin, V., Northrop, J. L., Nakamura, H., Hirschi, K. K., Justice, M. J. (2002). Quaking is essential for blood vessel development. Genesis 32(3):218-30.

Nowak, G., Pestic-Dragovich, L., Hozak, P., Philimonenko, A., Simerly, C., Schatten, G., and de Lanerolle, P. (1997). Evidence for the presence of myosin I in the nucleus. J Biol Chem 272, 17176-17181.

Pomies, P., Louis, H. A., and Beckerle, M. C. (1997). CRP1, a LIM domain protein implicated in muscle differentiation, interacts with alpha-actinin. J Cell Biol 139, 157-168.

Rando, O. J., Zhao, K., and Crabtree, G. R. (2000). Searching for a function for nuclear actin. Trends Cell Biol 10, 92-97.

Reecy, J. M., Belaguli, N. S., and Schwartz, R. J. (1999) Serum response factor-Nk homeodomain factor interactions, role in cardiac development. In: (R. Harvey and N. Rosenthal, Ed.) Heart Development, Academic Press, New York, N. Y., pp. 273-290.

Ruzicka, D. L., and Schwartz, R. J. (1988). Sequential activation of alpha-actin genes during avian cardiogenesis: vascular smooth muscle alpha-actin gene transcripts mark the onset of cardiomyocyte differentiation. J Cell Biol 107, 2575-2586.

Schmeichel, K. L., and Beckerle, M. C. (1994). The LIM domain is a modular protein-binding interface. Cell 79, 211-219.

Sepulveda, J. L., Belaguli, N., Nigam, V., Chen, C. Y., Nemer, M., and Schwartz, R. J. (1998). GATA-4 and Nkx-2.5 coactivate Nkx-2 DNA binding targets: role for regulating early cardiac gene expression. Mol Cell Biol 18, 3405-3415.

Sepulveda, J. L., Vlahopoulos, S., Iyer, D., Belaguli, N., and Schwartz, R. J. (2002). Combinatorial expression of GATA4, Nkx2-5 and serum response factor directs early cardiac gene activity. J. Biol. Chem. 277, 25775-25782.

Wada, A., Fukuda, M., Mishima, M., and Nishida, E. (1998). Nuclear export of actin: a novel mechanism regulating the subcellular localization of a major cytoskeletal protein. Embo J 17, 1635-1641.

Wadman, I. A., Osada, H., Grutz, G. G., Agulnick, A. D., Westphal, H., Forster, A., and Rabbitts, T. H. (1997). The LIM-only protein Lmo2 is a bridging molecule assembling an erythroid, DNA-binding complex which includes the TAL1, E47, GATA-1 and Ldb1/NLI proteins. Embo J 16, 3145-3157.

Wang, D., Chang, P. S., Wang, Z., Sutherland, L., Richardson, J. A., Small, E., Krieg, P. A., and Olson, E. N. (2001). Activation of cardiac gene expression by myocardin, a transcriptional cofactor for serum response factor. Cell 105, 851-862.

Wei, L., Roberts, W., Wang, L., Yamada, M., Zhang, S., Zhao, Z., Rivkees, S. A., Schwartz, R. J., and Imanaka-Yoshida, K. (2001). Rho kinases play an obligatory role in vertebrate embryonic organogenesis. Development 128, 2953-2962.

Weiskirchen, R., and Gressner, A. M. (2000). The cysteine- and glycine-rich LIM domain protein CRP2 specifically interacts with a novel human protein (CRP2BP). Biochem Biophys Res Commun 274, 655-663.

Weiskirchen, R., Moser, M., Weiskirchen, S., Erdel, M., Dahmen, S., Buettner, R., and Gressner, A. M. (2001). LIM-domain protein cysteine- and glycine-rich protein 2 (CRP2) is a novel marker of hepatic stellate cells and binding partner of the protein inhibitor of activated STAT1. Biochem J 359, 485-496.

Weiskirchen, R., Pino, J. D., Macalma, T., Bister, K., and Beckerle, M. C. (1995). The cysteine-rich protein family of highly related LIM domain proteins. J Biol Chem 270, 28946-28954.

Yamada, M., Szendro, P. I., Prokscha, A., Schwartz, R. J., and Eichele, G. (1999). Evidence for a role of Smad6 in chick cardiac development. Dev Biol 215, 48-61.

Yamashita, J., Itoh, H., Hirashima, M., Ogawa, M., Nishikawa, S., Yurugi, T., Naito, M., and Nakao, K. (2000). Flk1-positive cells derived from embryonic stem cells serve as vascular progenitors. Nature 408, 92-96.

Zhao, K., Wang, W., Rando, O. J., Xue, Y., Swiderek, K., Kuo, A., and Crabtree, G. R. (1998). Rapid and phosphoinositol-dependent binding of the SWI/SNF-like BAF complex to chromatin after T lymphocyte receptor signaling. Cell 95, 625-636.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

---

What is claimed is:

1. A method of upregulating expression of a SRE containing smooth muscle polynucleotide in a fibroblast, comprising the step of delivering serum response factor (SRF), cysteine-rich LIM-only protein 1 (CRP1) or CRP2, and GATA-4, GATA-5, or GATA-6 to the fibroblast sell, wherein CRP1 or CRP2 comprises at least one operable LIM domain, and wherein said smooth muscle polynucleotide is selected from the group consisting of smooth muscle α-actin, SM22α, smooth muscle myosin heavy chain, calponin, caldesmon, and a combination thereof.

2. The method of claim 1, wherein said CRP1 or CRP2 comprises a nuclear localization signal.

3. The method of claim 1, wherein said CRP1 or CRP2, SRF, and GATA-4, GATA-5, or GATA-6 are delivered substantially concomitantly.

4. The method of claim 1, wherein at least one of CRP1 or CRP2, SRF, and GATA-4, GATA-5, or GATA-6 is delivered as a polynucleotide to the cell.

5. The method of claim 4, wherein the polynucleotide is in a vector.

6. The method of claim 5, wherein the vector is a viral vector.

7. The method of claim 5, wherein the vector is a non-viral vector.

8. The method of claim 6, wherein said viral vector is an adenoviral vector, an adeno-associated vector, or a retroviral vector.

9. The method of claim 1, wherein the cell is in a tissue.

10. A method of generating a smooth muscle cell from a fibroblast cell, comprising the step of delivering SRF, CRP1 or CRP2, and GATA-4, GATA-5, or GATA-6 to the fibroblast cell, wherein the smooth muscle cell is defined as a cell that expresses at least one of the following:
smooth muscle α-actin;
SM 22 α;
smooth muscle myosin heavy chain;
calponin; and
caldesmon.

11. The method of claim 10, wherein said fibroblast is delivered to an individual and is derived from autologous tissue of the individual.

12. The method of claim 10, wherein said fibroblast is delivered to an individual and is derived from allogeneic tissue to the individual.

13. The method of claim 10, wherein said fibroblast is delivered to an individual and is derived from xenogeneic tissue to the individual.

14. A method of generating a smooth muscle cell from an embryonic stem cell, comprising the step of delivering SRF, CRP1 or CRP2, and a GATA-4, GATA-5, or GATA-6 to the embryonic stem cell, wherein the smooth muscle cell is defined as a cell that expresses at least one of the following:
smooth muscle α-actin;
SM 22 α;
smooth muscle myosin heavy chain;
calponin; and
caldesmon.

15. A method of generating a cell from an embryonic stem cell or a fibroblast, wherein the generated cell expresses at least on of smooth muscle a-actin; SM 22 a; smooth muscle myosin heavy chain; calponin; or caldesmon, comprising the step of delivering SRF, CRP1 or CRP2, and GATA-4, GATA-5, or GATA-6 to the embryonic stem cell or the fibroblast cell, respectively.

* * * * *

SEQUENCE LISTING

```
<160> NUMBER OF SEQ ID NOS: 17

<210> SEQ ID NO 1
<211> LENGTH: 16
<212> TYPE: DNA
<213> ORGANISM: Human

<400> SEQUENCE: 1
ccatatatat atatgg                                                      16

<210> SEQ ID NO 2
<211> LENGTH: 508
<212> TYPE: PRT
<213> ORGANISM: Human

<400> SEQUENCE: 2

Met Leu Pro Thr Gln Ala Gly Ala Ala Ala Leu Gly Arg Gly Ser
1               5                   10                  15

Ala Leu Gly Gly Ser Leu Asn Arg Thr Pro Thr Gly Arg Pro Gly Gly
            20                  25                  30

Gly Gly Gly Thr Arg Gly Ala Asn Gly Gly Arg Val Pro Gly Asn Gly
            35                  40                  45

Ala Gly Leu Gly Pro Gly Arg Leu Glu Arg Glu Ala Ala Ala Ala
        50                  55                  60

Ala Thr Thr Pro Ala Pro Thr Ala Gly Ala Leu Tyr Ser Gly Ser Glu
65                  70                  75                  80

Gly Asp Ser Glu Ser Gly Glu Glu Glu Leu Gly Ala Glu Arg Arg
                85                  90                  95

Gly Leu Lys Arg Ser Leu Ser Glu Met Glu Ile Gly Met Val Val Gly
                100                 105                 110

Gly Pro Glu Ala Ser Ala Ala Thr Gly Gly Tyr Gly Pro Val Ser
            115                 120                 125

Gly Ala Val Ser Gly Ala Lys Pro Gly Lys Lys Thr Arg Gly Arg Val
        130                 135                 140

Lys Ile Lys Met Glu Phe Ile Asp Asn Lys Leu Arg Arg Tyr Thr Thr
145                 150                 155                 160

Phe Ser Lys Arg Lys Thr Gly Ile Met Lys Lys Ala Tyr Glu Leu Ser
                165                 170                 175

Thr Leu Thr Gly Thr Gln Val Leu Leu Leu Val Ala Ser Glu Thr Gly
            180                 185                 190

His Val Tyr Thr Phe Ala Thr Arg Lys Leu Gln Pro Met Ile Thr Ser
        195                 200                 205

Glu Thr Gly Lys Ala Leu Ile Gln Thr Cys Leu Asn Ser Pro Asp Ser
    210                 215                 220

Pro Pro Arg Ser Asp Pro Thr Asp Gln Arg Met Ser Ala Thr Gly
225                 230                 235                 240

Phe Glu Glu Thr Asp Leu Thr Tyr Gln Val Ser Glu Ser Asp Ser Ser
                245                 250                 255
```

```
Gly Glu Thr Lys Asp Thr Leu Lys Pro Ala Phe Thr Val Thr Asn Leu
                260                 265                 270

Pro Gly Thr Thr Ser Thr Ile Gln Thr Ala Pro Ser Thr Ser Thr Thr
            275                 280                 285

Met Gln Val Ser Ser Gly Pro Ser Phe Pro Ile Thr Asn Tyr Leu Ala
        290                 295                 300

Pro Val Ser Ala Ser Val Ser Pro Ser Ala Val Ser Ala Asn Gly
305                 310                 315                 320

Thr Val Leu Lys Ser Thr Gly Ser Gly Pro Val Ser Ser Gly Gly Leu
                325                 330                 335

Met Gln Leu Pro Thr Ser Phe Thr Leu Met Pro Gly Gly Ala Val Ala
            340                 345                 350

Gln Gln Val Pro Val Gln Ala Ile Gln Val His Gln Ala Pro Gln Gln
        355                 360                 365

Ala Ser Pro Ser Arg Asp Ser Ser Thr Asp Leu Thr Gln Thr Ser Ser
    370                 375                 380

Ser Gly Thr Val Thr Leu Pro Ala Thr Ile Met Thr Ser Ser Val Pro
385                 390                 395                 400

Thr Thr Val Gly Gly His Met Met Tyr Pro Ser Pro His Ala Val Met
                405                 410                 415

Tyr Ala Pro Thr Ser Gly Leu Gly Asp Gly Ser Leu Thr Val Leu Asn
            420                 425                 430

Ala Phe Ser Gln Ala Pro Ser Thr Met Gln Val Ser His Ser Gln Val
        435                 440                 445

Gln Glu Pro Gly Gly Val Pro Gln Val Phe Leu Thr Ala Ser Ser Gly
    450                 455                 460

Thr Val Gln Ile Pro Val Ser Ala Val Gln Leu His Gln Met Ala Val
465                 470                 475                 480

Ile Gly Gln Gln Ala Gly Ser Ser Ser Asn Leu Thr Glu Leu Gln Val
                485                 490                 495

Val Asn Leu Asp Thr Ala His Ser Thr Lys Ser Glu
            500                 505

<210> SEQ ID NO 3
<211> LENGTH: 193
<212> TYPE: PRT
<213> ORGANISM: human

<400> SEQUENCE: 3

Met Pro Asn Trp Gly Gly Gly Lys Lys Cys Gly Val Cys Gln Lys Thr
1               5                   10                  15

Val Tyr Phe Ala Glu Glu Val Gln Cys Glu Gly Asn Ser Phe His Lys
            20                  25                  30

Ser Cys Phe Leu Cys Met Val Cys Lys Lys Asn Leu Asp Ser Thr Thr
        35                  40                  45

Val Ala Val His Gly Glu Glu Ile Tyr Cys Lys Ser Cys Tyr Gly Lys
    50                  55                  60

Lys Tyr Gly Pro Lys Gly Tyr Gly Tyr Gly Gln Gly Ala Gly Thr Leu
65                  70                  75                  80

Ser Thr Asp Lys Gly Glu Ser Leu Gly Ile Lys His Glu Glu Ala Pro
                85                  90                  95

Gly His Arg Pro Thr Thr Asn Pro Asn Ala Ser Lys Phe Ala Gln Lys
            100                 105                 110

Ile Gly Gly Ser Glu Arg Cys Pro Arg Cys Ser Gln Ala Val Tyr Ala
        115                 120                 125
```

Ala Glu Lys Val Ile Gly Ala Gly Lys Ser Trp His Lys Ala Cys Phe
    130                 135                 140

Arg Cys Ala Lys Cys Gly Lys Gly Leu Glu Ser Thr Thr Leu Ala Asp
145                 150                 155                 160

Lys Asp Gly Glu Ile Tyr Cys Lys Gly Cys Tyr Ala Lys Asn Phe Gly
                165                 170                 175

Pro Lys Gly Phe Gly Phe Gly Gln Gly Ala Gly Ala Leu Val His Ser
            180                 185                 190

Glu

<210> SEQ ID NO 4
<211> LENGTH: 193
<212> TYPE: PRT
<213> ORGANISM: Rat

<400> SEQUENCE: 4

Met Pro Asn Trp Gly Gly Lys Lys Cys Gly Val Cys Gln Lys Thr
1               5                   10                  15

Val Tyr Phe Ala Glu Glu Val Gln Cys Glu Gly Asn Ser Phe His Lys
            20                  25                  30

Ser Cys Phe Leu Cys Met Val Cys Lys Lys Asn Leu Asp Ser Thr Thr
        35                  40                  45

Val Ala Val His Gly Glu Glu Ile Tyr Cys Lys Ser Cys Tyr Gly Lys
    50                  55                  60

Lys Tyr Gly Pro Lys Gly Tyr Gly Tyr Gly Gln Gly Ala Gly Thr Leu
65                  70                  75                  80

Ser Met Asp Lys Gly Glu Ser Leu Gly Ile Lys His Glu Glu Ala Pro
                85                  90                  95

Gly His Arg Pro Thr Thr Asn Pro Asn Ala Ser Lys Phe Ala Gln Lys
            100                 105                 110

Ile Gly Gly Ser Glu Arg Cys Pro Arg Cys Ser Gln Ala Val Tyr Ala
        115                 120                 125

Ala Glu Lys Val Ile Gly Ala Gly Lys Ser Trp His Lys Ser Cys Phe
    130                 135                 140

Arg Cys Ala Lys Cys Gly Lys Gly Leu Glu Ser Thr Thr Leu Ala Asp
145                 150                 155                 160

Lys Asp Gly Glu Ile Tyr Cys Lys Gly Cys Tyr Ala Lys Asn Phe Gly
                165                 170                 175

Pro Lys Gly Phe Gly Phe Gly Gln Gly Ala Gly Ala Leu Val His Ser
            180                 185                 190

Glu

<210> SEQ ID NO 5
<211> LENGTH: 1817
<212> TYPE: DNA
<213> ORGANISM: Human

<400> SEQUENCE: 5
gccgccactt ccgagagcgc ctgccgcccc tgcgccgccg agccagctgc cagaatgccg     60
aactggggag gaggcaagaa atgtggggtg tgtcagaaga cggtttactt tgccgaagag    120
gttcagtgcg aaggcaacag cttccataaa tcctgcttcc tgtgcatggt ctgcaagaag    180
aatctggaca gtaccactgt ggccgtgcat ggtgaggaga tttactgcaa gtcctgctac    240
ggcaagaagt atgggcccaa aggctatggc tacgggcagg gcgcaggcac cctcagcact    300

```
gacaaggggg agtcgctggg tatcaagcac gaggaagccc ctggccacag gcccaccacc      360
aaccccaatg catccaaatt tgcccagaag attggtggct ccgagcgctg ccccccgatgc    420 agccaggcag tctatgctgc ggagaaggtg attggtgctg ggaagtcctg cataaggcc      480 tgctttcgat gtgccaagtg tggcaaaggc cttgagtcaa ccaccctggc agacaaggat     540
ggcgagattt actgcaaagg atgttatgct aaaaacttcg ggcccaaggg ctttggtttt     600
gggcaaggag ctggggcctt ggtccactct gagtgaggcc accatcaccc accacaccct     660
gcccactcct gcgcttttca tcgccattcc attcccagca gctttggaga cctccaggat     720
tatttctctg tcagccctgc cacatatcac taatgacttg aacttgggca tctggctccc     780
tttggtttgg gggtctgcct gaggtcccac cccactaaag gctccccag gcctgggatc      840 tgacaccatc accagtagga gacctcagtg ttttgggtct aggtgagagc aggcccctct     900
ccccacacct cgccccacag agctctgttc ttagcctcct gtgctgcgtg tccatcatca     960
gctgaccaag acacctgagg acacatcttg gcacccagag gagcagcagc aacaggctgg    1020
agggagaggg aagcaagacc aagatgagga gggggaagg ctgggtttttt tggatctcag    1080 agattctcct ctgtgggaaa gaggttgagc ttcctggtgt ccctcagagt aagcctgagg    1140
agtcccagct tagggagtca ctattggagg cagagaggca tgcaggcggg gtcctaggag    1200
cccctgcttc tccaggcctc ttgcctttga gtctttgtgg aatggatagc ctcccactag    1260
gactgggagg agaataaccc aggtcttaag gaccccaaag tcaggatgtt gtttgatctt    1320
ctcaaacatc tagttcccctg cttgatggga ggatcctaat gaaatacctg aaacatatat    1380
tggcatttat caatggctca aatcttcatt tatctctggc cttaaccctg gctcctgagg    1440
ctgcggccag cagagcccag gccagggctc tgttcttgcc acacctgctt gatcctcaga    1500
tgtggaggga ggtaggcact gcctcagtct tcatccaaac cctttccct ttgccctgag     1560 acctcagaat cttcccttta acccaagacc ctgcctcttc cactccaccc ttctccaggg    1620
acccttagat cacatcactc cacccctgcc aggccccagg ttaggaatag tggtgggagg    1680
aaggggaaag ggctgggcct caccgctccc agcaactgaa aggacaacac tatctggagc    1740
cacccactga aagggctgca ggcatgggct gtacccaagc tgatttctca tctggtcaat    1800
aaagctgttt agaccag                                                    1817
```

<210> SEQ ID NO 6
<211> LENGTH: 1178
<212> TYPE: DNA
<213> ORGANISM: Human

<400> SEQUENCE: 6

```
gaggaggcct agaatatgaa ccagatagag attgcattgt ttattttcct tttcatctaa     60
aacaataaat catcctgtag cttaggcatt aggtcccttc ggatgtcacg gtatccttgt    120
gcttttctga catcaacaca tataaataca gggcctgtgg cgcccggggt ttctgcctgg    180
gtttaggttt cttccccctc agcatcgcgt gctgtgccct ggtggagggg aagagcgaaa    240
cactttggga atgggcgtt ttcgtaacgt catttattta gtctagatga attttgctct     300
ttaagaataa gaagttgtgg attcccagaa gctggaaatc ggacgagaga atatgcgtta    360
actagggaag ttaatcacgt tgagtttact gacaaggaca aggcaagggg gaggtggcgg    420 aaagcccccgt ttggctgact ttctactgct ggagcctccc ggcccgtgac tgtctccgcg    480
aagaggggga tcgcgctcg cggtggacag gtccgacgca gggcggcggg ggccactttc     540
cagcgggacc gtcccgccgc cgggcctccc tggagggaa ggaagtccct ctccaagtcc     600
```

-continued

```
cagtggcttt tggaactgcc gggtcccttt gggagggagc ggtcccggga cgtgggaaga    660
tgccgggcgg gcgggaagct gcaggaagag gcgggcctcc tgccttttgt ctcctggtgg    720
ctagcccgga gcgggcagag ggcagcccgc ccgctacacg ccccagcccg gcaagcggct    780
ccgggaatcc ggcgggcggg gctgggagga gggcggggcg gacacaggcc gcccaccgag    840
cgctctttaa aaggcaccgg cgcgcgttcg cctgggatct cggactccct ggaccctccc    900
tccagcccag cctcgctagc tccgcctgcg gtacgtgctc ccgcctccga ctcaagtgag    960
taggggcggt ggggcggttc gcggcgcgcc ccaaccccgg ggcgggagtt gcagggggtt   1020
tccaccgcct cccggggtcg tgctgtcgcc cggccggcgc gccccggtct cctccgacat   1080
ccccatcccg gtccgcattt gtgccctgc cagccttctc atccctgcgc cccagatttt    1140
ctctctctta tcccccaaac acacctgccc ttgtcccc                           1178
```

<210> SEQ ID NO 7
<211> LENGTH: 193
<212> TYPE: PRT
<213> ORGANISM: Human

<400> SEQUENCE: 7

```
Met Pro Val Trp Gly Gly Gly Asn Lys Cys Gly Ala Cys Gly Arg Thr
1               5                   10                  15

Val Tyr His Ala Glu Glu Val Gln Cys Asp Gly Arg Ser Phe His Arg
            20                  25                  30

Cys Cys Phe Leu Cys Met Val Cys Arg Lys Asn Leu Asp Ser Thr Thr
        35                  40                  45

Val Ala Ile His Asp Glu Glu Ile Tyr Cys Lys Ser Cys Tyr Gly Lys
    50                  55                  60

Lys Tyr Gly Pro Lys Gly Tyr Gly Tyr Gly Gln Gly Ala Gly Thr Leu
65                  70                  75                  80

Asn Met Asp Arg Gly Glu Arg Leu Gly Ile Lys Pro Glu Ser Val Gln
                85                  90                  95

Pro His Arg Pro Thr Thr Asn Pro Asn Thr Ser Lys Phe Ala Gln Lys
            100                 105                 110

Tyr Gly Gly Ala Glu Lys Cys Ser Arg Cys Gly Asp Ser Val Tyr Ala
        115                 120                 125

Ala Glu Lys Ile Ile Gly Ala Gly Lys Pro Trp His Lys Asn Cys Phe
    130                 135                 140

Arg Cys Ala Lys Cys Gly Lys Ser Leu Glu Ser Thr Thr Leu Thr Glu
145                 150                 155                 160

Lys Glu Gly Glu Ile Tyr Cys Lys Gly Cys Tyr Ala Lys Asn Phe Gly
                165                 170                 175

Pro Lys Gly Phe Gly Tyr Gly Gln Gly Ala Gly Ala Leu Val His Ala
            180                 185                 190

Gln
```

<210> SEQ ID NO 8
<211> LENGTH: 901
<212> TYPE: DNA
<213> ORGANISM: Human

<400> SEQUENCE: 8

```
gggatctcgg actccctgga ccctccctcc agcccagcct cgctagctcc gcctgcggta     60
cgtgctcccg cctccgactc aaaatgcctg tctggggagg tggaaacaag tgtggggcct    120
```

```
gtgggaggac cgtgtaccac gcagaagagg tgcagtgtga tggcaggagc ttccaccgct    180
gctgctttct ctgcatggtt tgcaggaaaa atttagatag cacaacagtg caattcacg     240 atgaagagat ctactgcaaa tcctgctacg gaaagaagta tgggccaaaa ggctacggtt    300
atggccaggg cgctggcacg cttaacatgg accgtggcga gaggctgggc atcaaaccag    360
agagtgttca gcctcacagg cctacaacaa atccaaacac ttctaaattt gctcagaaat    420
atggaggtgc tgagaagtgt tccagatgtg gggattctgt atatgctgcc agaagataa    480 ttggagctgg aaagccctgg cacaaaaact gtttccgatg tgcaaagtgt gggaagagtc    540
ttgaatcaac aactctgact gaaaaagaag gtgaaatcta ttgtaaagga tgctatgcaa    600
agaactttgg gcccaaggga tttggctatg gccaggagc aggggctctt gttcatgccc     660
agtaagatgt aaaccctgaa ctaaacatca cacactgaga tctcttcat aatctaggca     720 cagataatct ttaacactaa actactgtga aattctacca gcattaagta ctgtatatcg    780
ccctgtactt ggataggctg gctaactcgt aggaagagag cactgtatgg tatccttttg    840
ctttattcac cagcattttg ggggaacatt tcttttacat tttaaataaa acttcagctt    900
g                                                                    901
```

<210> SEQ ID NO 9
<211> LENGTH: 193
<212> TYPE: PRT
<213> ORGANISM: Human

<400> SEQUENCE: 9

```
Met Pro Val Trp Gly Gly Gly Asn Lys Cys Gly Ala Cys Gly Arg Thr
1               5                   10                  15

Val Tyr His Ala Glu Glu Val Gln Cys Asp Gly Arg Ser Phe His Arg
            20                  25                  30

Cys Cys Phe Leu Cys Met Val Cys Arg Lys Asn Leu Asp Ser Thr Thr
        35                  40                  45

Val Ala Ile His Asp Glu Glu Ile Tyr Cys Lys Ser Cys Tyr Gly Lys
    50                  55                  60

Lys Tyr Gly Pro Lys Gly Tyr Gly Tyr Gly Gln Gly Ala Gly Thr Leu
65                  70                  75                  80

Asn Met Asp Arg Gly Glu Arg Leu Gly Ile Lys Pro Glu Ser Val Gln
                85                  90                  95

Pro His Arg Pro Thr Thr Asn Pro Asn Thr Ser Lys Phe Ala Gln Lys
            100                 105                 110

Tyr Gly Gly Ala Glu Lys Cys Ser Arg Cys Gly Asp Ser Val Tyr Ala
        115                 120                 125

Ala Glu Lys Ile Ile Gly Ala Gly Lys Pro Trp His Lys Asn Cys Phe
    130                 135                 140

Arg Cys Ala Lys Cys Gly Lys Ser Leu Glu Ser Thr Thr Leu Thr Glu
145                 150                 155                 160

Lys Glu Gly Glu Ile Tyr Cys Lys Gly Cys Tyr Ala Lys Asn Phe Gly
                165                 170                 175

Pro Lys Gly Phe Gly Tyr Gly Gln Gly Ala Gly Ala Leu Val His Ala
            180                 185                 190

Gln
```

<210> SEQ ID NO 10
<211> LENGTH: 7942
<212> TYPE: DNA
<213> ORGANISM: Human

<400> SEQUENCE: 10

```
agatcttcag ctgagttcaa aaaaatatgt ttattaaaaa tgggcatatt agggaggggg      60
acaaggcttg cctttcccct ccccacgctt ctttcttaac tcctgtggat tctaatggca     120
tagcttgttt tgtgcctggt gacctgtact attgtactga atgcaggtcc tttgtctggc     180
aggaaaaaaa aaaatcttg tgcacgacaa gccagtttcc taatgaaaga gttgttattt      240
gggagaggag atgaggttat tttggaggaa cgcaggcctt tgaaagatgt ggttagagag     300
gttcataaag aaacgaaaat ctgcagtccc tgggcttaaa tagccctcta gggagccgta     360
cgaccagcac agggacattc taatgaatcc tttattcctt cagaatgcct gtctggggag     420
gtggaaacaa gtgtgggcc tgtgggagga ccgtgtacca cgcagaagag gtgcagtgtg      480
atggcaggag cttccaccgc tgctgctttc tctgcagtaa gtagctctcc atgctccacc     540
tttgacggaa tttgtatgta cagagcttca atatgtctat ttaaggaaaa attgtggttt     600
tgccaacaaa gatcattttg aaagcacgaa tggttttttac ctgtcttctt agatgttgta    660
aatgccaagc ctagcagcga agacaggagg ggtggcccaa gacacccagc ctcccttgt      720
gtccccatag cttttggcct ccatttttggc ctttatttttg ttaacacatc tgcctcccc   780
acctcactga gtgctgggtg tcacttatgt ggtctggcac ctagcacagt ttctggcaca    840
ttacaagggc ttagctccca tttttgagta aatgattgct cctcatccac cccagctttc   900
tctttctcag gttccctta atgacaacaa agtcttcggt tttaaaactg tagagtagca     960
acttaaagca cttcattaat catcttctga tttaatgaca gaattttctt taatgaatga    1020
ttatgtcagg taaacccacc catacgggca gatgtttgcc ttatcaatag tattgtacag   1080
ggaaaattcc tacagaaaac cataggttaa aaataggtta cattgagaaa taatcttcag   1140
gaaaagactt ctttctcaaa tttgaattgt ccttttccct cattggagcc agcattcaag   1200
gtatctggac ctctttaata gcataactaa actgctttgc agacaaccag aagcagacaa   1260
cagaaagttg cagttacaaa aaaataaaaa tactacatag gaatgttcac tatgtatgcc   1320
ttcctcagaa gacttggttt aaccattgct tttagaagtt acttttttaa aaaggaatc     1380
tattttttcag caggcttgta accaagaaag tatggaaaca gaatgcaaat actttagaaa    1440
ttgctctcag tttcatctgt ctaggttaag ccacaatgtc tacaccatag taacatatgc    1500
gtgtatgctg ttgacatttg ttttactaaa tgtcaagttc tctactggtc atttctacga   1560
atcctttcta atatctgtct ctgctgacta atgccttta aggaaataat tcagagtagt   1620
ttgcagacct atgagaattt tactgcagag aacagcatga ggactgggga agaaaggggt   1680
ggttatatag taacactttc atatacctac acttgttttg gttcatacag gtttttcaaa   1740
acagtattta catttattct ctctgttaag ggtagttgtc cttcagcagt gcatggtgtt   1800
aggttaacta tggtttaaga tatagttatc tttaggcaca tgtatttcag cacttgagcc   1860
tcaacagtta gattccagag tagatgccat tcattctac catagaagac tttagtttaa    1920
gataatagac taaatttaaa ccagccagct agtcctgctt ccctcccctc ctctttgctg   1980
tccttccttt ttattcaacc ccccccttt tatttttctt acttttaatt tttatgggta   2040
catagtaggt atatatattt atggggtaca tgagatgttt tgctacaggc atacaatgta   2100
tgttaatcac atcatcttaa atgggtatc cattacctca agcatttatt attttttttgt  2160
taccaacatt ccagttaata ctgtcttatt tttaaatgta caatgattgt tgacagtaat   2220
catcctgttg tgctatcaaa tactagatct tattcattct aactatattt ttacacccat   2280
```

```
taactctcct cacttccttc ccgacaccct acccttccga gcttctggta accatcattc    2340
tactctgaat catcatacaa ttgtctttta aataagggga agaaattctg atctttgatt    2400
tccagctgcc agattgtgct accagtgagt ttcctcacaa tttacttttt tctcaagctt    2460
aattgaagtt ttagaaaatg aaataatgtc tggatgaaac tcgatgacat ttggcagttt    2520
tatgaagtgg gacacgtgga aatgtcctgt ggcaagagat ccatcaagaa agaatgcatt    2580
ctcctttggg acagaaggga aaacaaatgc agactttaaa gcacttgacg attttcaggc    2640
agactcatca ctgctggaga agctgctggg gagaggaaag tgtgatactt cccagtctag    2700
actagtgatg aaaactagaa ttcaggattt aaaactatta ttatcccagg aggtgctttt    2760
gggggaggaa aggctacaga ggcaagtccc cgaagcactg agcttcccct ctgttctgta    2820
ttaggttgtg atttaacagt acttggttaa gagaaggcta aaaagattaa gagtgttgag    2880
ggttgggagc aaggtggtgt tttattcctt ttgtttaagc attttatag ccacctttga     2940 aacttttctc ccttaatatg atctcccaga aagggaaatc atagtaagag tttgatcagc    3000
accacaggaa agggaataaa aaataaacga aacaaactaa aaataaagct tgaggcttct    3060
ggatgttata ttctgataca tttctgaagc aactgtcata tccatggagg aatgtaaata    3120
atcctcgaat gtagctggcc agtccagatg ctgtctcatg gcttttggga agccacagga    3180
taaaccagga atgtgaggga gcctcagcct tcaccatttg taggccatgt gtctgtgcca    3240
ccattgttct aaggaaaaag gcatctttgg aacatgtgta aagtctaact tttcccctg     3300 cagtggtttg caggaaaaat ttagatagca caacagtggc aattcacgat gaagagatct    3360
actgcaaatc ctgctacgga aagaagtatg ggccaaaagg ctacggttat ggccagggcg    3420
ctggcacgct taacatggac cgtggcgaga ggctgggcat caaaccagag aggtgagttg    3480
ggagaccgtt ggttaccttc agaaatgagt tgcgacagtt agtgccgctt gctgaacagg    3540
aacctggcag tctccagatt tttagttgaa actaagcaaa taaatggga ctctgatttt     3600 ctaatgtcaa ctagttcaaa atattgagtt ttggacctaa caaagttctt attaataatt    3660
ccagtgattt ctacttctgg ctttatagca ttccaagctg tatcaaggag tcgtgttctc    3720
aaaagcaagt gatttgtatt tacttcaatt tcacagcacc ttggagaccg gatgtcatga    3780
aattaaatgg tagagaaatg tgctgtgtga atcatgagag gtgtttctca tgtgcaatgt    3840
aagcagccaa tgaaaattcc taagtcactc cttctatgta aacattttc atcaagaaat     3900 cacttttctc taacttaaaa ttttttactt aaaaatggaa attacttctt atttttgatt    3960 cttttgagaga gtagtgttaa actttaaagg ctttgttgcc aacgtatcaa ggtgctaaat   4020
ttgtgaaagt tcacttagta tttcatattc aggttaaata acttatttgt ttagaattcc    4080
ccccacacac tttttttttt ctttttttgtc acagaatctc actctgtcac ccaagctgga   4140
gtgcactggc acaatctcgg ctcactgcaa cctctgcctc ccaggttcaa gtgattctct    4200
tgtctcagcc tcctgagtag ctgggattac aggcgtgcac caccacccg gctaatttt      4260 tgtattttg gtagaggcgg ggtctcacca tattggccag gctggtcctg aactcctggc     4320
ctcaagtgat ctacttatct cggcctccca agtgcatgg aataacaggc atgagccacc     4380
gtgcccaacc tggaatttcc tcctaactcc tacttttaac ccagtgattc cactatttga    4440
acttcacatt ttcacatcca ttttatattg agaagtccaa aattggtgta atagtccaac    4500
aaaatggcct ttgacaagaa ccataaacca tgccagccac cgtgcagcat tagcatatgt    4560
taactcgtgt aatcctcaca acagtcctac aacataggc ttcctctctt tcttcagaac     4620
agatgaagac aagaaaaatt aagtaaaaac tttgcccaaa gtcacactgt tagttaattg    4680
```

```
tagagcctgg aacttaacct agtctaactc caaaccttat gacctgaatg aaacgtggtg    4740
cttggcttgg ctaaaataat aattaccatg tattgagtcc ctgttgtctg ttgaacattt    4800
atcttcattc tgtataatcc ttagagtaac tctgaggtat actttgtcca tttatagatg    4860
acgacactaa gagtcgggtc acacaaataa gtgagggagc caggatttga atcaatgtcc    4920
atttggttcc aaaatctgtt ctcttcctac tgcagtatgt actacattga ggctcacctc    4980
tgtgttcttt gagcttcttc caccctcaga gtttctgggc catgatgccc agcttacctt    5040
tttatctttt ttaaaattta ttttacttgt tctgctctcc ttttccatct tgttacatct    5100
atttttgtgt tttaaaggtt ttgttgaaaa cctttcaaaa tccatatccc ctcactcaac    5160
ctgcatctcc ctcaatccaa accagattta tccatgaccc caaaagtaag tcagtgacta    5220
tggccatagt tttaaagcac aaagaccagt gaaccctcct tttttaaaa aaaaaaaaa     5280 atatatatat atatatatag acagggtctt gctatgttgc ctaggctggc ctcgaactcc    5340
tgagttcaag ttatccttcc acattggcct cccaaagtgc taggaagaca ttgttttcc    5400 agtaggaaaa attaacagtt gtggagtgct atcattttat ctgctcagct aatttataag    5460
gttctaagag ggcttaaaaa aaaaaagtc ttctcaaagc ccgagaatgt tctgcacata    5520
ctaggtacac cttactgaat ggaaacagtt cctactgata gcaagaaata tggtttactc    5580
agtgatctgt aaatagtgac aaaaatacca cccttaccag agaaaatga aagataaaca    5640 gattgcatag taataatcaa aatttataaa atatttttcc atgaagaaag ttggctattc    5700
acactttcct ttattcaaga tatactggga gactaagtaa tctataaaac atgcttaaat    5760
ttcttagtta cagaccaaag ttaacttacc tatttgtgga attttaaac tacttaatag     5820 tggttttttcc gactcctgtg aagtaaaaag ctaggtatga ttccagtgat attattctgg    5880
agtaaaaata tatgctctgg taagttttta taaaccgtaa cataattgct tagtggagag    5940
gccaacactg aggagtaaat gaattctgtt tagactcaga gggacagatc tttacgtttg    6000
ggtccctatc tggtttttttg aaataataat gagcccatag ataggttcaa gtagtaactc    6060
tggctggcac ctgagtcact tcttctttat tccctcccct gtgctggcct gcaaaggctt    6120
ccagctttga ggcagtgtag cggttaagtc ccagagttct attgttcctg ccttgtgtac    6180 ttaaagggc cctgtggaaa ctcttgccta cttttttttt cctcttttca caagtgttca     6240
gcctcacagg cctacaacaa atccaaacac ttctaaattt gctcagaaat atggaggtgc    6300
tgagaagtgt tccagatgtg gggattctgt atatgctgcc gagaagataa ttggagctgg    6360
aaaggtaaag tgctatttgg aattaataac agcaaatgac ttctctctgc tcccttctc     6420 ccctaaccct tccacattcc ttgcttgggt gatgtcttac aaatcactgt cttatatgaa    6480
acttttcttt aaatgcattt ccatcagaat cattaacttt tttgaagtga ttcccttatt    6540
tgacaagtca tttttctgtt taaaagaact tgttttcata gggggcactc ctgaaggtta    6600
aactttaaaa ggccagactg taagggaatc tccaggttat tcagtatagt gaaaaagca     6660 ggaatccgag tcaggacacc tgatgcgaat tcagtgtgtg gatttggaaa agttaccagc    6720
taacctcttt gagctgcgct gttcttggcc agaaaaaaga tggtctcttt aaaggagcag    6780
actgggcttg tggttaggac tgaggctgct cttaggaaa cagcctttct gtgggtgatc     6840
aagagtgcag atactgagga ctggtttcag ccttctcatt ggagctgaac cacagaagtc    6900
aggagcttgc tttgagatga tcatcctgag ccacttcttg ccatacatct aaattgaact    6960
gtaggaaaca ggcctctcaa acatgctgac acattcatct cttccagccc tggcacaaaa    7020
```

| | |
|---|---|
| actgtttccg atgtgcaaag tgtgggaaga gtcttgaatc aacaactctg actgaaaaag | 7080 |
| aaggtgaaat ctattgtaaa ggtaaaattc atttcagtta ctgctgtcca tatgaatatc | 7140 |
| cacactggtt cttgtttaat gaaatgtcac tggcattaaa aaaaaaaaaa gaaaagtatg | 7200 |
| ccactatttt ctgaaaataa aatatcccaa gatgcttata gatgacagag aaccacagtt | 7260 |
| aagttcctga tcatttaaaa ctcccccacca gataaaaaca ccacaaatag ccatcttttg | 7320 |
| ccttcatgtc ttgagcaaag cgtaagtata tggaagaaaa cagacaaata catccttac | 7380 |
| ctggcctgac tcatgcttgc aactcagcag gaccacgctg aacactatag ggccagaatg | 7440 |
| tgtggacttg tctttgcagc tttaagatat ttagtacatg acacatttaa catcttaaat | 7500 |
| aagttgagct cttttacaca gcagtttaat ttatgggggt tgttgagtg ggtcttaagc | 7560 |
| agtgctagca aagcttaatg gacttgcact aactatcctt cctccctttc ctttgtagga | 7620 |
| tgctatgcaa agaactttgg gcccaaggga tttggctatg ccaaggagc aggggctctt | 7680 |
| gttcatgccc agtaagatgt aaaccctgaa ctaaacatca cactgaga atctcttcat | 7740 |
| aatctaggca cagataatct ttaacactaa actactgtga aattctacca gcattaagta | 7800 |
| ctgtatatcg ccctgtactt ggataggctg gctaactcgt aggaagagag cactgtatgg | 7860 |
| tatcctttg ctttattcac cagcattttg ggggaacatt tcttttacat tttaaataaa | 7920 |
| acttcagctt gatttgggtg tt | 7942 |

<210> SEQ ID NO 11
<211> LENGTH: 1178
<212> TYPE: DNA
<213> ORGANISM: Human

<400> SEQUENCE: 11

| | |
|---|---|
| gaggaggcct agaatatgaa ccagatagag attgcattgt ttattttcct tttcatctaa | 60 |
| aacaataaat catcctgtag cttaggcatt aggtccttc ggatgtcacg gtatccttgt | 120 |
| gcttttctga catcaacaca tataaataca gggcctgtgg cgcccggggt ttctgcctgg | 180 |
| gtttaggttt cttcccctc agcatcgcgt gctgtgccct ggtggagggg aagagcgaaa | 240 |
| cactttggga atggggcgtt ttcgtaacgt catttattta gtctagatga attttgctct | 300 |
| ttaagaataa gaagttgtgg attcccagaa gctggaaatc ggacgagaga atatgcgtta | 360 |
| actagggaag ttaatcacgt tgagtttact gacaaggaca aggcaagggg gaggtggcgg | 420 |
| aaagccccgt ttggctgact ttctactgct ggagcctccc ggcccgtgac tgtctccgcg | 480 |
| aagaggggga tcggcgctcg cggtggacag gtccgacgca gggcggcggg ggccactttc | 540 |
| cagcgggacc gtcccgccgc cgggcctccc tggaggggaa ggaagtccct ctccaagtcc | 600 |
| cagtggcttt tggaactgcc gggtcccttt ggagggagc ggtcccggga cgtgggaaga | 660 |
| tgccgggcgg gcgggaagct gcaggaagag gcgggcctcc tgccttttgt ctcctggtgg | 720 |
| ctagcccgga gcgggcagag ggcagcccgc cgctcacacg cccagcccg caagcggct | 780 |
| ccgggaatcc ggcgggcggg gctgggagga gggcggggcg gacacaggcc gcccaccgag | 840 |
| cgctctttaa aaggcaccgg cgcgcgttcg cctgggatct cggactccct ggaccctccc | 900 |
| tccagcccag cctcgctagc tccgcctgcg gtacgtgctc ccgcctccga ctcaagtgag | 960 |
| tagggcggt gggcggttc gcggcgccg ccaaccccgg ggcggagtt gcaggggtt | 1020 |
| tccaccgcct cccggggtcg tgctgtcgcc cggccggcgc gcccgggtct cctccgacat | 1080 |
| ccccatcccg gtccgcattt gtgccctgc cagccttctc atccctgcgc ccagatttt | 1140 |
| ctctctctta tccccaaac acacctgccc ttgtcccc | 1178 |

<210> SEQ ID NO 12
<211> LENGTH: 480
<212> TYPE: PRT
<213> ORGANISM: Human

<400> SEQUENCE: 12

```
Met Glu Val Ala Pro Glu Gln Pro Gly Trp Met Ala His Pro Ala Val
1               5                   10                  15

Leu Asn Ala His Asp Pro Asp Ser His His Pro Gly Leu Ala His Asn
            20                  25                  30

Tyr Met Glu Pro Ala His Val Leu Pro Pro Asp Glu Val Asp Val Phe
        35                  40                  45

Phe Asn His Leu Asp Ser Gln Gly Asn Pro Tyr Tyr Ala Asn Pro Ala
    50                  55                  60

His Ala Arg Ala Ala Val Ser Tyr Ser Pro Ala His Ala Arg Leu Thr
65                  70                  75                  80

Gly Ser Gln Met Cys Arg Pro His Leu Leu His Ser Pro Gly Leu Pro
                85                  90                  95

Trp Leu Asp Gly Gly Lys Ala Ala Leu Ser Ala Ala Ala His His
            100                 105                 110

His Asn Pro Trp Thr Val Ser Pro Phe Ser Lys Thr Pro Leu His Pro
        115                 120                 125

Ser Ala Ala Gly Gly Pro Gly Gly Pro Leu Ser Val Tyr Pro Gly Ala
    130                 135                 140

Gly Gly Gly Ser Gly Gly Ser Gly Ser Ser Val Ala Ser Leu Thr
145                 150                 155                 160

Pro Thr Ala Ala His Ser Gly Ser His Leu Phe Gly Phe Pro Pro Thr
                165                 170                 175

Pro Pro Lys Glu Val Ser Pro Asp Pro Ser Thr Thr Gly Ala Ala Ser
            180                 185                 190

Pro Ala Ser Ser Ser Ala Gly Gly Ser Ala Ala Arg Gly Glu Asp Lys
        195                 200                 205

Asp Gly Val Lys Tyr Gln Val Ser Leu Thr Glu Ser Met Lys Met Glu
    210                 215                 220

Ser Gly Ser Pro Leu Arg Pro Gly Leu Ala Thr Met Gly Thr Gln Pro
225                 230                 235                 240

Ala Thr His His Pro Ile Pro Thr Tyr Pro Ser Tyr Val Pro Ala Ala
                245                 250                 255

Ala His Asp Tyr Ser Ser Gly Leu Phe His Pro Gly Gly Phe Leu Gly
            260                 265                 270

Gly Pro Ala Ser Ser Phe Thr Pro Lys Gln Arg Ser Lys Ala Arg Ser
        275                 280                 285

Cys Ser Glu Gly Arg Glu Cys Val Asn Cys Gly Ala Thr Ala Thr Pro
    290                 295                 300

Leu Trp Arg Arg Asp Gly Thr Gly His Tyr Leu Cys Asn Ala Cys Gly
305                 310                 315                 320

Leu Tyr His Lys Met Asn Gly Gln Asn Arg Pro Leu Ile Lys Pro Lys
                325                 330                 335

Arg Arg Leu Ser Ala Ala Arg Arg Ala Gly Thr Cys Cys Ala Asn Cys
            340                 345                 350

Gln Thr Thr Thr Thr Thr Leu Trp Arg Arg Asn Ala Asn Gly Asp Pro
        355                 360                 365

Val Cys Asn Ala Cys Gly Leu Tyr Tyr Lys Leu His Asn Val Asn Arg
```

```
                     370                375                380
Pro Leu Thr Met Lys Lys Glu Gly Ile Gln Thr Arg Asn Arg Lys Met
385                 390                395                400

Ser Asn Lys Ser Lys Lys Ser Lys Lys Gly Ala Glu Cys Phe Glu Glu
                405                410                415

Leu Ser Lys Cys Met Gln Glu Lys Ser Ser Pro Phe Ser Ala Ala Ala
            420                425                430

Leu Ala Gly His Met Ala Pro Val Gly His Leu Pro Pro Phe Ser His
        435                440                445

Ser Gly His Ile Leu Pro Thr Pro Thr Pro Ile His Pro Ser Ser Ser
    450                455                460

Leu Ser Phe Gly His Pro His Pro Ser Ser Met Val Thr Ala Met Gly
465                470                475                480

<210> SEQ ID NO 13
<211> LENGTH: 2729
<212> TYPE: DNA
<213> ORGANISM: Human

<400> SEQUENCE: 13
tcgagatcca ttgtgctcta aagggagtcg gcagctggcg ccagggcggc cggaggatgc      60
cgaggggccg gagccgggcg ggcccgagcg cgaggcgcac tctaccccca gctcctaccc     120
tgtaagcccc gccagcctcc ggacgtgctg tccctgggcc cgtcgccctc ggggctcccg     180
ccggaactcc ttcactctca gaggccgagt ccctcccctc cccacggctg cgtgtggccg     240
ttgccgtctg cacccagacc ctgagccgcc gcgccggcc atggaggtgg cgccggagca     300
gcccggctgg atggcgcacc cggccgtgct gaatgcgcac gaccccgact cacaccaccc     360
gggcctggcg cacaactaca tggaacccgc gcacgtgctg cctccagacg aggtggacgt     420
cttcttcaat cacctcgact cgcagggcaa ccctactat gccaaccccg ctcacgcgcg     480
ggcggccgtc tcctacagcc ccgcgcacgc ccgcctgacc gggagccaga tgtgccgccc     540
acacttgttg cacagcccgg gtttgccctg gctggacggg ggcaaagcag ccctctctgc     600
cgctgcggcc caccaccaca cccctggac cgtgagcccc ttctccaaga cgccactgca     660 ccctcagct gctggaggcc ctggaggccc actctctgtg tacccagggg ctggggtgg     720 gagcgggga ggcagcggga gctcagtggc ctccctcacc cctacagcag cccactctgg     780
ctcccacctt tccggcttcc cacccacgcc acccaaagaa gtgtctcctg acccctagcac     840 cacgggggct gcgtctccag cctcatcttc cgcgggggt agtgcagccc gaggagagga     900
caaggacggc gtcaagtacc aggtgtcact gacggagagc atgaagatgg aaagtggcag     960 tccccctgcgc ccaggcctag ctactatggg cacccagcct gctacacacc accccatccc    1020
cacctacccc tcctatgtgc cggcggctgc ccacgactac agcagcggac tcttccaccc    1080
cggaggcttc ctgggggac cggcctccag cttcaccccct aagcagcgca gcaaggctcg    1140
ttcctgttca gaaggccggg agtgtgtcaa ctgtggggcc acagccaccc ctctctggcg    1200
gcgggacggc accggccact acctgtgcaa tgcctgtggc ctctaccaca gatgaatgg    1260 gcagaaccga ccactcatca agcccaagcg aagactgtcg gccgccagaa gagccggcac    1320
ctgttgtgca aattgtcaga cgacaaccac caccttatgg cgccgaaacg ccaacgggga    1380
ccctgtctgc aacgcctgtg gcctctacta caagctgcac aatgttaaca ggccactgac    1440
catgaagaag gaagggatcc agactcggaa ccggaagatg tccaacaagt ccaagaagag    1500
caagaaaggg gcggagtgct tcgaggagct gtcaaagtgc atgcaggaga agtcatcccc    1560
```

```
cttcagtgca gctgccctgg ctggacacat ggctcctgtg ggccaccctcc cgcccttcag    1620 ccactccgga cacatcctgc ccactccgac gcccatccac ccctcctcca gcctctcctt    1680
cggccacccc cacccgtcca gcatggtgac cgccatgggc tagggaacag atggacgtcg    1740
aggaccgggc actcccggat gggtggacca aacccttagc agcccagcat tcccgaagc     1800 cgacaccact cctgcctgcc cggctcggcc cagcaccccc tctcctggag gcgcccagc     1860 agcctgccag cagttactgt gaatgttccc caccgctgag aggctgcctc cgcacctgac    1920
cgctgcccag gtggggtttc ctgcatggac agttgtttgg agaacaacaa ggacaacttt    1980
atgtagagaa aggaggggga cgggacagac gaaggcaacc attttagaa ggaaaaagga    2040 ttaggcaaaa ataatttatt ttgctcttgt ttctaacaag gacttggaga cttggtggtc    2100
tgagctgtcc caagtcctcc ggttcttcct cgggattggc gggtccactt gccagggctc    2160
tgggggcaga tttgtgggga cctcagcctg caccctcttc tcctctggct tccctctctg    2220
aaatagccga actccaggct gggctgagcc aaagccagag tggccacggc cagggagggt   2280
gagctggtgc ctgctttgac gggccaggcc tggaggagga acaatcacg ggcggtcctg    2340 cacagattcc caggccaggg ctgggtcaca ggaaggaaac aacattttct tgaaaggga    2400 aacgtctccc agatcgctcc cttggctttg aggccgaagc tgctgtgact gtgtcccctt    2460
actgagcgca agcacagcct gtcttgtcag gtggaccctg taaatacatc cttttttctg    2520
ctaacccttc aacccctcg cctcctactc tgagacaaaa gaaaaatat taaaaaatg       2580 cataggctta actcgctgat gagttaattg ttttattttt aaactctttt ggggtccagt   2640
tgattgtacg tagccacagg agccctgcta tgaaggaat aaaacctaag gttgggagct    2700
ttgcaattct ttttgggaaa aggggccctt                                     2729
```

<210> SEQ ID NO 14
<211> LENGTH: 480
<212> TYPE: PRT
<213> ORGANISM: Human

<400> SEQUENCE: 14

```
Met Glu Val Ala Pro Glu Gln Pro Gly Trp Met Ala His Pro Ala Val
 1               5                  10                  15

Leu Asn Ala His Asp Pro Asp Ser His His Pro Gly Leu Ala His Asn
             20                  25                  30

Tyr Met Glu Pro Ala His Val Leu Pro Pro Asp Glu Val Asp Val Phe
         35                  40                  45

Phe Asn His Leu Asp Ser Gln Gly Asn Pro Tyr Tyr Ala Asn Pro Ala
     50                  55                  60

His Ala Arg Ala Ala Val Ser Tyr Ser Pro Ala His Ala Arg Leu Thr
 65                  70                  75                  80

Gly Ser Gln Met Cys Arg Pro His Leu Leu His Ser Pro Gly Leu Pro
                 85                  90                  95

Trp Leu Asp Gly Gly Lys Ala Ala Leu Ser Ala Ala Ala His His
             100                 105                 110

His Asn Pro Trp Thr Val Ser Pro Phe Ser Lys Thr Pro Leu His Pro
         115                 120                 125

Ser Ala Ala Gly Gly Pro Gly Gly Pro Leu Ser Val Tyr Pro Gly Ala
     130                 135                 140

Gly Gly Gly Ser Gly Gly Gly Ser Gly Ser Ser Val Ala Ser Leu Thr
145                 150                 155                 160
```

```
Pro Thr Ala Ala His Ser Gly Ser His Leu Phe Gly Phe Pro Pro Thr
                165                 170                 175
Pro Pro Lys Glu Val Ser Pro Asp Pro Ser Thr Gly Ala Ala Ser
            180                 185                 190
Pro Ala Ser Ser Ser Ala Gly Gly Ser Ala Ala Arg Gly Glu Asp Lys
                195                 200                 205
Asp Gly Val Lys Tyr Gln Val Ser Leu Thr Glu Ser Met Lys Met Glu
    210                 215                 220
Ser Gly Ser Pro Leu Arg Pro Gly Leu Ala Thr Met Gly Thr Gln Pro
225                 230                 235                 240
Ala Thr His His Pro Ile Pro Thr Tyr Pro Ser Tyr Val Pro Ala Ala
                245                 250                 255
Ala His Asp Tyr Ser Ser Gly Leu Phe His Pro Gly Gly Phe Leu Gly
                260                 265                 270
Gly Pro Ala Ser Ser Phe Thr Pro Lys Gln Arg Ser Lys Ala Arg Ser
            275                 280                 285
Cys Ser Glu Gly Arg Glu Cys Val Asn Cys Gly Ala Thr Ala Thr Pro
            290                 295                 300
Leu Trp Arg Arg Asp Gly Thr Gly His Tyr Leu Cys Asn Ala Cys Gly
305                 310                 315                 320
Leu Tyr His Lys Met Asn Gly Gln Asn Arg Pro Leu Ile Lys Pro Lys
                325                 330                 335
Arg Arg Leu Ser Ala Ala Arg Arg Ala Gly Thr Cys Cys Ala Asn Cys
            340                 345                 350
Gln Thr Thr Thr Thr Thr Leu Trp Arg Arg Asn Ala Asn Gly Asp Pro
            355                 360                 365
Val Cys Asn Ala Cys Gly Leu Tyr Tyr Lys Leu His Asn Val Asn Arg
    370                 375                 380
Pro Leu Thr Met Lys Lys Glu Gly Ile Gln Thr Arg Asn Arg Lys Met
385                 390                 395                 400
Ser Asn Lys Ser Lys Lys Ser Lys Lys Gly Ala Glu Cys Phe Glu Glu
                405                 410                 415
Leu Ser Lys Cys Met Gln Glu Lys Ser Ser Pro Phe Ser Ala Ala Ala
            420                 425                 430
Leu Ala Gly His Met Ala Pro Val Gly His Leu Pro Pro Phe Ser His
            435                 440                 445
Ser Gly His Ile Leu Pro Thr Pro Thr Pro Ile His Pro Ser Ser Ser
450                 455                 460
Leu Ser Phe Gly His Pro His Pro Ser Ser Met Val Thr Ala Met Gly
465                 470                 475                 480
```

<210> SEQ ID NO 15
<211> LENGTH: 2729
<212> TYPE: DNA
<213> ORGANISM: Human

<400> SEQUENCE: 15

```
tcgagatcca ttgtgctcta aagggagtcg gcagctggcg ccagggcggc cggaggatgc    60
cgaggggccg gagccgggcg ggcccgagcg cgaggcgcac tctaccccca gctcctaccc   120
tgtaagcccc gccagcctcc ggacgtgctg tccctgggcc cgtcgccctc ggggctcccg   180
ccggaactcc ttcactctca gaggccgagt ccctcccctc ccacggctg cgtgtggccg    240
ttgccgtctg cacccagacc ctgagccgcc gcgccggcc atggaggtgg cgccggagca    300
gcccggctgg atggcgcacc cggccgtgct gaatgcgcac gaccccgact cacaccaccc   360
```

```
gggcctggcg cacaactaca tggaacccgc gcacgtgctg cctccagacg aggtggacgt    420
cttcttcaat cacctcgact cgcagggcaa ccctactat gccaaccccg ctcacgcgcg     480
ggcggccgtc tcctacagcc ccgcgcacg ccgcctgacc gggagccaga tgtgccgccc     540
acacttgttg cacagcccgg gtttgccctg gctggacggg ggcaaagcag ccctctctgc    600
cgctgcggcc caccaccaca acccctggac cgtgagcccc ttctccaaga cgccactgca    660
cccctcagct gctggaggcc ctggaggccc actctctgtg tacccagggg ctggggtgg    720
gagcggggga ggcagcggga gctcagtggc ctccctcacc cctacagcag cccactctgg    780
ctcccacctt ttcggcttcc cacccacgcc acccaaagaa gtgtctcctg accctagcac    840
cacgggggct gcgtctccag cctcatcttc cgcgggggt agtgcagccc gaggagagga    900
caaggacggc gtcaagtacc aggtgtcact gacgagagc atgaagatgg aaagtggcag    960
tccctgcgc ccaggcctag ctactatggg cacccagcct gctacacacc ccccatccc    1020
cacctacccc tcctatgtgc cggcggctgc ccacgactac agcagcggac tcttccaccc   1080
cggaggcttc ctgggggac cggcctccag cttcacccct aagcagcgca gcaaggctcg    1140
ttcctgttca gaaggccggg agtgtgtcaa ctgtggggcc acagccaccc ctctctggcg    1200
gcggacggc accggccact acctgtgcaa tgcctgtggc ctctaccaca agatgaatgg    1260
gcagaaccga ccactcatca agcccaagcg aagactgtcg gccgccagaa gagccggcac    1320
ctgttgtgca aattgtcaga cgacaaccac caccttatgg cgccgaaacg ccaacgggga    1380
ccctgtctgc aacgcctgtg gcctctacta caagctgcac aatgttaaca ggccactgac    1440
catgaagaag gaagggatcc agactcggaa ccggaagatg tccaacaagt ccaagaagag    1500
caagaaaggg gcggagtgct tcgaggagct gtcaaagtgc atgcaggaga agtcatcccc    1560
cttcagtgca gctgccctgg ctggacacat ggctcctgtg ggccacctcc cgcccttcag    1620
ccactccgga cacatcctgc ccactccgac gcccatccac ccctcctcca gcctctcctt    1680
cggccacccc cacccgtcca gcatggtgac cgccatgggc tagggaacag atggacgtcg    1740
aggaccgggc actcccggat gggtggacca aacccttagc agcccagcat ttcccgaagc    1800
cgacaccact cctgcctgcc cggctcggcc cagcaccccc tctcctggag ggcgcccagc    1860
agcctgccag cagttactgt gaatgttccc caccgctgag aggctgcctc cgcacctgac    1920
cgctgcccag gtgggtttc ctgcatggac agttgtttgg agaacaacaa ggacaacttt    1980
atgtagagaa aaggagggga cggacagac gaaggcaacc attttagaa ggaaaaagga     2040
ttaggcaaaa ataatttat ttgctcttgt ttctaacaag gacttggaga cttggtggtc     2100
tgagctgtcc caagtcctcc ggttcttcct cgggattggc gggtccactt gccaggctc    2160
tggggcaga tttgtgggga cctcagcctg caccctcttc tcctctggct tccctctctg     2220
aaatagccga actccaggct gggctgagcc aaagccagag tggccacggc cagggagggt    2280
gagctggtgc ctgctttgac gggccaggcc tggagggaga caatcacg ggcggtcctg      2340
cacagattcc caggccaggg ctgggtcaca ggaaggaaac aacatttct tgaaagggga     2400
aacgtctccc agatcgctcc cttggctttg aggccgaagc tgctgtgact gtgtcccctt    2460
actgagcgca agcacagcct gtcttgtcag gtgacccctg taaatacatc ctttttttctg   2520
ctaaccttc aaccccctcg cctcctactc tgagacaaaa gaaaaatat taaaaaaatg      2580
cataggctta actcgctgat gagttaattg ttttatttt aaactctttt ggggtccagt     2640
tgattgtacg tagccacagg agccctgcta tgaaaggaat aaaacctaag gttgggagct    2700
```

-continued

```
ttgcaattct ttttgggaaa aggggcctt                                      2729

<210> SEQ ID NO 16
<211> LENGTH: 52
<212> TYPE: PRT
<213> ORGANISM: chicken
<220> FEATURE:
<221> NAME/KEY: MISC_FEATURE
<222> LOCATION: (1)..(52)
<223> OTHER INFORMATION: X = any amino acid

<400> SEQUENCE: 16

Cys Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa His Xaa Xaa Cys Xaa Xaa Cys Xaa Xaa Cys Xaa
            20                  25                  30

Xaa Xaa Xaa Xaa Xaa Xaa Xaa Xaa Xaa Xaa Xaa Xaa Xaa Xaa Xaa Xaa
        35                  40                  45

Cys Xaa Xaa Cys
    50

<210> SEQ ID NO 17
<211> LENGTH: 19
<212> TYPE: PRT
<213> ORGANISM: Artificial Sequence
<220> FEATURE:
<223> OTHER INFORMATION: Synthetic Protein
<220> FEATURE:
<221> NAME/KEY: MISC_FEATURE
<222> LOCATION: (5)..(5)
<223> OTHER INFORMATION: X = 16 to 23 amino acid
<220> FEATURE:
<221> NAME/KEY: MISC_FEATURE
<222> LOCATION: (16)..(16)
<223> OTHER INFORMATION: X = 16 to 21 amino acid
<220> FEATURE:
<221> NAME/KEY: MISC_FEATURE
<222> LOCATION: (18)..(18)
<223> OTHER INFORMATION: X = 2 to 3 amino acid
<220> FEATURE:
<221> NAME/KEY: MISC_FEATURE
<222> LOCATION: (19)..(19)
<223> OTHER INFORMATION: X = either C, H, or D
<220> FEATURE:
<221> NAME/KEY: MISC_FEATURE
<222> LOCATION: (1)..(18)
<223> OTHER INFORMATION: X = any amino acid

<400> SEQUENCE: 17

Cys Xaa Xaa Cys Xaa His Xaa Xaa Cys Xaa Xaa Cys Xaa Xaa Cys Xaa
1               5                   10                  15

Cys Xaa Xaa
```